United States Patent
Lee et al.

(10) Patent No.: US 7,105,156 B1
(45) Date of Patent: Sep. 12, 2006

(54) METHOD OF USING AN ADENOVIRAL VECTOR ENCODING A RETINOBLASTOMA PROTEIN TO TREAT HYPERPROLIFERATING CELLS

(75) Inventors: Wen-Hwa Lee, San Antonio, TX (US); H. Michael Shepard, Encinitas, CA (US); Richard J. Gregory, Westford, MA (US); Ken N. Wills, Encinitas, CA (US); Daniel C. Maneval, San Diego, CA (US); Eva Lee, San Antonio, TX (US); David Goodrich, East Aurora, NY (US); Nan-Ping Wang, Bellevue, WA (US)

(73) Assignees: The Regents of the University of California, Oakland, CA (US); Canji, Inc., Kenilworth, NJ (US)

( * ) Notice: Subject to any disclaimer, the term of this patent is extended or adjusted under 35 U.S.C. 154(b) by 0 days.

(21) Appl. No.: 08/472,760

(22) Filed: Jun. 7, 1995

Related U.S. Application Data

(60) Continuation-in-part of application No. 08/276,041, filed on Jul. 14, 1994, now abandoned, which is a continuation-in-part of application No. 07/951,947, filed on Sep. 28, 1992, now abandoned, which is a continuation of application No. 07/764,714, filed on Sep. 24, 1991, now abandoned, which is a continuation of application No. 07/265,829, filed on Oct. 31, 1988, now abandoned, application No. 08/472,760, which is a continuation of application No. 08/225,099, filed on Apr. 8, 1994, now Pat. No. 5,578,701, which is a continuation of application No. 08/079,207, filed on Jun. 17, 1993, now abandoned, which is a continuation of application No. 07/914,039, filed on Jul. 14, 1992, now abandoned, which is a continuation of application No. 07/550,877, filed on Jul. 11, 1990, now abandoned, which is a division of application No. 07/098,612, filed on Sep. 17, 1987, now Pat. No. 4,942,123, application No. 08/472,760, which is a division of application No. 08/058,784, filed on May 7, 1993, now Pat. No. 6,051,396, which is a continuation of application No. 07/906,008, filed on Jun. 26, 1992, now abandoned, which is a continuation of application No. 07/553,905, filed on Jul. 16, 1990, now abandoned, application No. 08/472,760, which is a continuation of application No. 08/306,513, filed on Sep. 13, 1994, now Pat. No. 5,851,991, which is a continuation-in-part of application No. 08/121,108, filed on Sep. 13, 1993, now abandoned, which is a continuation-in-part of application No. 07/956,472, filed on Oct. 2, 1992, now abandoned, application No. 08/472,760, which is a continuation-in-part of application No. 08/126,810, filed on Sep. 24, 1993, now abandoned, which is a continuation of application No. 07/778,510, filed on Oct. 17, 1991, now abandoned.

(51) Int. Cl.
  *A61K 35/00* (2006.01)
  *A61K 48/00* (2006.01)
(52) U.S. Cl. ................. 424/93.2; 424/93.1; 424/93.21; 514/44
(58) Field of Classification Search ............... 424/93.2, 424/93.21, 93.1; 514/44; 435/122.3, 320.1, 435/325; 530/350; 536/23.1, 23.5
See application file for complete search history.

(56) References Cited

U.S. PATENT DOCUMENTS

| 4,497,796 | A | 2/1985 | Salser et al. ................. 514/44 |
| 4,736,866 | A | 4/1988 | Leder et al. ................... 800/2 |
| 4,783,313 | A | 11/1988 | Makari et al. ............. 424/1.57 |
| 4,803,072 | A | 2/1989 | Dalton et al. ............. 424/85.5 |
| 4,942,123 | A | 7/1990 | Lee et al. ................. 435/7.23 |
| 5,011,773 | A | 4/1991 | Lee et al. ................. 536/23.2 |
| 5,496,731 | A * | 3/1996 | Xu et al. ................. 435/320.1 |
| 5,932,210 | A * | 8/1999 | Gregory et al. ........... 424/93.2 |
| 6,290,949 | B1 * | 9/2001 | French et al. ............. 424/93.2 |

FOREIGN PATENT DOCUMENTS

| EP | 0259031 A2 | 8/1987 |
| WO | WO89/06703 | 7/1989 |
| WO | WO90/05180 | 5/1990 |
| WO | WO91/09114 | 6/1991 |

OTHER PUBLICATIONS

Orkin, S. et al. (1995), Report & Recommendations of the Panel to Assess the NIH Investment in Research on Gene Therapy.*
Mulligan, R. (1993). Science 260, 926-937.*
Marshall, E (1995), Science 269, 1050-55.*
Culver, K. (1994). Trende—Genins 10, 174-178.*
Weinberg, R. (1995) Cell 81, 323-330.*
Benlcuer, K. (1988). Biotechniques 6, 616-628.*
Miller et al., Targeted vectors for gene therapy, 1995,FASEB J., vol. 9 pp. 190-199.*

(Continued)

*Primary Examiner*—Michael Wilson
(74) *Attorney, Agent, or Firm*—Townsend and Townsend and Crew LLP

(57) ABSTRACT

Disclosed are methods of controlling cell cycle progression by introducing into a cell to be controlled a composition selected from the group consisting of $p56^{RB}$ protein, a fragment of the $p56^{RB}$ protein, and the gene encoding $p56^{RB}$ protein to alter the cell cycle progression while maintaining the viability of the cell. The $p56^{RB}$ protein has been found to have the unexpected and surprising characteristic of being soluble in low concentrations of glycerol, thereby enhancing its value in pharmaceutical applications and the gene encoding $p56^{RB}$ when delivered to the hyperproliferating cell inhibits cellular proliferation.

11 Claims, 39 Drawing Sheets

OTHER PUBLICATIONS

Deonarain, Ligand-targeted receptor-mediated vectors for gene delivery, 1998,Expert Opin. Ther. Pat., vol. 8 pp. 53-69.*

Verma et al., Gene therapy-promises, problems and prospects, 1997, NATURE, vol. 389 pp. 239-242.*

Crystal, Transfer of genes to humans: Early lessons and obstacles to success, 1995, SCIENCE, vol. 270, pp. 404-410.*

Chang et al., Cystostatic gene therapy for vascular proliferative disorders with constitutively active form of the retinoblastoma gene product, 1995, SCIENCE, vol. 267 pp. 518-522.*

Seltzer et al., Inhibition of vascular smooth muscle cell proliferation in vitro and in vivo by a replication-defective adenovirus encoding a non-phosphorylatable retinoblastoma gene product, 1994, CIRCULATION, vol. 90 pp. I-90 abstract Q475.*

Meng et al., Tumor suppressor genes as targets for cancer gene therapy, 1999, Gene Therapy of Cancer, Chapter 1, pp. 3-20.*

Vogelstein et al., The multistep nature of cancer, 1993, Trends in Genetics, vol. 9, pp. 138-141.*

Huang et al., Suppression of the neoplastic phenotype by replacement of the RB gene in human cancer cells, 1988, SCIENCE, vol. 242, pp. 1563-1566.*

Lemarchand et al., Adenovirus-mediated transfer of a recombinant human alpha1-antitrypsin cDNA to human endothelial cells, 1992, Proc. Natl. Acad. Sci. USA, vol. 89, pp. 6482-6486.*

Huang et al., a cellular protein that competes with SV40 T antigen for binding to the retinoblastoma gene product, 1991, NATURE, vol. 350, pp. 160-162.*

Angier, N., "Light Cast on a Darkling Gene." *Discover* Mar.:85-96 (1987).

Bender, et al., "Chromosomal Walking and Jumping to Isolate DNA from the Ace and rosy Loci and the Bithorax Complex in *Drosophila melanogaster*." *J. Mol. Biol.* 168:17-33 (1983).

Benedict, et al., "Nonrandom Chromosomal Changes in Untreated Retinoblastomas." *Cancer Genet. and Cytogenet.* 10:311-333 (1983).

Benedict, et al., "Patient with 13 Chromosome Deletion Evidence that the Retinoblastoma Gene Is a Recessive Cancer Gene." *Science* 219:973-975 (1983).

Bignon, et al., "Expression of a retinoblastoma transgene results in dwarf mice." *Genes & Development* 7:1654-1662 (1993).

Bookstein, et al., "Human retinoblastoma susceptibility gene: Genomic organization and analysis of heterozygous intragenic deletion mutants." *Proceedings of the National Academy of Sciences* 85:2210-2214 (1988).

Bookstein, et al., "Suppression of Tumorigenicity of Human Prostate Carcinoma Cells by Replacing a Mutated RB Gene." *Science* 247:712-715 (1990).

Bowen, et al., "The detection of DNA-binding proteins by protein blotting." *Nucleic Acids Research* 8:1-20 (1980).

Buchkovich, et al., "The Retinoblastoma Protein Is Phosphorylated during Specific Phases of the Cell Cycle." *Cell* 58:1097-1105 (1989).

Capecchi, Mario R, "Altering the Genome by Homologous Recombination." *Science* 244:1288-1292 (1989).

Cavenee, et al., "Expression of recessive alleles by chromosomal mechanisms in retinoblastoma." *Nature* 305:779-783 (1983).

Cavenee, et al., "Isolation and Regional Localization of DNA Segments Revealing Polymorphic Loci from Human Chromosome 13." *Am. J. Hum. Genet.* 36:10-24 (1984).

Cepko, et al., "Construction and Applications of a Highly Transmissible Murine Retrovirus Shuttle Vector." *Cell* 37:1053-1062 (1984).

Chen, et al., "Phosphorylation of the Retinoblastoma Gene Product Is Modulated during the Cell Cycle and Cellular Differentiation." *Cell* 58:1193-1198 (1989).

Cooper, Geoffrey M. "Tumor Suppressor Genes." *Oncogenes*, 121-139 (1990).

Cooper, J.A. and Whyte, Peter, "RB and the Cell Cycle: Entrance or Exit?" Cell 58:1009-1011 (1989).

Cordaro, J.C., "Transgenic Mice as Future Tools in Risk Assessment." *Risk Analysis* 9(2):157-168 (1989).

Cordon-Cardo, et al., "Altered Expression of the Retinoblastoma Gene Product: Prognostic Indicator in Bladder Cancer." *J. Natl. Cancer Inst.* 84(16):1251-1256 (1992).

DeCaprio, et al., "The Product of the Retinoblastoma Susceptibility Gene Has Properties of a Cell Cycle Regulatory Element." *Cell* 58:1085-1095 (1989).

DeCaprio, et al., "SV40 Large Tumor Antigen Forms a Specific Complex with the Product of the Retinoblastoma Susceptibility Gene." *Cell* 54:275-283 (1988).

Dixon, Richard A. and Nathans, Daniel, "Purification of Simian Virus 40 Large T Antigen by Immunoaffinity Chromatography." *Journal of Virology* 53:1001-1004 (1985).

Doerfler, W., "Expression of the *Autographa californica* Nuclear Polyhedrosia Virus Genome in Insect Cells: Homologous Viral and Heterologous Vertebrate Genes—The Baculovirus Vector System." *Current Topics in Microl. Immunol.* 131:51-68 (1986).

Donner, et al., "Nuclear localization and DNA binding of the transforming gene product of avian myelocytomatosis virus." *Nature* 296:262-266 (1982).

Dryja, et al., "Chromosome 13 Homozygosity in Osteosarcoma without Retinoblastoma." *Am. J. Hum Genet.* 38:59-66 (1986).

Dryja, et al., "Genetic Sequences That Predispose to Retinoblastoma and Osteosarcoma." *Symposium on Fundamental Cancer Research* 39:115-119 (1987).

Dryja, et al., "Molecular detection of deletions involving band q14 of chromosome 13 in retinoblastomas." *Proceedings of the National Academy of Sciences* 83:7391-7394 (1986).

Dyson, et al., "The Human Papilloma Virus-16 E7 Oncoprotein Is Able to Bind to the Retinoblastoma Gene Product." Science 243:934-937 (1989).

Edwards, et al., "Purification and Characterization of a Functionally Homogenous 60-kDa Species of the Retinoblastoma Gene Product" *The Journal of Biological Chemistry* 267(12):7971-7974 (1992).

Eliyahu, et al., "Wild-type p53 can inhibit oncogene-mediated focus formation." *Proceedings of the National Academy of Sciences* 86:8763-8767 (1989).

Friedmann, Theodore, "Gene Therapy of Cancer through Restoration of Tumor-Suppressor Functions?" *Cancer* 20:1810-1817 (1992).

Friedmann, Theodore, "Progress Toward Human Gene Therapy." *Science* 244:1275-1281 (1989).

Friend, et al., "Deletions of a DNA sequence in retinoblastomas and mesenchymal tumors: Organization of the sequence and its encoded protein." *Proceedings of the National Academy of Sciences* 84:9059-9063 (1987).

Friend, et al., "A human DNA segment with properties of the gene that predisposes to retinoblastoma and osteosarcoma." *Nature* 323:643-646 (1986).

Fung, et al., "Structural Evidence for the Authenticity of the Human Retinoblastoma Gene." *Science* 236:1657-1661 (1987).

Funk, Sarah E. and Sage, E. Helene, "The $Ca^{2+}$-binding glycoprotein SPARC modulates cell cycle progression in bovine aortic endothelial cells." *Proceedings of the National Academy of Sciences* 88:2648-2652 (1991).

Gishizky, et al., "Efficient transplantation of BCR-ABL-induced chronic myelogenous leukemia-like syndrome in mice." *Proceedings of the National Academy of Sciences* 90-3755-3759 (1993).

Gluzman, Yakov, "SV40-Transformed Simian Cells Support the Replication of Early SV40 Mutants." *Cell* 23:175-182 (1981).

Goodrich, D.W. and Lee, Wen-Hwa, "Molecular characterization of the retinoblastoma susceptibility gene." *Biochimica et Biophysica Acta* 1155:43-61 (1993).

Goodrich, et al., "The Retinoblastoma Gene Product Regulates Progression through the G1 Phase of the Cell Cycle." *Cell* 67:293-302 (1991).

Gossler, et al., "Transgenesis by means of blastocyst-derived embryonic stem cell lines." *Proceedings of the National Academy of Sciences* 83:9065-9069 (1986).

Gu, et al., "Interaction of Myogenic Factors and the Retinoblastoma Protein Mediates Muscles Cell Commitment and Differentiation." *Cell* 72:309-324 (1993).

Harbour, et al., "Abnormalities in Structure and Expression of the Human Retinoblastoma Gene in SCLC." *Science* 241:353-356 (1988).

Harris, Henry, "Malignant tumours generated by recessive mutations." *Nature* 323:582-583 (1986).

Helin, et al., "A cDNA Encoding a pRB-Binding Protein with Properties of the Transcription Factor E2F." *Cell* 70:337-350 (1992).

Hird, V. and Epenetos, A.A., "Immunotherapy with Monoclonal Antibodies." *Genes and Cancer*, John Wiley & Sons, New York, NY, 183-189 (1990).

Hong, et al., "Structure of the human retinoblastoma gene." *Proceedings of the National Academy of Sciences* 86:5502-5506 (1989).

Hooper, et al., "HPRT-deficient (Lesch-Nyhan) mouse embryos derived from germline colonization by cultured cells." *Nature* 326:292-295 (1987).

Horowitz, et al., "Frequent inactivation of the retinoblastoma antioncogene is restricted to a subset of human tumor cell." *Proceedings of the National Academy of Sciences* 87:2775-2779 (1990).

Horowitz, et al., "Point Mutational Inactivation of the Retinoblastoma Antioncogene." *Science* 243:937-940 (1989).

Hu, et al., "The regions of the retinoblastoma protein needed for binding to adenovirus E1A or SV40 large T antigen are common sites for mutations." *The EMBO Journal* 9(4):1147-1155 (1990).

Huang, et al., "Suppression of the Neoplastic Phenotype by Replacement of the RB Gene in Human Cancer Cells." *Science* 242:1563-66 (1988).

Huang, et al., "A cellular protein that competes with SV40 T antigen for binding to the retinoblastoma gene product." *Nature* 350:160-162 (1991).

Huang, et al., "Two distinct and frequently mutated regions of retinoblastoma protein are required for binding to SV40 T antigen." *The EMBO Journal* 9(6):1815-1822 (1990).

Hudson, et al., *Practical Immunology*, Blackwell Scientific Publications, 338-340 (1980).

Jansen, et al., "Successful Treatment of Human Acute T-Cell Leukemia in SCID Mice Using the Anti-CD7-deglycosylated Ricin A-Chain Immunotoxin DA7." *Cancer Research* 52:1314-1321 (1992).

Jeang, et al., "Abundant Synthesis of Functional Human T-Cell Leukemia Virus Type I p40$^x$ Protein in Eucaryotic Cells by Using a Baculovirus Expression Vector." *Journal of Virology* 61(3):708-713 (1987).

Kantoff, et al., "Correction of adenosine deaminase deficiency in cultured human T and B cells by retrovirus-mediated gene transfer." *Proceedings of the National Academy of Sciences* 83:6563-6567 (1986).

Kaye, et al., "A single amino acid substitution results in a retinoblastoma protein defective in phosphorylation and oncoprotein binding." *Proceedings of the National Academy of Sciences* 87:6922-6926 (1990).

Kitagawa, et al., "cdc2-like kinase is associated with the retinoblastoma protein." *Oncogene* 7:1067-1074 (1992).

Kuehn, et al., "A potential animal model for Lesch-Nyhan syndrome through introduction of HPRT mutations into mice." *Nature* 326:295-298 (1987).

LaLande, et al., "Isolation of Human Chromosome 13-Specific DNA Sequences Cloned from Flow Sorted Chromosomes and Potentially Linked to the Retinoblastoma Locus." *Cancer Genetics and Cytogenetics* 13:283-295 (1984).

LaLande, et al., "Molecular Detection and Differentiation of Deletions in Band 13q14 in Human Retinoblastoma." *Cancer Genet. Cytogenet.* 23:151-157 (1986).

Lee, Eva Y-H.P., et al., "Inactivation of the Retinoblastoma Susceptibility Gene in Human Breast Cancers." *Science* 241:218-221 (1988).

Lee, et al., "Molecular cloning of the human esterase D gene, a genetic market of retinoblastoma." *Proceedings of the National Academy of Sciences* 83:6337-6341 (1986).

Lee, et al., "Molecular mechanism of retinoblastoma gene inactivation in retinoblastoma cell line Y79." *Proceedings of the National Academy of Sciences* 85:6017-6021 (1988).

Lee, et al., "Human Retinoblastoma Susceptibility Gene: Cloning, Identification and Sequence." *Science* 235:1394-1399 (1987).

Lee, et al., "Purification, biochemical characterization, and biological function of human esterase D." *Proceedings of the National Academy of Sciences* 83:6790-6794 (1986).

Lee, et al., "The retinoblastoma susceptibility gene encodes a nuclear phosphoprotein associated with DNA binding activity." *Nature* 329:642-645 (1987).

Levine, Arnold, "The Tumor Suppressor Genes." *Annu. Rev. Biochem.* 62:623-651 (1993).

Ludlow, et al., "SV40 Large T Antigen Binds Preferentially to an Underphosporylated Member of the Retinoblastoma Susceptibility Gene Product Family." *Cell* 56:57-65 (1989).

Lundberg, et al., "Loss of heterozygosity in human ductal breast tumors indicates a recessive mutation on chromosomes 13." *Proceedings of the National Academy of Sciences* 84:2372-2376 (1987).

Mann, et al., "Construction of a Retrovirus Packaging Mutant and Its Use to Produce Helper-Free Defective Retrovirus." *Cell* 33:153-159 (1983).

Matsuura, "Baculovirus Expression Vectors: the Requirements for High Level Expression of Proteins, Including Glycoproteins." *J. Gen. Virol.* 68:1233-1250 (1987).

McCune, et al., "The SCID-hu Mouse: Murine Model for the Analysis of Human Hematolymphoid Differentiation and Function." *Science* 241: 1632-1639 (1988).

Mendoza, et al., "A Case of Synovial Sarcoma with Abnormal Expression of the Human Retinoblastoma Susceptibility Gene." *Human Pathology* 19:487-489 (1988).

Mihara, et al., "Cell Cycle-Dependent Regulation of Phosphorylation of the Human Retinoblastoma Gene Product." *Science* 246:1300-1303 (1989).

Miller, et al., "Generation of Helper-Free Amphotropic Retroviruses That Transduce a Dominant-Acting, Methotrexate-Resistant Dihydrofolate Reductase Gene." *Mol. Cell. Biol.* 5(3):431-437 (1985).

Miller, et al., "Transfer of Genes into Human Somatic Cells Using Retrovirus Vectors." *Cold Spring Harbor Symposia on Quantitative Biology* LI:1013-1019 (1986).

Miller, et al., "A transmissible retrovirus expressing human hypoxanthine phosphoribosyltransferase (HPRT) : Gene transfer into cells obtained from humans deficient in HPRT." *Proceedings of the National Academy of Sciences USA* 80:4709-4713 (1983).

Miyamoto, et al., "Production of Human c-myc Protein in Insect Cells Infected with a Baculovirus Expression Vector." *Molecular and Cell Biology* 5(10):2860-2865 (1987).

Mosier, et al., "Transfer of a functional human immune system to mice with severe combined immunodeficiency." *Nature* 335:256-259 (1988).

Murphree, A. Linn and Benedict, William F., "Retinoblastoma: Clues to Human Oncogenesis." *Science* 223:1028-1033 (1984).

Pendergast, et al., "Baculovirus expression of functional P210 BCR-ABL oncogene product." *Oncogene* 4:759-766 (1989).

Ramsay, et al., "Human Proto-Oncogene N-myc Encodes Nuclear Proteins That Bind DNA." *Molecular and Cellular Biology* 6(12):4450-4457 (1986).

Ratajczak, et al., "*In vivo* treatment of human leukemia in a scid mouse model with c-myb antisense oligodeoxynucleotides." *Proceedings of the National Academy of Sciences* 89:11823-11827 (1992).

Reissmann, et al., "Inactivation of the retinoblastoma susceptibility gene in non-small-cell lung cancer." *Oncogene* 8:1913-1919 (1993).

Sachse, et al., "DNA aberrations at the retinoblastoma gene locus in human squamous cell carcinomas of the lung." *Oncogene* 9:39-47 (1994).

Sager, Ruth, "Tumor Suppressor Genes: The Puzzle and the Promise." *Science* 246:1406-1412 (1989).

Schneider, et al., "A One-step Purification of Membrane Proteins Using a High Efficiency Immunomatrix." *J. Biol. Chem.* 257(18):10766-10769 (1982).

Shew, et al., "Antibodies Detecting Abnormalities of the Retinoblastoma Susceptibility Gene Product (pp110$^{RB}$) in Osteosarcomas and Synovial Sarcomas." *Oncogene Research* 1:205-214 (1989).

Shew, et al., "C-terminal truncation of the retinoblastoma gene product leads to functional inactivation." *Proceedings of the National Academy of Sciences* 87:6-10 (1990).

Simanis, V., and Lane, D.P., "An Immunoaffinity Purification Procedure for SV40 Large T Antigen." *Virology* 144:88-100 (1985).

Smith, G.E., et al., "Production of Human Beta Interferon in Insect Cells Infected with a Baculovirus Expression Vector." *Mol. Cell. Biol.* 3(12):2156-2165 (1983).

Strong, et al., "Familial Retinoblastoma and Chromosome 13 Deletion Transmitted via an Insertional Translocation." *Science* 213:1501-1503 (1981).

Takahashi, et al., "The retinoblastoma gene functions as a growth and tumor suppressor in human bladder carcinoma cells." *Proceedings of the National Academy of Sciences* 88:5257-5261 (1991).

Tertoolen, et al., "Electrophysiological responses to bradykinin and microinjected inositol polyphosphates in neuroblastoma cells." *FEBS Lett.* 214:365-369 (1987).

Thomas, et al., "High Frequency Targeting of Genes to Specific Sites in the Mammalian Genome." *Cell* 44:419-428 (1986).

Thomas, Kirk R. and Capecchi, Mario R., "Site-Directed Mutagenesis by Gene Targeting in Mouse Embryo-Derived Stem Cells." *Cell* 51:503-512 (1987).

Toguchida, et al., "Chromosomal Reorganization for the Expression of Recessive Mutation of Retinoblastoma Susceptibility Gene in the Development of Osteosarcoma" *Cancer Research* 48:3939-3943 (1988).

Wang, et al., "Expression of the Human Retinoblastoma Gene Product $pp110^{RB}$ in Insect Cells Using the Baculovirus System." *Cell Growth & Differ.* 1:429-437 (1990).

Ward, et al., "Location of the retinoblastoma susceptibility gene(s) and the human esterase D locus." *Journal of Medical Genetics* 21:92-95 (1984).

Weissman, et al., "Introduction of a Normal Human Chromosome 11 into a Wilms' Tumor Cell Line Controls Its Tumorigenic Expression." *Science* 236:175-180 (1987).

Whyte, et al., "Association between an oncogene and an anti-oncogene: the adenovirus E1A proteins bind to the retinoblastoma gene product." *Nature* 334:124-129 (1988).

Yokota, et al., "Altered expression of the retinoblastoma (RB) gene in small-cell carcinoma of the lung." *Oncogene* 3:471-475 (1988).

Yunis, J., and Ramsay, N., "Retinoblastoma and Subband Deletion of Chromosome 13." *Am J Dis Child* 132:161-163, (1978).

* cited by examiner

```
TTCCGGTTTT TCTCAGGGGA CGTGAAATT ATTTTGTAA CGGGAGTCGG GAGAGGACGG      60
GGCGTGCCCC GCGTGCCGC GCGTCGTCCT CCCCGGCGCT CCTCCACAGC TCGCTGGCTC    120
CCGCCGCGGA AAGGCGTC ATG CCG CCC AAA ACC CCC CGA AAA ACG GCC GCC    171
               Met Pro Pro Lys Thr Pro Arg Lys Thr Ala Ala
                                5                       10

ACC GCC GCC GCT GCC GCC GCG GAA CCC CCG GCA CCG CCG CCG CCC        219
Thr Ala Ala Ala Ala Ala Ala Glu Pro Pro Ala Pro Pro Pro Pro
                15                          20                  25

CCT CCT GAG GAG GAC CCA GAG CAG GAC AGC GGC CCG GAG GAC CTG CCT    267
Pro Pro Glu Glu Asp Pro Glu Gln Asp Ser Gly Pro Glu Asp Leu Pro
            30                      35                      40

CTC GTC AGG CTT GAG TTT GAA ACA GAA GAA CCT GAT TTT ACT GCA        315
Leu Val Arg Leu Glu Phe Glu Thr Glu Glu Pro Asp Phe Thr Ala
            45                      50                      55

TTA TGT CAG AAA TTA AAG ATA CCA GAT CAT GTC AGA GAG AGA GCT TGG    363
Leu Cys Gln Lys Leu Lys Ile Pro Asp His Val Arg Glu Arg Ala Trp
            60                      65                      70      75
```

FIG. 7A

```
TTA ACT TGG GAG AAA GTT TCA TCT GTG GAT GGA GTA TTG GGA GGT TAT        411
Leu Thr Trp Glu Lys Val Ser Ser Val Asp Gly Val Leu Gly Gly Tyr
             80                          85                  90

ATT CAA AAG AAA AAG GAA CTG TGG GGA ATC TGT ATC TTT ATT GCA GCA        459
Ile Gln Lys Lys Lys Glu Leu Trp Gly Ile Cys Ile Phe Ile Ala Ala
             95                         100                 105

GTT GAC CTA GAT GAG ATG TCG TTC ACT TTT ACT GAG CTA CAG AAA AAC        507
Val Asp Leu Asp Glu Met Ser Phe Thr Phe Thr Glu Leu Gln Lys Asn
            110                         115                 120

ATA GAA ATC AGT GTC CAT AAA TTC TTT AAC TTA CTA AAA GAA ATT GAT        555
Ile Glu Ile Ser Val His Lys Phe Phe Asn Leu Leu Lys Glu Ile Asp
            125                         130                 135

ACC AGT ACC AAA GTT GAT AAT GCT ATG TCA AGA CTG TTG AAG AAG TAT        603
Thr Ser Thr Lys Val Asp Asn Ala Met Ser Arg Leu Leu Lys Lys Tyr
            140                         145          150        155

GAT GTA TTG TTT GCA CTC TTC AGC AAA TTG GAA AGG ACA TGT GAA CTT        651
Asp Val Leu Phe Ala Leu Phe Ser Lys Leu Glu Arg Thr Cys Glu Leu
            160                         165                 170
```

*FIG. 7B*

```
ATA TAT TTG ACA CAA CCC AGC AGT TCG ATA TCT ACT GAA ATA AAT TCT    699
Ile Tyr Leu Thr Gln Pro Ser Ser Ser Ile Ser Thr Glu Ile Asn Ser
            175                 180                 185

GCA TTG GTG CTA AAA GTT TCT TGG ATC ACA TTT TTA TTA GCT AAA GGG    747
Ala Leu Val Leu Lys Val Ser Trp Ile Thr Phe Leu Leu Ala Lys Gly
            190                 195                 200

GAA GTA TTA CAA ATG GAA GAT GAT CTG GTG ATT TCA TTT CAG TTA ATG    795
Glu Val Leu Gln Met Glu Asp Asp Leu Val Ile Ser Phe Gln Leu Met
        205                 210                 215

CTA TGT GTC CTT GAC TAT TTT ATT AAA CTC TCA CCT CCC ATG TTG CTC    843
Leu Cys Val Leu Asp Tyr Phe Ile Lys Leu Ser Pro Pro Met Leu Leu
        220                 225                 230             235

AAA GAA CCA TAT AAA ACA GCT GTT ATA CCC ATT AAT GGT TCA CCT CGA    891
Lys Glu Pro Tyr Lys Thr Ala Val Ile Pro Ile Asn Gly Ser Pro Arg
            240                 245                 250

ACA CCC AGG CGA GGT CAG AAC AGG AGT GCA CGG ATA GCA AAA CAA CTA    939
Thr Pro Arg Arg Gly Gln Asn Arg Ser Ala Arg Ile Ala Lys Gln Leu
            255                 260                 265
```

FIG. 7C

```
GAA AAT GAT ACA AGA ATT ATT GAA GTT CTC TGT AAA GAA CAT GAA TGT      987
Glu Asn Asp Thr Arg Ile Ile Glu Val Leu Cys Lys Glu His Glu Cys
                270                 275                 280

AAT ATA GAT GAG GTG AAA AAT GTT TAT TTC AAA AAT TTT ATA CCT TTT     1035
Asn Ile Asp Glu Val Lys Asn Val Tyr Phe Lys Asn Phe Ile Pro Phe
            285                 290                 295

ATG AAT TCT CTT GGA CTT GTA ACA TCT AAT GGA CTT CCA GAG GTT GAA     1083
Met Asn Ser Leu Gly Leu Val Thr Ser Asn Gly Leu Pro Glu Val Glu
                300                 305                 310                 315

AAT CTT TCT AAA CGA TAC GAA ATT TAT CTT AAA ACT CTT CAG ACT GAT CTA 1131
Asn Leu Ser Lys Arg Tyr Glu Ile Tyr Leu Lys Thr Leu Gln Thr Asp Leu
            320                 325                 330

GAT GCA AGA TTA TTT TTG GAT CAT GAT AAA GAT CAT GAT TCT             1179
Asp Ala Arg Leu Phe Leu Asp His Asp Lys Asp His Asp Ser
            335                 340                 345

ATA GAC AGT TTT GAA ACA CAG AGA ACA CCA CGA AAA AGT AAC CTT GAT     1227
Ile Asp Ser Phe Glu Thr Gln Arg Thr Pro Arg Lys Ser Asn Leu Asp
            350                 355                 360
```

*FIG. 7D*

```
GAA GAG GTG AAT GTA ATT CCT CCA CAC ACT CCA GTT AGG ACT GTT ATG    1275
Glu Glu Val Asn Val Ile Pro Pro His Thr Pro Val Arg Thr Val Met
365                     370                     375

AAC ACT ATC CAA CAA TTA ATG ATG ATT TTA AAT TCA GCA AGT GAT CAA    1323
Asn Thr Ile Gln Gln Leu Met Met Ile Leu Asn Ser Ala Ser Asp Gln
        380                     385                     390                 395

CCT TCA GAA AAT CTG ATT TCC TAT TTT AAC AAC TGC ACA GTG AAT CCA    1371
Pro Ser Glu Asn Leu Ile Ser Tyr Phe Asn Asn Cys Thr Val Asn Pro
                400                     405                     410

AAA GAA AGT ATA CTG AAA AGA GTG AAG GAT ATA GGA TAC ATC TTT AAA    1419
Lys Glu Ser Ile Leu Lys Arg Val Lys Asp Ile Gly Tyr Ile Phe Lys
        415                     420                     425

GAG AAA TTT GCT AAA GCT GTG GGA CAG GGT TGT GTC GAA ATT GGA TCA    1467
Glu Lys Phe Ala Lys Ala Val Gly Gln Gly Cys Val Glu Ile Gly Ser
                430                     435                     440
```

*FIG. 7E*

```
CAG CGA TAC AAA CTT GGA GTT CGC TTG TAT TAC CGA GTA ATG GAA TCC    1515
Gln Arg Tyr Lys Leu Gly Val Arg Leu Tyr Tyr Arg Val Met Glu Ser
            445                     450                 455

ATG CTT AAA TCA GAA GAA CGA TTA TCC ATT CAA AAT TTT AGC AAA         1563
Met Leu Lys Ser Glu Glu Arg Leu Ser Ile Gln Asn Phe Ser Lys
    460                 465                 470             475

CTT CTG AAT GAC AAC ATT TTT CAT ATG TCT TTA TTG GCG TGC GCT CTT    1611
Leu Leu Asn Asp Asn Ile Phe His Met Ser Leu Leu Ala Cys Ala Leu
            480                     485                 490

GAG GTT GTA ATG GCC ACA TAT AGC AGA AGT ACA TCT CAG AAT CTT GAT    1659
Glu Val Val Met Ala Thr Tyr Ser Arg Ser Thr Ser Gln Asn Leu Asp
        495                     500                 505

TCT GGA ACA GAT TTG TCT TTC CCA TGG ATT CTG AAT GTG CTT AAT TTA    1707
Ser Gly Thr Asp Leu Ser Phe Pro Trp Ile Leu Asn Val Leu Asn Leu
    510                     515                     520
```

*FIG. 7F*

```
AAA GCC TTT GAT TTT TAC AAA GTG ATC GAA AGT TTT ATC AAA GCA GAA    1755
Lys Ala Phe Asp Phe Tyr Lys Val Ile Glu Ser Phe Ile Lys Ala Glu
525                 530                 535

GGC AAC TTG ACA AGA GAA ATG ATA AAA CAT TTA GAA CGA TGT GAA CAT    1803
Gly Asn Leu Thr Arg Glu Met Ile Lys His Leu Glu Arg Cys Glu His
540                 545                 550                 555

CGA ATC ATG GAA TCC CTT GCA TGG CTC TCA CCT TTA TTT GAT            1851
Arg Ile Met Glu Ser Leu Ala Trp Leu Ser Pro Leu Phe Asp
560                 565                 570

CTT ATT AAA CAA TCA AAG GAC CGA GAA GGA CCA ACT GAT CAC CTT GAA    1899
Leu Ile Lys Gln Ser Lys Asp Arg Glu Gly Pro Thr Asp His Leu Glu
575                 580                 585

TCT GCT TGT CCT CTT AAT CTT CCT CTC CAG AAT AAT CAC ACT GCA GCA    1947
Ser Ala Cys Pro Leu Asn Leu Pro Leu Gln Asn Asn His Thr Ala Ala
590                 595                 600

GAT ATG TAT CTT TCT CCT GTA AGA TCT CCA AAG AAA GGT TCA ACT        1995
Asp Met Tyr Leu Ser Pro Val Arg Ser Pro Lys Lys Gly Ser Thr
605                 610                 615
```

*FIG. 7G*

```
ACG CGT GTA AAT TCT ACT GCA AAT GCA GAG ACA CAA GCA ACC TCA GCC    2043
Thr Arg Val Asn Ser Thr Ala Asn Ala Glu Thr Gln Ala Thr Ser Ala
620                 625                 630                 635

TTC CAG ACC CAG AAG CCA TTG AAA TCT ACC CTT TCA CTG TTT TAT        2091
Phe Gln Thr Gln Lys Pro Leu Lys Ser Thr Leu Ser Leu Phe Tyr
        640                 645                 650

AAA AAA GTG TAT CGG CTA GCC TAT CTC CGG CTA AAT ACA CTT TGT GAA    2139
Lys Lys Val Tyr Arg Leu Ala Tyr Leu Arg Leu Asn Thr Leu Cys Glu
            655                 660                 665

CGC CTT CTG TCT GAG CAC CCA GAA TTA GAA CAT ATC ATC TGG ACC CTT    2187
Arg Leu Leu Ser Glu His Pro Glu Leu Glu His Ile Ile Trp Thr Leu
                670                 675                 680

TTC CAG CAC ACC CTG CAG AAT GAG TAT GAA CTC ATG AGA GAC AGG CAT    2235
Phe Gln His Thr Leu Gln Asn Glu Tyr Glu Leu Met Arg Asp Arg His
        685                 690                 695
```

*FIG. 7H*

```
TTG GAC CAA ATT ATG ATG TGT TCC ATG TAT GGC ATA TGC AAA GTG AAG    2283
Leu Asp Gln Ile Met Met Cys Ser Met Tyr Gly Ile Cys Lys Val Lys
700                 705                 710                 715

AAT ATA GAC CTT AAA TTC AAA ATC ATT GTA ACA GCA TAC AAG GAT CTT    2331
Asn Ile Asp Leu Lys Phe Lys Ile Ile Val Thr Ala Tyr Lys Asp Leu
        720                 725                 730

CCT CAT GCT GTT CAG GAG ACA TTC AAA CGT GTT TTG ATC AAA GAA GAG    2379
Pro His Ala Val Gln Glu Thr Phe Lys Arg Val Leu Ile Lys Glu Glu
            735                 740                 745

GAG TAT GAT TCT ATT ATA GTA TTC TAT AAC TCG GTC TTC ATG CAG AGA    2427
Glu Tyr Asp Ser Ile Ile Val Phe Tyr Asn Ser Val Phe Met Gln Arg
                750                 755                 760

CTG AAA ACA AAT ATT TTG CAG TAT GCT TCC ACC AGG CCC CCT ACC TTG    2475
Leu Lys Thr Asn Ile Leu Gln Tyr Ala Ser Thr Arg Pro Pro Thr Leu
765                 770                 775

FIG. 71
```

```
TCA CCA ATA CCT CAC ATT CCT CGA AGC CCT TAC AAG TTT CCT AGT TCA   2523
Ser Pro Ile Pro His Ile Pro Arg Ser Pro Tyr Lys Phe Pro Ser Ser
780             785                 790                 795

CCC TTA CGG ATT CCT GGA GGG AAC ATC TAT ATT TCA CCC CTG AAG AGT   2571
Pro Leu Arg Ile Pro Gly Gly Asn Ile Tyr Ile Ser Pro Leu Lys Ser
            800                 805                 810

CCA TAT AAA ATT TCA GAA GGT CTG CCA ACA CCA ACA AAA ATG ACT CCA   2619
Pro Tyr Lys Ile Ser Glu Gly Leu Pro Thr Pro Thr Lys Met Thr Pro
        815                 820                 825

AGA TCA AGA ATC TTA GTA TCA ATT GGT GAA TCA TTC GGG ACT TCT GAG   2667
Arg Ser Arg Ile Leu Val Ser Ile Gly Glu Ser Phe Gly Thr Ser Glu
830                 835                 840

AAG TTC CAG AAA ATA AAT CAG ATG GTA TGT AAC AGC GAC CGT GTG CTC   2715
Lys Phe Gln Lys Ile Asn Gln Met Val Cys Asn Ser Asp Arg Val Leu
    845                 850                 855

AAA AGA AGT GCT GAA GGA AGC AAC CCT CCT AAA CCA CTG AAA AAA CTA   2763
Lys Arg Ser Ala Glu Gly Ser Asn Pro Pro Lys Pro Leu Lys Lys Leu
860                 865                 870                 875
```

*FIG. 7J*

```
CGC TTT GAT ATT GAA GGA TCA GAT GAA GCA GAT GGA AGT AAA CAT CTC    2811
Arg Phe Asp Ile Glu Gly Ser Asp Glu Ala Asp Gly Ser Lys His Leu
            880                     885                     890

CCA GAG TCC AAA TTT CAG CAG AAA CTG GCA GAA ATG ACT TCT ACT        2859
Pro Gly Glu Ser Lys Phe Gln Gln Lys Leu Ala Glu Met Thr Ser Thr
            895                     900                     905

CGA ACA CGA ATG CAA AAG CAG AAA ATG AAT GAT AGC ATG GAT ACC TCA    2907
Arg Thr Arg Met Gln Lys Gln Lys Met Asn Asp Ser Met Asp Thr Ser
            910                     915                     920

AAC AAG GAA GAG AAA TGAGGATCTC AGGACCTTGG TGGACACTGT GTACACCTCT    2962
Asn Lys Glu Glu Lys
        925

GGATTCATTG TCTCTCACAG ATGTGACTGA TAT                               2995
```

```
TTCCGGTTTT TCTCAGGGGA CGTGAAATT ATTTTGTAA CGGGAGTCGG GAGAGGACGG      60
GGCGTGCCCC GCGTGCGCGC GCGTCGTCCT CCCCGGCGCT CCTCCACAGC TCGCTGGCTC   120
CCGCCGCGGA AAGGCGTC ATG CCG CCC AAA ACC CCC CGA AAA ACG GCC GCC    171
              Met Pro Pro Lys Thr Pro Arg Lys Thr Ala Ala
               1                 5                      10

ACC GCC GCC GCT GCC GCG GCG GAA CCC GCA CCG GCA CCG CCG CCG CCC    219
Thr Ala Ala Ala Ala Ala Ala Glu Pro Ala Pro Ala Pro Pro Pro Pro
                  15                       20                 25

CCT CCT GAG GAG GAC CCA GAG GAC AGC GGC CCG GAG GAC CTG CCT        267
Pro Pro Glu Glu Asp Pro Glu Asp Ser Gly Pro Glu Asp Leu Pro
         30                  35                      40

CTC GTC AGG CTT GAG TTT GAA GAA ACA GAA GAA CCT GAT TTT ACT GCA    315
Leu Val Arg Leu Glu Phe Glu Glu Thr Glu Glu Pro Asp Phe Thr Ala
          45                      50                   55

TTA TGT CAG AAA TTA AAG ATA CCA GAT CAT GTC AGA GAG AGA GCT TGG    363
Leu Cys Gln Lys Leu Lys Ile Pro Asp His Val Arg Glu Arg Ala Trp
 60                  65                     70                  75
```

FIG. 9A

```
TTA ACT TGG GAG AAA GTT TCA TCT GTG GAT GGA GTA TTG GGA GGT TAT    411
Leu Thr Trp Glu Lys Val Ser Ser Val Asp Gly Val Leu Gly Gly Tyr
                 80                      85                  90

ATT CAA AAG AAA AAG GAA CTG TGG GGA ATC TGT ATC TTT ATT GCA GCA    459
Ile Gln Lys Lys Lys Glu Leu Trp Gly Ile Cys Ile Phe Ile Ala Ala
             95                     100                 105

GTT GAC CTA GAT GAG ATG TCG TTC ACT TTT ACT GAG CTA CAG AAA AAC    507
Val Asp Leu Asp Glu Met Ser Phe Thr Phe Thr Glu Leu Gln Lys Asn
         110                     115                 120

ATA GAA ATC AGT GTC CAT AAA GTT TTC TTT AAC TTA CTA AAA GAA ATT GAT    555
Ile Glu Ile Ser Val His Lys Val Phe Phe Asn Leu Leu Lys Glu Ile Asp
     125                     130                     135

ACC AGT ACC AAA GTT GAT AAT GCT ATG TCA AGA CTG TTG AAG AAG TAT    603
Thr Ser Thr Lys Val Asp Asn Ala Met Ser Arg Leu Leu Lys Lys Tyr
 140                     145                     150         155

GAT GTA TTG TTT GCA CTC TTC AGC AAA TTG GAA AGG ACA TGT GAA CTT    651
Asp Val Leu Phe Ala Leu Phe Ser Lys Leu Glu Arg Thr Cys Glu Leu
         160                     165                     170
```

*FIG. 9B*

| | |
|---|---|
| ATA TAT TTG ACA CAA CCC AGC AGT TCG ATA TCT ACT GAA ATA AAT TCT<br>Ile Tyr Leu Thr Gln Pro Ser Ser Ser Ile Ser Thr Glu Ile Asn Ser<br>175                             180                             185 | 699 |
| GCA TTG GTG CTA AAA GTT TCT TGG ATC ACA TTT TTA GCT AAA GGG<br>Ala Leu Val Leu Lys Val Ser Trp Ile Thr Phe Leu Ala Lys Gly<br>190                         195                          200 | 747 |
| GAA GTA TTA CAA ATG GAA GAT GAT CTG GTG ATT TCA TTT CAG TTA ATG<br>Glu Val Leu Gln Met Glu Asp Asp Leu Val Ile Ser Phe Gln Leu Met<br>205                             210                            215 | 795 |
| CTA TGT GTC CTT GAC TAT TTT ATT AAA CTC TCA CCT CCC ATG TTG CTC<br>Leu Cys Val Leu Asp Tyr Phe Ile Lys Leu Ser Pro Pro Met Leu Leu<br>220                             225                            230               235 | 843 |
| AAA GAA CCA TAT AAA ACA GCT GTT ATA CCC ATT AAT GGT TCA CCT CGA<br>Lys Glu Pro Tyr Lys Thr Ala Val Ile Pro Ile Asn Gly Ser Pro Arg<br>240                             245                            250 | 891 |
| ACA CCC AGG CGA GGT CAG AAC AGG AGT GCA CGG ATA GCA AAA CAA CTA<br>Thr Pro Arg Arg Gly Gln Asn Arg Ser Ala Arg Ile Ala Lys Gln Leu<br>255                             260                            265 | 939 |

Rb 49 (boxed: CGA GGT CAG AAC AGG AGT)

FIG. 9C

```
GAA AAT GAT ACA AGA ATT ATT GAA GTT CTC TGT AAA GAA CAT GAA TGT        987
Glu Asn Asp Thr Arg Ile Ile Glu Val Leu Cys Lys Glu His Glu Cys
270                 275                 280

AAT ATA GAT GAG GTG AAA AAT GTT TAT TTC AAA AAT TTT ATA CCT TTT       1035
Asn Ile Asp Glu Val Lys Asn Val Tyr Phe Lys Asn Phe Ile Pro Phe
285                 290                 295

ATG AAT TCT CTT GGA CTT GTA CTT ACA TCT GTA CTT CCA GAG GTT GAA       1083
Met Asn Ser Leu Gly Leu Val Leu Thr Ser Val Leu Pro Glu Val Glu
300                 305                 310                 315

AAT CTT TCT AAA CGA TAC GAA GAA ATT TAT CTT AAA AAT AAA GAT CTA       1131
Asn Leu Ser Lys Arg Tyr Glu Glu Ile Tyr Leu Lys Asn Lys Asp Leu
        320                 325                 330
                                                    ▲
                                                   BglII

GAT GCA AGA TTA TTT TTG GAT CAT GAT AAA ACT CTT CAG ACT GAT TCT       1179
Asp Ala Arg Leu Phe Leu Asp His Asp Lys Thr Leu Gln Thr Asp Ser
        335                 340                 345
     Fusion Protein
ATA GAC AGT TTT GAA ACA CAG AGA ACA CCA CGA AAA AGT AAC CTT GAT       1227
Ile Asp Ser Phe Glu Thr Gln Arg Thr Pro Arg Lys Ser Asn Leu Asp
350                 355                 360
```

FIG. 9D

```
                                                                              →Rb18
                                                                         GTT ATG   1275
                                                                         ←
                                                                           A
215 →N-terminal
GAA GAG GTG AAT GTA ATT CCT CCA CAC ACT CCA GTT AGG ACT GTT ATG
Glu Glu Val Asn Val Ile Pro Pro His Thr Pro Val Arg Thr Val Met
365                 370                 375                 
                         N-terminal
AAC ACT ATC CAA CAA TTA ATG ATG ATT TTA AAT TCA GCA AGT GAT CAA   1323
Asn Thr Ile Gln Gln Leu Met Met Ile Leu Asn Ser Ala Ser Asp Gln
380                 385                 390                 395
         Rb28
CCT TCA GAA AAT CTG ATT TCC TAT TTT AAC AAC TGC ACA GTG AAT CCA   1371
Pro Ser Glu Asn Leu Ile Ser Tyr Phe Asn Asn Cys Thr Val Asn Pro
                400                 405                 410

AAA GAA AGT ATA CTG AAA AGA GTG AAG GAT ATA GGA TAC ATC TTT AAA   1419
Lys Glu Ser Ile Leu Lys Arg Val Lys Asp Ile Gly Tyr Ile Phe Lys
        415                 420                 425

GAG AAA TTT GCT AAA GCT GTG GGA CAG GGT TGT GTC GAA ATT GGA TCA   1467
Glu Lys Phe Ala Lys Ala Val Gly Gln Gly Cys Val Glu Ile Gly Ser
        430                 435                 440
```

*FIG. 9E*

```
CAG CGA TAC AAA CTT GGA GTT CGC TTG TAT TAC CGA GTA ATG GAA TCC        1515
Gln Arg Tyr Lys Leu Gly Val Arg Leu Tyr Tyr Arg Val Met Glu Ser
        445                 450                 455

ATG CTT AAA TCA GAA GAA CGA TTA TCC ATT CAA AAT TTT AGC AAA            1563
Met Leu Lys Ser Glu Glu Arg Leu Ser Ile Gln Asn Phe Ser Lys
        460                 465                 470             475

CTT CTG AAT GAC AAC ATT TTT CAT ATG TCT TTA TTG GCG TGC GCT CTT        1611
Leu Leu Asn Asp Asn Ile Phe His Met Ser Leu Leu Ala Cys Ala Leu
            480                 485                 490

GAG GTT GTA ATG GCC ACA TAT AGC AGA AGT ACA TCT CAG AAT CTT GAT        1659
Glu Val Val Met Ala Thr Tyr Ser Arg Ser Thr Ser Gln Asn Leu Asp
        495                 500                 505

→EVE4    ←Rb13
TCT GGA ACA GAT TTG TCT TTC CCA TGG ATT CTG AAT GTG CTT AAT TTA        1707
Ser Gly Thr Asp Leu Ser Phe Pro Trp Ile Leu Asn Val Leu Asn Leu
        510                 515                 520
```

*FIG. 9F*

```
AAA GCC TTT GAT TTT TAC AAA GTG ATC GAA AGT TTT ATC AAA GCA GAA      1755
Lys Ala Phe Asp Phe Tyr Lys Val Ile Glu Ser Phe Ile Lys Ala Glu
525                     530                     535

GGC AAC TTG ACA AGA GAA ATG ATA AAA CAT TTA GAA CGA TGT GAA CAT      1803
Gly Asn Leu Thr Arg Glu Met Ile Lys His Leu Glu Arg Cys Glu His
540                     545                     550            555
                                                    →Rb17
CGA ATC ATG GAA TCC CTT GCA TGG CTC TCA GAT TCA GAT CAC CTT GAA      1851
Arg Ile Met Glu Ser Leu Ala Trp Leu Ser Asp Ser Pro Leu Phe Asp
                560                     565                     570

CTT ATT AAA CAA TCA AAG GAC CGA GAA GGA CCA ACT GAT CAC CTT GAA      1899
Leu Ile Lys Gln Ser Lys Asp Arg Glu Gly Pro Thr Asp His Leu Glu
        575                     580                     585
                                                              Rb14
TCT GCT TGT CCT CTT AAT CTT CTC CAG AAT CTT AGA TCT CCA AAT CAC ACT GCA GCA      1947
Ser Ala Cys Pro Leu Asn Leu Leu Gln Asn Leu Arg Ser Pro Val Asn His Thr Ala Ala
590                     595                     600
                                        ↱
GAT ATG TAT CTT TCT CCT GTA AGA TCT CCA AAG AAA AAA GGT TCA ACT      1995
Asp Met Tyr Leu Ser Pro Val Arg Ser Pro Lys Lys Lys Gly Ser Thr
605                     610                     615
↳          Fusion Protein→  BglII
```

FIG. 9G

```
ACG CGT GTA AAT TCT ACT GCA AAT GCA GAG ACA CAA GCA ACC TCA GCC    2043
Thr Arg Val Asn Ser Thr Ala Asn Ala Glu Thr Gln Ala Thr Ser Ala
620                     625                     630             635

TTC CAG ACC CAG AAG CCA TTG AAA TCT CTT TCA CTG TTT TAT            2091
Phe Gln Thr Gln Lys Pro Leu Lys Ser Leu Ser Leu Phe Tyr
                640                     645             650

AAA AAA GTG TAT CGG CTA GCC TAT CTC CGG CTA AAT ACA CTT TGT GAA    2139
Lys Lys Val Tyr Arg Leu Ala Tyr Leu Arg Leu Asn Thr Leu Cys Glu
            655                     660                     665 667

CGC CTT CTG TCT GAG CAC CCA GAA TTA GAA CAT ATC ATC TGG ACC CTT    2187
Arg Leu Leu Ser Glu His Pro Glu Leu Glu His Ile Ile Trp Thr Leu
    670                     675                     680
 finger domain TTC CAG CAC ACC CTG CAG AAT GAG TAT GAA CTC ATG AGA GAC AGG CAT    2235
Phe Gln His Thr Leu Gln Asn Glu Tyr Glu Leu Met Arg Asp Arg His
685                     690                     695
                     ↓ 692
                 finger domain
```

*FIG. 9H*

```
TTG GAC CAA ATT ATG ATG TGT TCC ATG TAT GGC ATA TGC AAA GTG AAG   2283
Leu Asp Gln Ile Met Met Cys Ser Met Tyr Gly Ile Cys Lys Val Lys
700                   705          Rb8         710            715
          FH7

AAT ATA GAC CTT AAA TTC AAA ATC ATT GTA ACA GCA TAC AAG GAT CTT   2331
Asn Ile Asp Leu Lys Phe Lys Ile Ile Val Thr Ala Tyr Lys Asp Leu
            720                 725                 730

CCT CAT GCT GTT CAG GAG ACA TTC AAA CGT GTT TTG ATC AAA GAA GAG   2379
Pro His Ala Val Gln Glu Thr Phe Lys Arg Val Leu Ile Lys Glu Glu
            735                 740                 745

GAG TAT GAT TCT ATT ATA GTA TTC TAT AAC TCG GTC TTC ATG CAG AGA   2427
Glu Tyr Asp Ser Ile Ile Val Phe Tyr Asn Ser Val Phe Met Gln Arg
            750                 755                 760

CTG AAA ACA AAT ATT TTG CAG TAT GCT TCC ACC AGG CCC CCT ACC TTG   2475
Leu Lys Thr Asn Ile Leu Gln Tyr Ala Ser Thr Arg Pro Pro Thr Leu
765                 770                 775
```

*FIG. 9I*

| | | | | | | | | | | | | | | | | |
|---|---|---|---|---|---|---|---|---|---|---|---|---|---|---|---|---|
| TCA | CCA | ATA | CCT | CAC | ATT | CCT | CGA | AGC | CCT | TAC | AAG | TTT | CCT | AGT | TCA | 2523 |
| Ser | Pro | Ile | Pro | His | Ile | Pro | Arg | Ser | Pro | Tyr | Lys | Phe | Pro | Ser | Ser | |
| 780 | | | | | 785 | | | | | 790 | | | | | 795 | |
| CCC | TTA | CGG | ATT | CCT | GGA | GGG | AAC | ATC | TAT | ATT | TCA | CCC | CTG | AAG | AGT | 2571 |
| Pro | Leu | Arg | Ile | Pro | Gly | Gly | Asn | Ile | Tyr | Ile | Ser | Pro | Leu | Lys | Ser | |
| | | | | 800 | | | | | 805 | | | | | 810 | | |
| CCA | TAT | AAA | ATT | TCA | GAA | GGT | CTG | CCA | ACA | CCA | ACA | AAA | ATG | ACT | CCA | 2619 |
| Pro | Tyr | Lys | Ile | Ser | Glu | Gly | Leu | Pro | Thr | Pro | Thr | Lys | Met | Thr | Pro | |
| | | | 815 | | | | | 820 | | | | | 825 | | | |
| AGA | TCA | AGA | ATC | TTA | GTA | TCA | ATT | GGT | GAA | TCA | TTC | GGG | ACT | TCT | GAG | 2667 |
| Arg | Ser | Arg | Ile | Leu | Val | Ser | Ile | Gly | Glu | Ser | Phe | Gly | Thr | Ser | Glu | |
| | | →Rb55 | | | | | | | | | | 840 | | | | |
| | | | 830 | | | | | 835 | | | | Rb56▼ | | | | |
| AAG | TTC | CAG | AAA | ATA | AAT | CAG | ATG | GTA | TGT | AAC | AGC | GAC | CGT | GTG | CTC | 2715 |
| Lys | Phe | Gln | Lys | Ile | Asn | Gln | Met | Val | Cys | Asn | Ser | Asp | Arg | Val | Leu | |
| | | | 845 | | | | | 850 | | | | | 855 | | | |
| AAA | AGA | AGT | GCT | GAA | GGA | AGC | AAC | CCT | CCT | AAA | CCA | CTG | AAA | AAA | CTA | 2763 |
| Lys | Arg | Ser | Ala | Glu | Gly | Ser | Asn | Pro | Pro | Lys | Pro | Leu | Lys | Lys | Leu | |
| | | 860 | | | | | 865 | | | | | 870 | | | 875 | |

FIG. 9J

```
CGC TTT GAT ATT GAA GGA TCA GAT GAA GCA GAT GGA AGT AAA CAT CTC    2811
Arg Phe Asp Ile Glu Gly Ser Asp Glu Ala Asp Gly Ser Lys His Leu
            880                 885                 890

CCA GGA GAG TCC AAA TTT CAG CAG AAA CTG GCA GAA ATG ACT TCT ACT    2859
Pro Gly Glu Ser Lys Phe Gln Gln Lys Leu Ala Glu Met Thr Ser Thr
            895                 900                 905

CGA ACA CGA ATG CAA ATG AAA CAG AAA ATG AAT GAT AGC ATG GAT ACC TCA    2907
Arg Thr Arg Met Gln Met Lys Gln Lys Met Asn Asp Ser Met Asp Thr Ser
            910                 915                 920
                                                        C-Terminal Peptide
                                              C│917
                                                ↑

AAC AAG GAA GAG AAA TGAGGATCTC AGGACCTGG TGGACACTGT GTACACCTCT    2962
Asn Lys Glu Glu Lys
        925
        ↑
      928B

GGATTCATTG TCTCTCACAG ATGTGACTG TAT    2995
                 ──FH3──→
```

FIG. 9K

METHOD OF USING AN ADENOVIRAL VECTOR ENCODING A RETINOBLASTOMA PROTEIN TO TREAT HYPERPROLIFERATING CELLS

CROSS REFERENCE TO RELATED APPLICATIONS

This application is a continuation-in-part patent application of the following U.S. patent applications: Retinoblastoma Gene Cancer Suppressing and Regulator, Ser. No. 07/951,947, filed Sep. 28, 1992, abandoned; Products and Methods for Controlling the Suppression of the Neoplastic Phenotype, Ser. No. 08/276,041, filed Jul. 14, 1994 now abandoned which in turn is a continuation of Ser. No. 07/764,714 filed Sep. 24, 1991, abandoned, which in turn is a continuation of Ser. No. 07/265,829, filed Oct. 31, 1988, abandoned; ppRB$^{110}$—Nuclear Phosphoprotein—The Retinoblastoma Susceptibility Gene Product, Ser. No. 08/225,099, filed Apr. 8, 1994, issued as U.S. Pat. No. 5,578,701 on Nov. 26, 1996, which in turn is a continuation of Ser. No. 08/079,207, filed Jun. 17, 1993, abandoned, which in turn is a continuation of Ser. No. 07/914,039, filed Jul. 14, 1992, which in turn is a continuation of Ser. No. 07/550,877, filed Jul. 11, 1990, which in turn is a divisional of Ser. No. 08/098,612, filed Sep. 17, 1987, issued as U.S. Pat. No. 4,942,123 on Jul. 17, 1990; Method for Producing Gene Protein Products, Ser. No. 08/058,784, filed May 7, 1993, issued as U.S. Pat. No. 6,051,396 on Apr. 18, 2000, which in turn is a continuation of Ser. No. 07/906,008, filed Jun. 26, 1992, abandoned, which in turn is a continuation of Ser. No. 07/553,905, filed Jul. 16, 1990, abandoned; and Therapeutic Use of the Retinoblastoma Susceptibility Gene Product, Ser. No. 08/306,513, filed Sep. 13, 1994, issued as U.S. Pat. No. 5,851,991 on Dec. 22, 1998, which in turn is a continuation-in-part of Ser. No. 08/121,108, filed Sep. 13, 1993, abandoned, Ser. No. 07/956,472, filed Oct. 2, 1992, abandoned, and Ser. No. 08/126,810, filed Sep. 24, 1993, which in turn is a continuation of Ser. No. 07/778,510, filed Oct. 17, 1991 abandoned. The foregoing parent patent applications are incorporated by reference as if fully set forth herein.

This invention was made with Government support under Grant No. EY 05758 with the National Institute of Health and the University of California. The Government has certain rights in this invention.

TECHNICAL FIELD

This invention relates in general to the control of cell cycle progression and it more particularly relates to compositions and methods for regulating cell cycle progression to suppress cellular proliferative diseases, including local proliferation of cells (benign diseases) and malignant processes, i.e. cancer and tumorigenesis.

It is well recognized that in the development of higher organisms, such as animals and humans, orderly cell cycle progression is a critical factor. Because of such progression, ordered and systematic cell differentiation occurs so that, ultimately from a single undifferentiated cell, a highly structured organism, having a variety of specialized tissues, develops. In general, physiologically normal cell cycle progression is very important to the organism, not only during the stages of early growth, but through the entire life of the organism. Thus, even after the organism has reached maturity, normal cycle progression is still a very important aspect of health. This, for example, can be clearly seen in the importance of proper cellular regulation in the blood forming and reproductive organs.

Normal cell cycle progression may fail resulting in inappropriate local proliferation of cells. Pathological conditions associated with uncontrolled progression of cells through the cell cycle producing local hyperproliferation include benign neurofibromas, blindness due to inappropriate growth of blood vessels in the eye (a vasoproliferative disease), psoriasis, atherosclerosis (vasoproliferative), and other similar proliferative diseases throughout the body.

Currently, treatment of these local cellular proliferative diseases includes tissue removal by, for example, surgery or radiation. Such treatments generally result in damage to normal tissues as well as removal of the pathological tissues. Local treatments such as laser or local cryotherapy are rarely successful.

Under certain circumstances, normal cell cycle progression fails, often with catastrophic effects for the organism. Such a failure is seen, for example, in the various forms of cancer where, because of an unchecked, and uncontrolled, progression of cells through the cell cycle, from the completion of mitosis through interphase and back into mitosis, tumorigenesis becomes, in many cases, a life threatening event. Thus, a restraint on uncontrolled cell cycle progression is sometimes attempted in an effort to treat or control the tumorigenic condition.

Under current conditions, where tumorigenesis has developed, drastic treatment measures, such as radiation therapy and chemotherapy, are employed. Both of these modalities are very expensive and, in some cases, very damaging to the organism. Chemotherapy, for example, can cause the death of a patient and when chemotherapy is successful in controlling tumorigenesis, it may have long term adverse effects on the body. Such, an adverse effect may result in premature heart problems for the patient. Thus, while conventional therapeutic methods, such as radiation and chemotherapy, serve a useful purpose in destroying certain uncontrolled cells, they also produce the unwanted effects of destroying useful cells and weakening organ systems.

In view of the foregoing, it would be highly desirable to have techniques and compositions for regulating unwanted cell progression, such as in local hyperproliferative disorders and tumorigenesis, while maintaining cell viability. In addition, it would be further very highly desirable if such techniques and compositions produce little or no adverse effects on the cell and, halt the development of cellular proliferative disorders or tumorigenesis without causing irreversible changes at the cellular level.

A significant advantage of such novel techniques and compositions, in the case of tumorigenesis, would be the possibility of regulating unwanted cell proliferation for enough time for other cancer treating procedures to be applied. In the case of local hyperproliferative diseases, specific targeted therapy would control the local cellular proliferation while leaving the surrounding cells unaffected. Thus, the use of such techniques could reduce or eliminate the ravaging effects of conventional radiation and chemotherapeutic treatments, while arresting tumorigenesis. Hence, the patient would retain strength and vigor so that conventional techniques, such as surgery, could be more safely utilized.

DISCLOSURE OF INVENTION

It is an object of the present invention to provide cell cycle controlling compositions and method of using the same for controlling the progression of the cell cycle in living organisms.

It is a further object of the present invention to provide a safe and effective method and composition for reversibly arresting cell cycle progression in organisms.

It is a still further object of the present invention to provide a technique which may be used in combination with therapeutic methods to arrest tumorigenesis in organisms.

It is another object of the present invention to provide the means and methods to control or suppress local cellular proliferative diseases.

The present invention includes a method and compositions for controlling cell cycle progression, by introducing into a cell to be controlled a cell cycle regulating composition. The composition is selected from the group consisting of a gene protein product and a fragment of the protein, or the gene encoding the protein product, to alter reversibly the cell cycle progression of the cell while maintaining its viability. The gene encoding the protein when delivered by a vector has been found to have the unexpected and surprising effect of controlling cell cycle progression. The protein fragments have been found to have the unexpected and surprising characteristic of being soluble in low concentration of glycerol, thereby enhancing their value in pharmaceutical applications.

An advantage of the present invention is that cell cycle progression can be reversibly arrested in a convenient and safe manner, without insult to the organism. Thus, local cellular proliferation or tumorigenesis may, for example, be controlled.

A further advantage of the present invention is that the alternative compositions utilized for cell cycle progression control are readily obtainable.

A still further advantage of the present invention is the fact that the compositions utilized herein possess little or no toxic effects on healthy cells, and may be used in conjunction with other methods of treatment for inhibiting cellular proliferation whether it be benign or neoplastic proliferation.

An even still further advantage of the present invention is the fact that the compositions and techniques are compatible for use with the regulatory regimens and are physiologically compatible with other methods and devices for regulating certain physiological processes of the body such as blood cell production and gamete production.

BRIEF DESCRIPTION OF DRAWINGS

The above mentioned and other objects and features of this invention and the manner of attaining them will become apparent, and the invention itself will be best understood by reference to the following description of the embodiment of the invention in conjunction with the accompanying drawings, wherein:

FIGS. 7A–K depict the nucleotide sequence of the retinoblastoma gene and the amino acid sequence of the RB protein;

Figure 8:
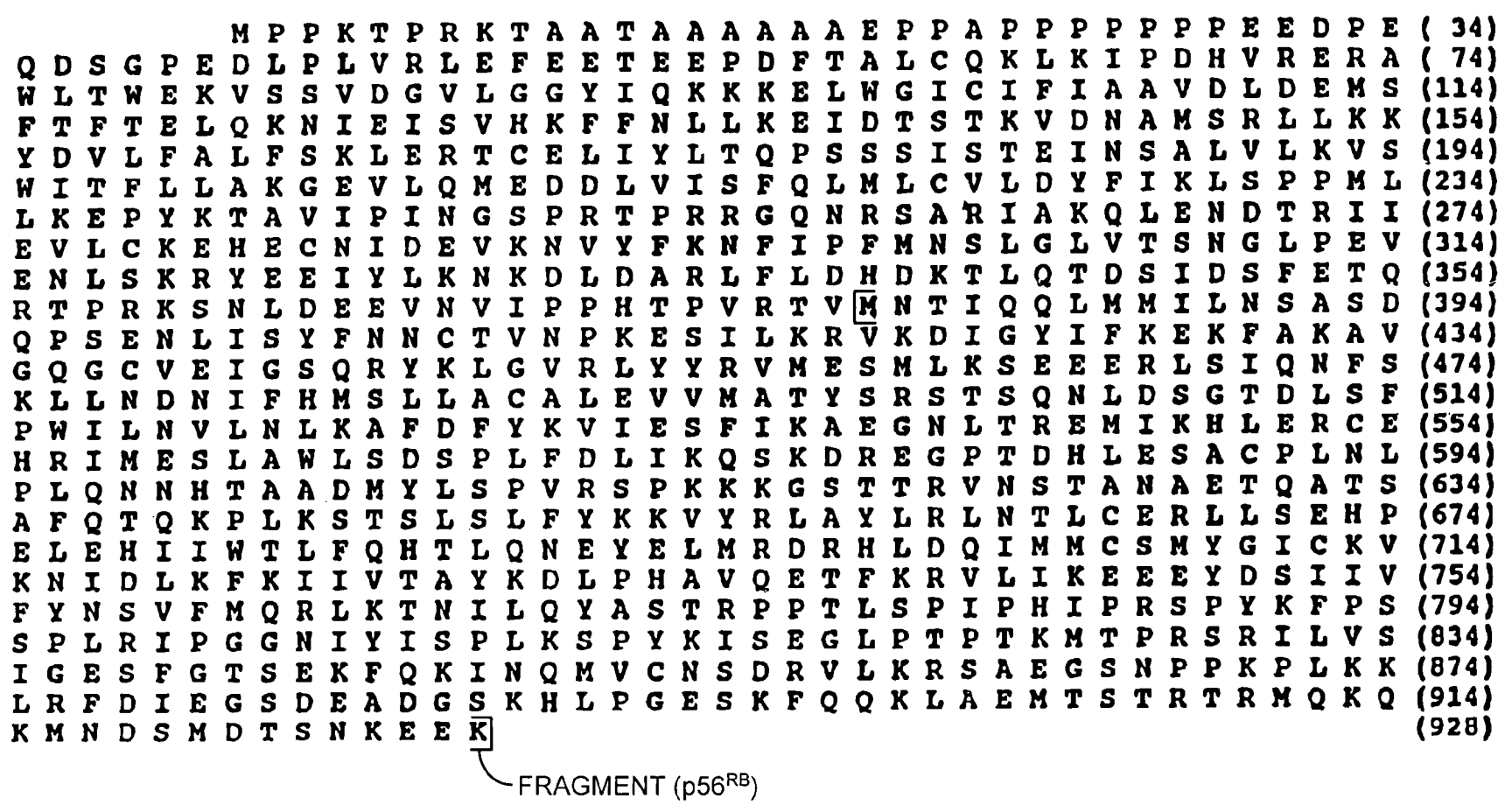

FIG. 8 depicts the amino acid sequence of the RB protein (SEQ ID NO:2); and the truncated $p56^{RB}$ amino acid sequence.

FIGS. 9A–K depict the nucleotide sequence of the retinoblastoma gene and the amino acid sequence of the RB gene product and, in addition, depicts the $p56^{RB}$ portion of the RB gene and the RB protein.

FIG. 15A shows [³H]thymidine incorporation and FIGS. 15B–C show lactate dehydrogenase release in 5637 cells treated with vector constructs ACBRB and/or ACN56 as compared to control vector ACN.

BEST MODE FOR CARRYING OUT THE INVENTION

Figure 1:
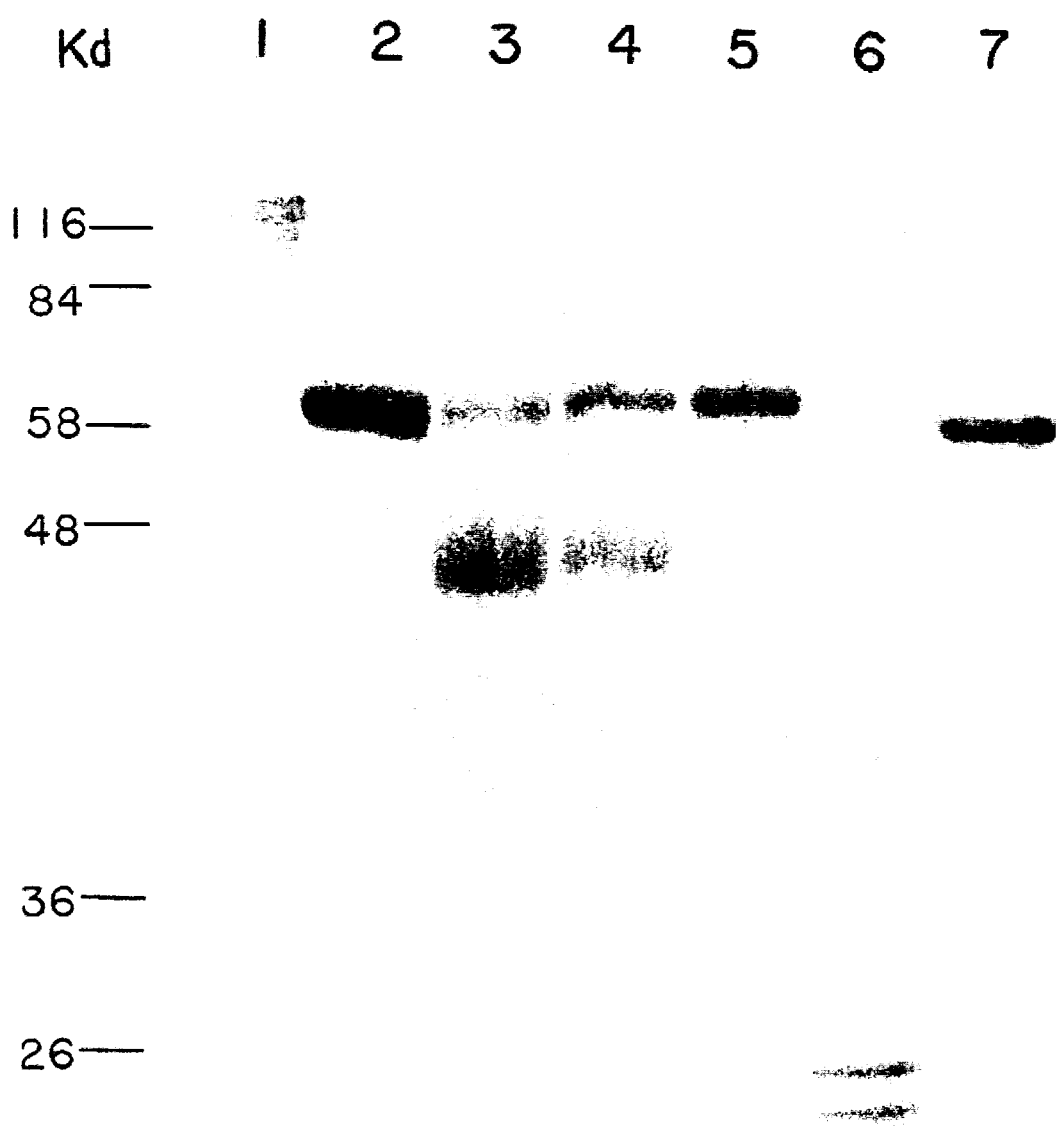
FIG. 1 depicts SDS-PAGE analysis of the concentration and purity of protein preparations used for microinjection.

It is generally recognized that, after mitosis of a somatic cell is completed, at the end of telophase, the cell enters into an interphase which, depending on a variety of factors, may be of short duration or last for a long period of time. Thus, for example, after cell differentiation and development of nerve tissue, the nerve cells may have a very long interphase. Conventionally, cellular interphase may be regarded as having three stages: G1, in which cell growth occurs without DNA replication, S phase, in which DNA replication occurs, and G2, in which DNA replication has been completed and the cell prepares for division. As hereinafter described in greater detail, certain gene protein products, or fragments thereof, or the gene encoding such cell cycle regulating proteins, have the capacity for controlling progression through the cell cycle by stopping reversibly the progression at G1. According to the present invention, cell cycle controlling compositions were introduced into cells to cause a reversible alteration of the cell cycle progression, while maintaining cell viability. After a certain time, when the compositions degraded sufficiently within the cell, the cell cycle has been observed to be reinstated with the cell progressing toward subsequent stages of interphase.

With regard to pathological conditions in an organism, such as benign cellular proliferative diseases or tumorigenesis, there is a manifestation of unwanted cell cycle acceleration in some cells. As more fully discussed below, cancer suppressor gene encoding a cell cycle regulating protein or cancer suppressor gene protein products, such as the p56$^{RB}$ protein, or a fragment thereof, were utilized to arrest Saos-2 osteosarcoma cells in the G1 stage of interphase. It has been found that the administration of the gene encoding the protein or the protein itself to the cells had no toxic effect on the cells, and was reversible.

As is known to those of skill in the art, the term "protein" means a linear polymer of amino acids joined in a specific sequence by peptide bonds. As used herein, the term "amino acid" refers to either the D or L stereoisomer form of the amino acid, unless otherwise specifically designated. Also encompassed within the scope of this invention are equivalent proteins or equivalent peptides, e.g., having the biological activity of purified p56$^{RB}$ "Equivalent proteins" and "equivalent polypeptides" refer to compounds that depart from the linear sequence of p56$^{RB}$, but which have amino acid substitutions that do not change its biological activity. These equivalents can differ from the native sequences by the replacement of one or more amino acids with related amino acids, for example, similarly charged amino acids, or the substitution or modification of side chains or functional groups.

A pharmaceutically acceptable carrier can contain a physiologically acceptable compound that acts, for example, to stabilize the composition or to increase or decrease the absorption of the agent. A physiologically acceptable compound can include, for example, carbohydrates, such as glucose, sucrose or dextrans, antioxidants, such as ascorbic acid or glutathione, chelating agents, low molecular weight proteins or other stabilizers or excipients. Other physiologically acceptable compounds include wetting agents, emulsifying agents, dispersing agents or preservatives, which are particularly useful for preventing the growth or action of microorganisms. Various preservatives are well known and include, for example, phenol and ascorbic acid. One skilled in the art would know that the choice of a pharmaceutically acceptable carrier, including a physiologically acceptable compound, depends, for example, on the route of administration of the polypeptide and on the particular physiochemical characteristics of the specific polypeptide. For example, a physiologically acceptable compound such as aluminum monosterate or gelatin is particularly useful as a delaying agent, which prolongs the rate of absorption of a pharmaceutical composition administered to a subject. Further examples of carriers, stabilizers or adjuvants can be found in Martin, *Remington's Pharm. Sci.*, 15th Ed. (Mack Publ. Co., Easton, 1975), incorporated herein by reference. The pharmaceutical composition also can be incorporated, if desired, into liposomes, microspheres or other polymer matrices (Gregoriadis, *Liposome Technology*, Vol. 1 (CRC Press, Boca Raton, Fla. 1984), which is incorporated herein by reference). Liposomes, for example, which consist of phospholipids or other lipids, are nontoxic, physiologically acceptable and metabolizable carriers that are relatively simple to make and administer.

As used herein, "pharmaceutical composition" refers to any of the compositions of matter described herein in combination with one or more of the above pharmaceutically acceptable carriers. The compositions can then be administered therapeutically or prophylactically. They can be contacted with the host cell in vivo, ex vivo, or in vitro, in an effective amount. in vitro and ex vivo means of contacting host cells are provided below. When practiced in vivo, methods of administering a pharmaceutical composition containing the vector of this invention are well known in the art and include, but are not limited to, administration orally, intra-tumorally, intravenously, intramuscularly or intraperitoneal. Administration can be effected continuously or intermittently and will vary with the subject and the condition to be treated, e.g., as is the case with other therapeutic compositions (Landmann et al., "Prolonged Interferon-γ Application by Subcutaneous Infusion in Cancer Patients: Differential Response of Serum CD14, Neopterin, and Monocyte HLA Class I and II Antigens." *J. Interferon Res.* 12 (2):103–111 (1992); Aulitzky et al., "Recombinant Tumour Necrosis Factor Alpha Administered Subcutaneously or Intramuscularly for Treatment of Advanced Malignant Disease: a Phase I Trial." *Eur. J. Cancer* 27 (4):462–467 (1991); Lantz et al., *Cytokine* 2 (6):402–406 (1990); Supersaxo et al., "Recombinant Human Interferon Alpha-2a: Delivery to Lymphoid Tissue by Selected Modes of Application." 5 (8):472–476 (1988); Demetri et al., "A Phase I Trial of Recombinant Human Tumor Necrosis Factor and Interferon-Gamma: Effects of Combination Cytokine Administration In Vivo." *J. Olin. Oncol.* 7 (10):1545–1553 (1989); and LeMaistre et al., "Therapeutic effects of genetically engineered toxin (DAB$_{486}$IL-2) in patient with chronic lymphocytic leukaemia." *Lancet* 337:1124–1125 (1991)).

The recombinant adenoviruses expressing p56$^{RB}$, as described above, may efficiently inhibit DNA synthesis and inhibit cellular proliferation and suppress the growth of a broad range of human tumor cell types. Furthermore, recombinant adenoviruses can express in an established tumor within an organism without relying on direct injection into the tumor or prior ex vivo treatment of the cancer cells. The $p56^{RB}$ expressed is functional and may inhibit cellular proliferation and suppresses tumor growth in vivo.

Thus, the vectors containing $p56^{RB}$ of this invention are particularly suited for gene therapy. Accordingly, methods of $p56^{RB}$ gene therapy utilizing these vectors are within the scope of this invention. The vector containing $p56^{RB}$ is purified and then an effective amount is administered in vivo or ex vivo into the subject. Methods of gene therapy are well known in the art, see, for example, Larrick, J. W. and Burck, K. L., *Gene Therapy: Application of Molecular Biology*, Elsevier Science Publishing Co., Inc., New York, N.Y. (1991) and Kreigler, M., *Gene Transfer an Expression: A Laboratory Manual*, W.H. Freeman and Company, New York (1990). "Subject" means any animal, mammal, rat, murine, bovine, porcine, equine, canine, feline or human patient. The vector coding for the $p56^{RB}$ protein is useful to treat or reduce hyperproliferative cells in a subject, to inhibit tumor proliferation in a subject or to ameliorate a particular related pathology. Pathologic hyperproliferative cells are characteristic of the following disease states: thyroid hyperplasia—Grave's Disease, psoriasis, benign prostatic hypertrophy, Li-Fraumeni syndrome (including breast cancer), sarcomas and other neoplasms, bladder cancer, colon cancer, lung cancer, and various leukemias and lymphomas. Examples of non-pathologic hyperproliferative cells are found, for instance, in mammary ductal epithelial cells during development of lactation and also in cells associated with wound repair. Pathologic hyperproliferative cells characteristically exhibit loss of contact inhibition and a decline in their ability to selectively adhere which implies a change in the surface properties of the cell and a further breakdown in intercellular communication. These changes include stimulation to divide and the ability to secrete proteolytic enzymes.

As used herein, the term "effective amount" is intended to mean the amount of vector or anti-cancer or anti-hyperproliferative protein which achieves a positive outcome on controlling cell proliferation. For example, one dose contains from about $10^8$ to about $10^{13}$ infectious units. A typical course of treatment would be one such dose a day over a period of five days. An effective amount in the case of the $p56^{RB}$ protein is for example in the range of 0.1 mg/kg to 10 mg/kg. An effective amount will vary depending on the pathology or condition to be treated, by the patient and his status, and other factors well known to those of skill in the art. Effective amounts are determined by those of skill in the art.

Also within the scope of this invention is a method of ameliorating a pathology characterized by hyperproliferative cells or genetic defect of RB protein in a subject by administering to the subject an effective amount of a vector described above containing DNA encoding the $p56^{RB}$ protein having the ability to ameliorate the pathology, under suitable conditions.

A method of tumor-specific delivery of $p56^{RB}$ DNA suppressor gene is accomplished by contacting target tissue in an animal with an effective amount of the recombinant adenoviral expression vector containing the $p56^{RB}$ encoding DNA of this invention. "Contacting" is intended to encompass any delivery method for the efficient transfer of the vector containing the $p56^{RB}$ DNA such as intra-tumoral injection.

The term "pathologically proliferating cell" is intended to include but is not limited to cells having the capacity for autonomous growth, i.e., existing and reproducing independently of normal regulatory mechanisms. These cells are pathologic because they deviate from normal cells, whether or not associated with a diseased state. Examples of such cells include, but are not limited to, a retinal cell, a prostate cell, a psoriatic cell, a thyroid cell, a breast cell, a colon cell, a lung cell, a sarcoma cell, a leukemia cell, or a lymphoma cell. Also intended are tumor cells characteristic of cancers such as retinoblastoma, osteosarcoma, fibrosarcoma, glioblastoma, breast cancer, lung cancer, transitional cell carcinoma of bladder, small cell lung carcinoma, non-small cell lung carcinoma, renal cell carcinoma, or acoustic neuroma, for example.

When the contacting is effected in vivo, the $p56^{RB}$ polypeptide or protein is first mixed with a pharmaceutically acceptable carrier for administration. A "pharmaceutically acceptable carrier" is intended to include, but not be limited to, any of the standard pharmaceutical carriers, such as phosphate buffered saline, water, glycerol, mannitol, sucrose, human serum albumin, Tween 80, Tris, sodium carbonate and also emulsions, such as oil/water emulsions and various types of wetting agents.

As used herein, the term "administering" for in vivo protein therapy purposes means providing the subject with an effective amount of the $p56^{RB}$ polypeptide or protein, in order to prevent or inhibit proliferation of the target cell or growth of the tumor. Methods of administering pharmaceutical compositions are well known to those of skill in the art and include, but are not limited to, intratumoral injection, oral administration, intravenous administration or parenteral administration. Administration can be effected continuously or intermittently throughout the course of treatment. Methods of determining the most effective means and dosage are well known to those of skill in the art and will vary with the $p56^{RB}$ protein or polypeptide used for therapy, the purpose of the therapy, the hyperproliferative cell or tumor being treated, and the subject being treated. As an example, a suitable dosage range is from about 0.1 mg/kg/body weight to about 10 mg/kg/body weight.

In the examples discussed below, the following experimental procedures were followed.

Cell Cycle

Saos-2 cells, an osteosarcoma cell line, were obtained from American Type Culture Collection. SR-40, which stably expresses exogenous, wild-type RB protein, was derived from Saos-2 by single cell cloning after infection with a retrovirus carrying the RB gene. (Huang et al., *Science* 242, 1563–1566 (1988)). African Green monkey kidney cell lines CV-1 and COS-7 were also obtained from American Type Culture Collection. COS-7 was derived from CV-1 by transformation with an origin-defective SV-40 (Gluzman, Y., *Cell* (23) 175–182 (1981)). All the cells were cultured in Dulbecco's modified Eagle's medium plus 10% fetal calf serum as recommended.

Synchronization of Cells

Cells were synchronized at the G1/S boundary by isoleucine starvation for 36 hours and then incubated in complete medium supplemented with either aphidicolin or hydroxyurea (both from Sigma) for an additional 12 or 16 hours respectively. (Heintz, H. H. and Hamlin, J. L., Proc. Natl. Acad. Sci. USA 79:4083–4087 (1982)). Cells were released from G1/S block by washing three times with phosphate buffered saline (PBS), and re-feeding with complete media. Metaphase arrested cells were collected after an 8 to 12 hour treatment with 0.04 µg/ml nocodazole (Sigma) as previously described. (Zieve et al., Exp. Cell Res. 126:397–405 (1980)). To increase the yield of mitotic cells, cells were first arrested at the G1/S boundary by a 12-hour treatment with aphidicolin. Six hours after the removal of aphidicolin, nocodazole was added to the medium. Mitotic cells were collected by gentle washing and shaking and were then replaced onto 35 mm dishes. Six hours after seeding, the unattached cells were washed away and cells were injected at various times thereafter.

Protein Preparation $p56^{RB}$ is the C-terminal half of the RB protein and contains both regions essential for SV40 T-antigen binding. It is produced in $E.\ coli$ from a T7 RNA polymerase expression system. (Huang et al., $Nature$ 350:160–162 (1991)). $p110^{RB}$ is produced in insect cells by the recombinant baculovirus technique. (Wang et al., $Cell\ Growth\ \&\ Differ.$ L:429–437 (1990)). Both proteins were purified to homogeneity by conventional chromatography. Histone H1 and Rabbit anti-goat IgG were purchased from Boehringer Mannheim and Vector laboratories, respectively. Antibodies 0.495, 0.47 and R2 were concentrated in microinjection buffer to an approximate concentration of 1 mg/ml. The T-antigen and p53 peptides were the gift of Nicholas Lin. These antibodies are described in Huang et al. ($EMBO\ J.$, 9:1815–1822 (1990)). The T peptide comprises amino acids 101–118, and was dissolved in microinjection buffer at 1 mM or 5 mM. (Ludlow et al., $Cell$ 56:57–65 (1989)). The mutant T peptide contains a lysine to aspartic acid substitution and was used at 5 mM. Ludlow, J. W., deCaprio, J. A., Huang, C.-M., Lee, W.-H., Paucha, E. and Livingston, D. M. (1989) Cell 56, 57-65. The p53 peptide was dissolved in microinjection buffer at 5 mM. Protein preparations, except the full-length RB protein, were concentrated in an injection buffer containing 20 mM Tris, pH 7.4; 0.1 mM EDTA; 10 mM KC1; 1 mM 2-mercaptoethanol and 2% glycerol using the Centricon 30 micro-concentrator (Amicon). $p110^{RB}$ was kept in a buffer containing 10% glycerol to reduce aggregation.

Protein preparations were analyzed by SDS-PAGE using standard techniques. Injections were performed directly on cells growing on 35 mm culture dishes using an Eppendorf micromanipulator and microinjector with femtotip capillary micropipets. Injection pressure was typically set between 50–100 hPa with an injection time of 0.3–0.5 seconds. It was estimated that the protein preparations were diluted approximately 20 to 50-fold upon injection. Assuming a typical cell volume of 50–100 picoliters and a $p56^{RB}$ concentration of 0.5–1 milligram per milliliter, about 5–50 million molecules were injected per cell.

After injection, the growth media was supplemented with bromodeoxyuridine (BrdU) (Amersham) according to manufacturer's recommendations. Following the appropriate labeling period, media was removed and cells were washed 3× with PBS. Cells were then fixed by incubation with ice-cold, absolute methanol for 30 minutes. After re-hydration by washing with PBS, specimens were incubated with a mouse monoclonal antibody directed against BrdU (Amersham) for one hour at room temperature. After washing 3× with PBS, a fluorescein conjugated anti-mouse antibody (Amersham) was added and incubation was continued for an additional hour at room temperature. The anti-mouse antibody was removed by washing 3× with PBS, and the specimens were incubated with Texas Red conjugated streptavidin (Amersham). The streptavidin bound to the biotinylated rabbit α-goat antibodies co-injected with all protein preparations and thus served as a cytoplasmic marker for injected cells. After a final wash, a solution composed of equal volumes of glycerol and PBS was added and the specimens were covered with a glass coverslip. Specimens were examined under a fluorescent microscope with Texas Red and Fluorescein filters.

The following examples demonstrate the experimental results achieved after introduction of gene product proteins into tumor cell lines. The capacity of the proteins, or fragments thereof to arrest cell cycle progression in G1 has been demonstrated. In addition, the examples demonstrate that the effect of the blocking occurs only when the protein is administered during the $G_1$ phase and that the blocked cell cycle progression can be relieved by SV40 T antigen.

In certain specific examples, the RB gene product was used to arrest the cell cycle progression wherein an Saos-2 osteosarcoma cell line was treated with the RB protein or a fragment thereof. It was discovered that cell cycle progression was arrested in G1 and that this progression is reversible.

In the following examples, when the retinoblastoma gene, RB gene, p110 gene, or $p110^{RB}$ gene is referred to, it is intended to mean the full length sequence of SEQ ID NO: 1. When the retinoblastoma protein, RB protein, p110 protein, or $p110^{RB}$ protein are referred to, it is intended to mean the amino acid sequence depicted in SEQ ID NO: 2. When the p56 gene is referred to it is intended to mean nucleotides 1273–2922 of SEQ ID NO: 1. When the p56 protein or $p56^{RB}$ is referred to, it is intended to mean amino acids 379–928 of SEQ ID NO: 2. When the nucleotides encoding the C terminal peptide is referred to, it is intended to mean nucleotides 2887–2992 of SEQ ID NO: 1. When the C terminal peptide is referred to, it is intended to mean amino acids 917–928 of SEQ ID NO: 2.

Single-letter abbreviations in the drawings for the amino acid residues are: A, Alanine; C, Cysteine; D, Aspartic acid; E, Glutamic acid; F, Phenylalanine; G, Glycine; H, Histidine; I, Isoleucine; K, Lysine; L, Leucine; M, Methionine; N, Asparagine, P, Proline; Q, Glutamine; R, Arginine; S, Serine; T, Threonine; V, Valine; W, Tryptophan; and Y, Tyrosine.

EXAMPLE I

Introduction of RB Proteins into Human Osteosarcoma Saos-2 Cells by Microinjection With reference now to FIG. 1, there is shown the concentration and purity of protein preparations used in the microinjection techniques discussed below. The protein preparations used for microinjection were analyzed by SDS-PAGE. Lane 1: $p110^{RB}$ from insect cells infected with recombinant RB baculovirus; lane 2: biotinylated rabbit anti-goat antibody; lane 3: anti-RB 0.495 antibody; lane 4: anti-RB R2 antibody; lane 5: anti-RB 0.47 antibody; lane 6: histone H1; lane 7: $p56^{RB}$ from $E.\ coli$. One microliter of each sample was loaded on a 15% acrylamide gel. The gel was stained with Coomassie brilliant blue. The positions of molecular weight standards, in kiloDaltons, are indicated.

Two forms of RB protein were prepared for the microinjection experiments. Wild type $p110^{RB}$, both hypophosphorylated and unphosphorylated forms, was purified to near homogeneity from baculovirus infected insect cells. At concentrations approaching 1 mg/ml, however, the protein aggregated into a form which could not be injected. To partially alleviate this problem, $p110^{RB}$ was purified, stored, and injected in buffers containing 10% glycerol. An unphosphorylated, amino-truncated 56 kDa RB protein ($p56^{PB}$), containing an intact T-antigen binding domain, was expressed in $E.\ coli$ and purified to near homogeneity. Since $p56^{RB}$ could be concentrated to 1 mg/ml and injected in a standard buffer containing 2% glycerol, it was used in most of the following experiments.

Human osteosarcoma cell line Saos-2 was chosen as the recipient cell line. This cell line lacked expression of wild-type p110$^{RB}$, but contained a cytoplasmic carboxy-truncated 95 kDa protein which can not bind T-antigen. Saos-2 cells responded to exogenous expression of RB, introduced by retrovirus mediated gene transfer, by an initial enlargement of cell size and loss of tumorigenicity in nude mice. Hence, it was determined that these cells might be particularly sensitive to injection of RB protein.

In FIG. 2, there is depicted the results of microinjection and immunostaining of Saos-2 cells labeled with BrdU. Saos-2 cells were injected as described herein. Panel A shows cells injected with p56$^{RB}$, immediately fixed, and indirectly immunostained for RB protein with Texas Red. Panel B contains uninfected cells labeled with BrdU for 4 hours, and then fixed and immunostained with fluorescein conjugated anti-BrdU antibody. Panels C and D are a single field of synchronized cells co-injected in early G1 with p56$^{RB}$ and RαG, incubated with BrdU for 24 hours, then fixed and stained. The cells stained with Texas Red mark injected cells, while the cells stained with fluorescein indicate cells which have incorporated BrdU. Panels E and F are a single field of cells also injected in early G1 with rabbit anti-goat alone.

To determine if the proteins could be translocated to the nucleus, sub-confluent, asynchronously growing Saos-2 cells were cytoplasmically microinjected with p56$^{RB}$ or p110$^{RB}$ and fixed 5 to 15 minutes later. The cells were then immunostained with rabbit anti-RB antibody 0.47 and a Texas Red-conjugated anti-rabbit antibody. Staining was mainly observed in the nucleus (FIG. 2A), although there was some staining observed in the cytoplasm of some injected cells. Both p110$^{RB}$ and p56$^{RB}$ proteins were capable of being transported to the nucleus within 15 minutes.

For subsequent experiments, cells were typically co-injected with an RB protein and a biotinylated, polyclonal rabbit anti-goat antibody (RαG) that served as a cytoplasmic marker for injected cells. It was estimated that 5–50 million molecules of RB protein were injected per cell. The number of endogenous RB protein molecules per cell was estimated to be approximately 1 million. Hence, the injected protein represented at least a 5 to 50-fold excess over endogenous levels. Following injection the cells were incubated in growth media containing bromodeoxyuridine (BrdU). Cells progressing through S phase during the labeling period will incorporate BrdU into their DNA. After fixation, cells were immunostained for BrdU with a fluorescein-conjugated antibody and for RαG with Texas Red conjugated streptavidin (FIG. 2). The percentage of injected cells that incorporated BrdU could be determined under a fluorescence microscope as the fraction of Texas red-positive cells that were also fluorescein-positive.

BrdU incorporation in RB-injected, asynchronously growing cells was only slightly less than that of uninjected cells or cells injected with RαG alone over a four hour labeling period (Table 1). These results indicated that the RB protein preparations used were not generally toxic to cells as determined by their continued viability, DNA incorporation, and cell adherence.

EXAMPLE II

RB Proteins Injected in Early G1 Block Incorporation of BrdU

Figure 2A:
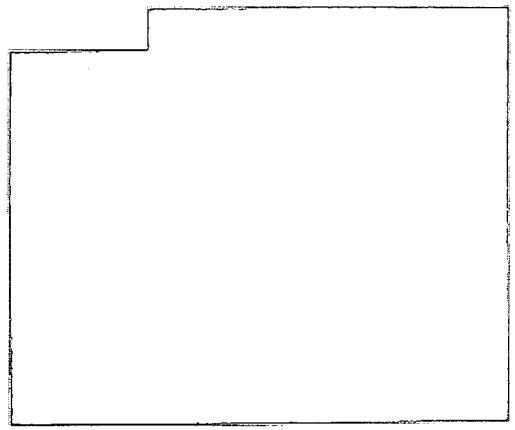
FIGS. 2A–2F are photomicrographs depicting microinjection and immunostaining of labeled Saos-2 cells.
Figure 2B:
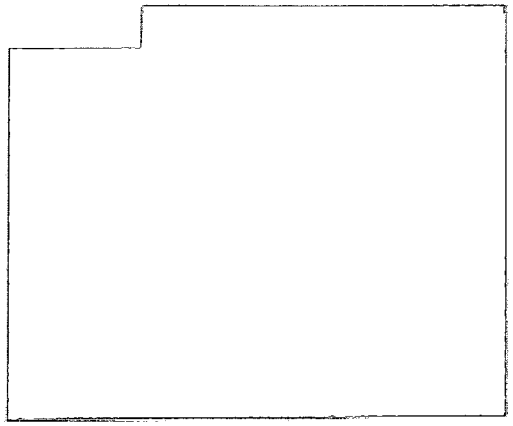
Figure 2C:
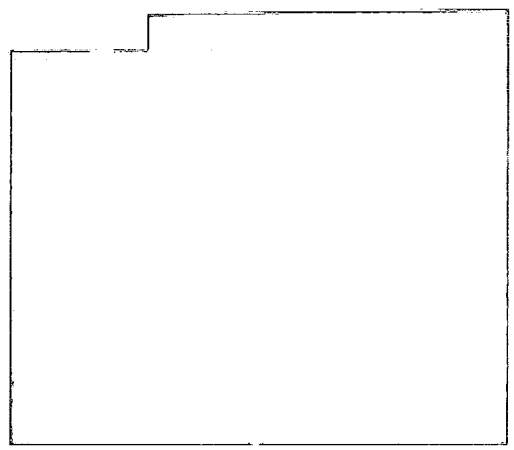
Figure 2D:
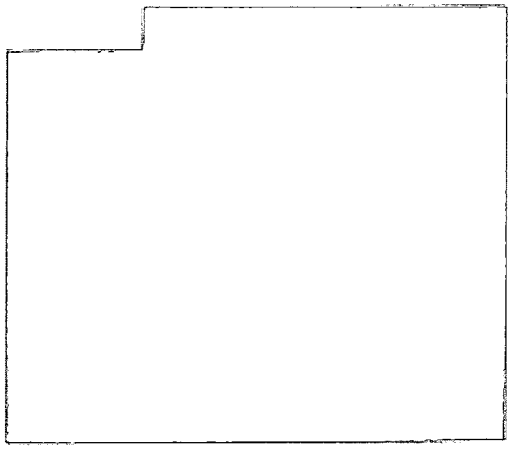
Figure 2E:
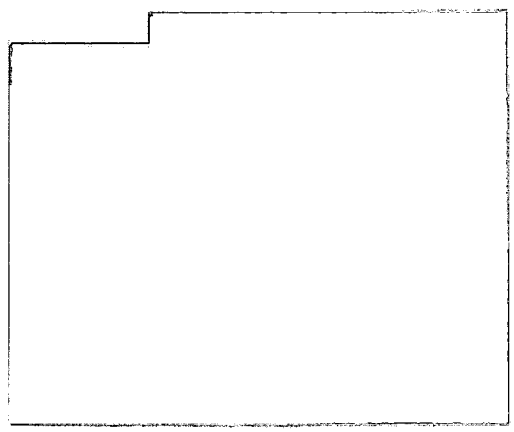
Figure 2F:
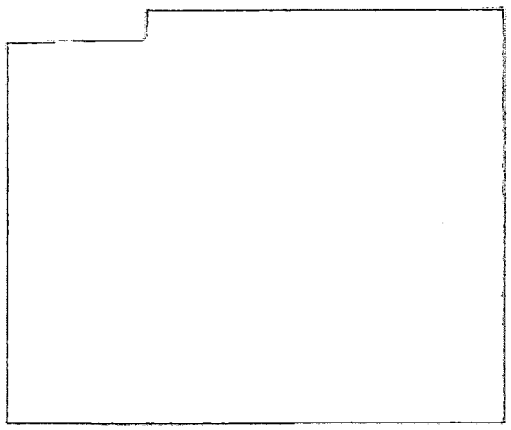

Since only a small effect on BrdU incorporation was observed upon injection of RB protein, the cells might only be sensitive to RB protein at a particular point in the cell cycle. The effect of RB protein could be more readily observed by injecting synchronized cells at this point. Cells were synchronized by treatment with nocodazole, which arrests cells in mitosis, and were then released and incubated for an additional 6 hours at which time non-adherent cells were removed and the remaining cells injected. Following a 24 hour incubation in the presence of BrdU, cells were fixed and stained for BrdU and RαG. At least 80–90% of uninjected cells could be stained for BrdU. Cells injected with p56$^{RB}$, however, were almost completely inhibited from progressing through G1 and into S phase over the labeling period. In this regard, please see Table 2 and FIGS. 2C and 2D. Similar inhibition was observed upon injection with p110$^{RB}$. In contrast, 60–70% of cells injected with histone and RαG, or RαG alone were able to enter S phase during the labeling period (FIGS. 2E and 2F). Although p110$^{RB}$ inhibited BrdU incorporation under these conditions, results were somewhat variable. Over time, p110$^{RB}$ preparations tended to aggregate which led to difficulty in injection. Relative to preparations of p110$^{RB}$, p56$^{RB}$ activity was very consistent.

To extend this observation to cells which already expressed wild-type p110$^{RB}$, p56$^{RB}$ was injected into cell line SR-40 which was derived from Saos-2 and stably expressed p110$^{RB}$. The effect of RB protein injection at early G1 phase on synchronized SR-40 cells was identical to the effect on Saos-2 cells (Table 2); very few cells injected with p56RB entered S phase over the 24 hour labeling period. Thus, the presence of endogenous wild-type p110$^{RB}$ did not interfere with the effect of p56$^{RB}$ on cell cycle progression.

Figure 3:
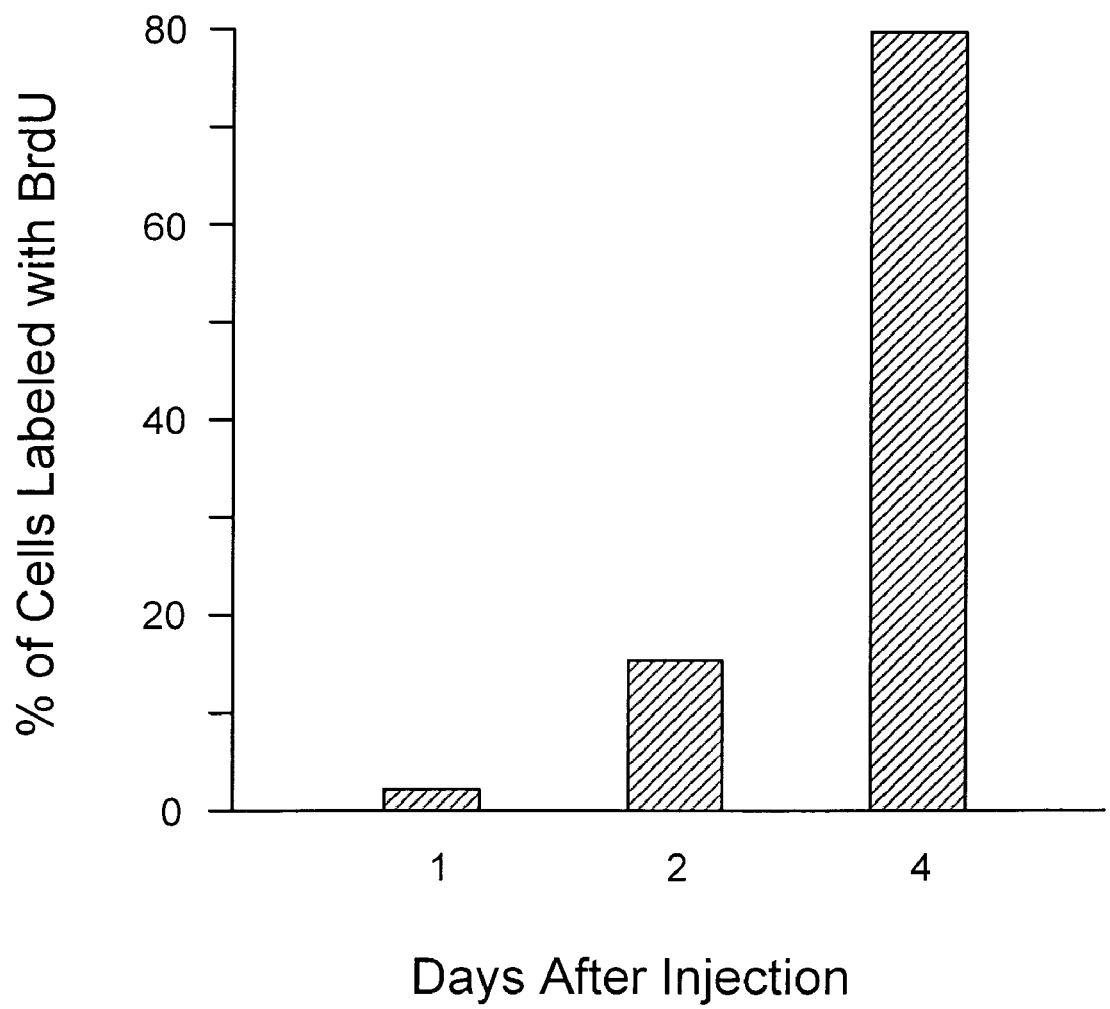
FIG. 3 graphically depicts the percentage of labeled cells up to four days after injection.

To determine how long the p56$^{RB}$-mediated block to entry of S phase lasted, the labeling period in the presence of BrdU was extended from one day to 2 or 4 days. FIG. 3 graphically shows the number of injected Saos-2 cells which incorporated BrdU during the labeling period. Saos-2 cells were co-injected with p56RB and RαG 6–7 hours after release from nocodazole treatment. After injection, cells were incubated in media supplemented with BrdU for the indicated number of days before fixing and staining. The percentage value indicates the number of injected cells which had incorporated BrdU during the labeling period. The values represent at least 100 injected cells. Inhibition of cell cycle progression was still observed after 2 days of incubation with BrdU prior to fixing and staining. Four days after injection, however, 80% of p56$^{RB}$ injected cells were able to incorporate BrdU. These observations indicated that the block of cell cycle progression by RB protein was reversible, and lasted between 2 and 4 days.

Figure 4:
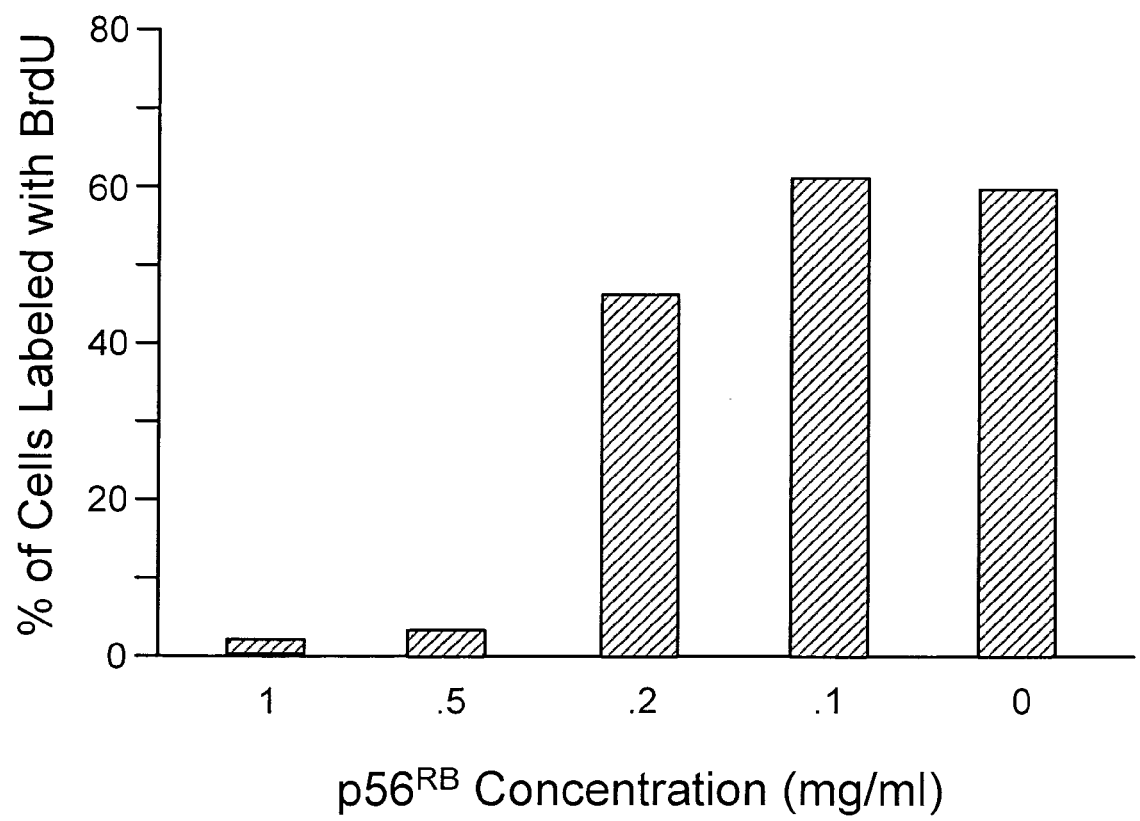
FIG. 4 graphically depicts the percentage of labeled cells as a function of $p56^{RB}$ concentration.

The dose dependence of the p56$^{RB}$ effect was also measured. Diluted aliquots of p56$^{RB}$ were injected into synchronously growing cells in early G1 phase. FIG. 4 graphically shows the dependence of cell cycle arrest on the dose of p56$^{RB}$. Saos-2 cells were co-injected 6–8 hours after release from nocodazole treatment with the indicated concentrations of p56$^{RB}$ and 1 mg/ml of RαG. After 24 hours of incubation in growth medium with BrdU, cells were fixed and stained for BrdU and RαG. The histogram indicates the percentage of injected cells which incorporated BrdU. Each value represents at least 150 injected cells. As shown in FIG. 4, 5-fold dilution of p56$^{RB}$ from the original concentration diminished the inhibitory activity while aliquots diluted by up to 2-fold still retained the inhibitory effect. Therefore, the block of entry into S phase by p56$^{RB}$ was dependent on the amount of protein injected. The threshold for block of BrdU incorporation was between 0.2 and 0.5 mg/ml of injected p56$^{RB}$.

To demonstrate that the inhibition of entry into S phase was caused by RB protein, we attempted to alleviate the block with reagents that bound specifically to p56RB. The p56RB was mixed with 1 mg/ml solutions of rabbit polyclonal antibodies 0.495, 0.47, or R2 (FIG. 1). These antibodies were raised against unique RB fusion proteins, and recognized p56RB on Western blots (31, 49, 56). Injection of the mixture of p56RB and 0.495 resulted in BrdU incorporation in about 30% of injected cells, compared to an almost total lack of incorporation in cells injected with p56RB alone (Table 2). Cells co-injected with p56RB and antibody 0.47 incorporated BrdU about 16% of the time. Co-injection of p56RB and antibody R2 also exhibited a lessened inhibitory activity although the effect was not as dramatic as with antibodies 0.47 or 0.495. Because antibodies that bind RB protein diminished the inhibitory effect of p56RB, the block to BrdU incorporation was due specifically to RB protein.

EXAMPLE III

BrdU Incorporation is not Inhibited by $56^{RB}$ if Injected in S phase

The lack of BrdU incorporation observed after injection of RB protein in early G1 phase could be explained by inhibition of DNA synthesis. To test this, Saos-2 cells were arrested in early S phase by treatment with aphidicolin and then injected with $p56^{RB}$. As shown graphically in FIG. 5, BrdU incorporation is not inhibited by $p56^{RB}$ if it is injected in the S phase. Saos-2 cells were arrested at G1/S by treatment with hydroxyurea or aphidicolin and were then injected.

After injection, cells were released from arrest and incubated with BrdU for 6–8 hours (hydroxyurea) or 4–6 hours (aphidicolin) at which time the cells were fixed and stained. Cells were also arrested in mitosis by treatment with nocodazole. After release, cells were collected and injected about 6 hours later. Following injection, cells were incubated with BrdU for 24 hours and then fixed and stained.

The protein preparations used for injected are indicated. The percentage of injected cells that stained for BrdU after the respective labeling period is shown. After injection, cells were released from aphidicolin treatment and incubated with BrdU for 4–6 hours, fixed, and immunostained for BrdU and RαG as described. In contrast to cells injected in early G1, approximately 60% of $p56^{RB}$ injected, aphidicolin arrested cells stained positively for BrdU incorporation. The percentage of cells entering S phase and the intensity of BrdU staining was similar to cells injected with histone and RαG, or RαG alone. To control for any possible lag period of the function of RB protein after injection, aphidicolin arrested cells injected with $p56^{RB}$ were incubated for an additional 6 hours prior to release and labeling with BrdU. Despite a somewhat lower intensity of BrdU staining, which was probably caused by the prolonged incubation with aphidicolin itself, the percentage of $p56^{RB}$ injected cells that incorporated BrdU was comparable to that of cells injected with RUG alone.

Figure 5:
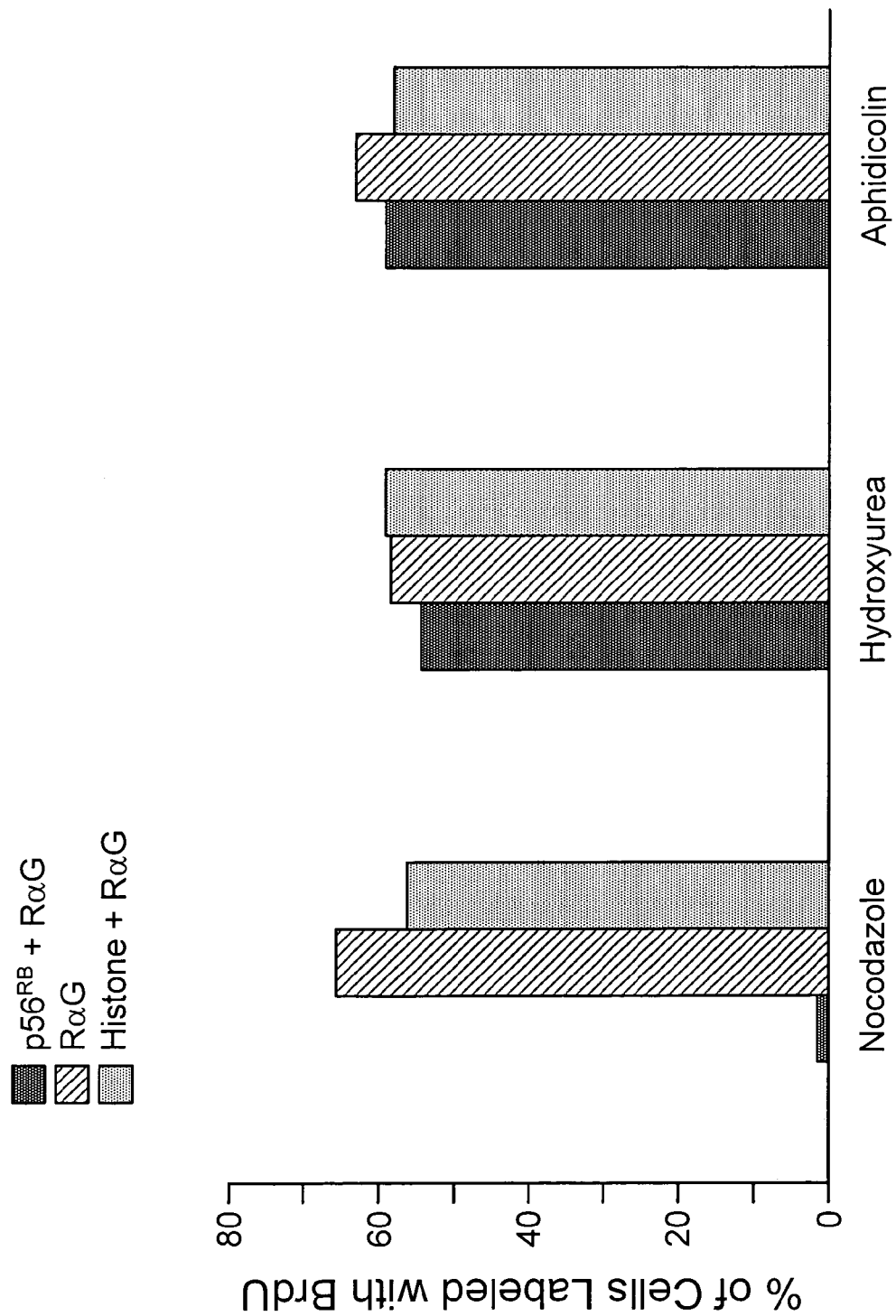
FIG. 5 graphically depicts the effect on cells when $p56^{RB}$ is injected in S phase.

Similar experiments were performed by arresting cells with hydroxyurea rather than aphidicolin. Hydroxyurea arrests cells near the G1/S boundary at a point distinct from aphidicolin arrest. Saos-2 cells were arrested near G1/S by treatment with hydroxyurea and then were injected with p56RB. After injection, cells were released from hydroxyurea treatment and labeled for 6 to 8 hours with BrdU. Again, injection of p56RB had no detectable inhibitory effect on BrdU incorporation (FIG. 5). The percentage of cells synthesizing DNA was the same whether injecting with $p56^{RB}$ and RαG, histone and RαG, or RαG alone.

The results were consistent with observations of asynchronously growing cells injected with RB protein, and implied that DNA synthesis, per se, was not blocked significantly by $p56^{RB}$. Therefore, inhibition of DNA synthesis could not explain the complete lack of BrdU incorporation seen upon injection of $p56^{RB}$ into synchronized cells in early G1 phase.

EXAMPLE IV

RB Protein Blocks Progression Through the G1 Phase at a Specific Point

Figure 6A:
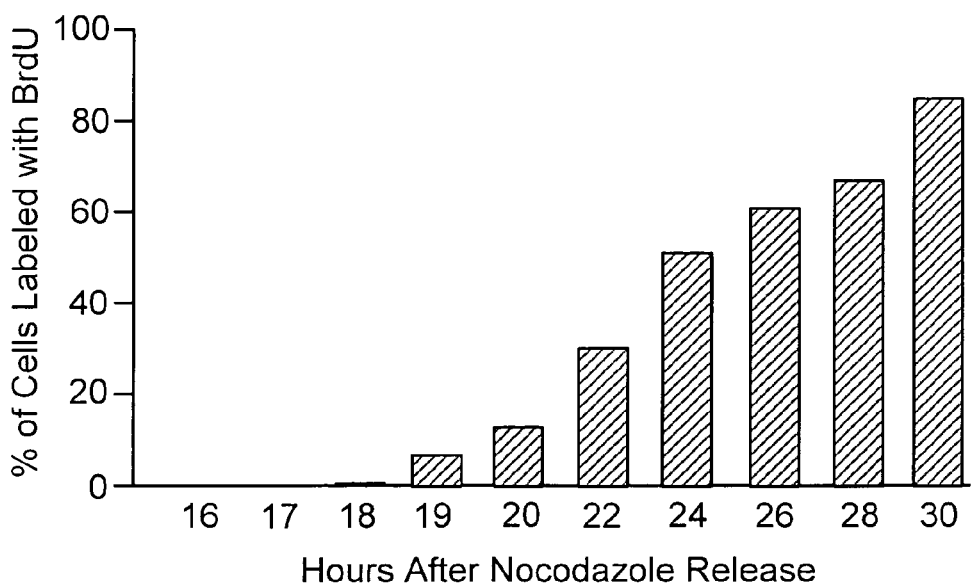
FIG. 6A graphically depicts the dependence of cell cycle arrest on the time period of injection of $p_{56}$ RB.
Figure 6B:
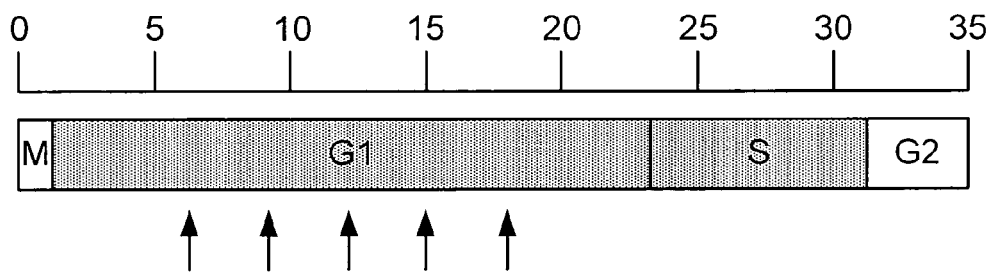
FIG. 6B graphically depicts the time of onset of S phase in Saos-2 cells after release from nocodazole arrest in mitosis.
Figure 6C:
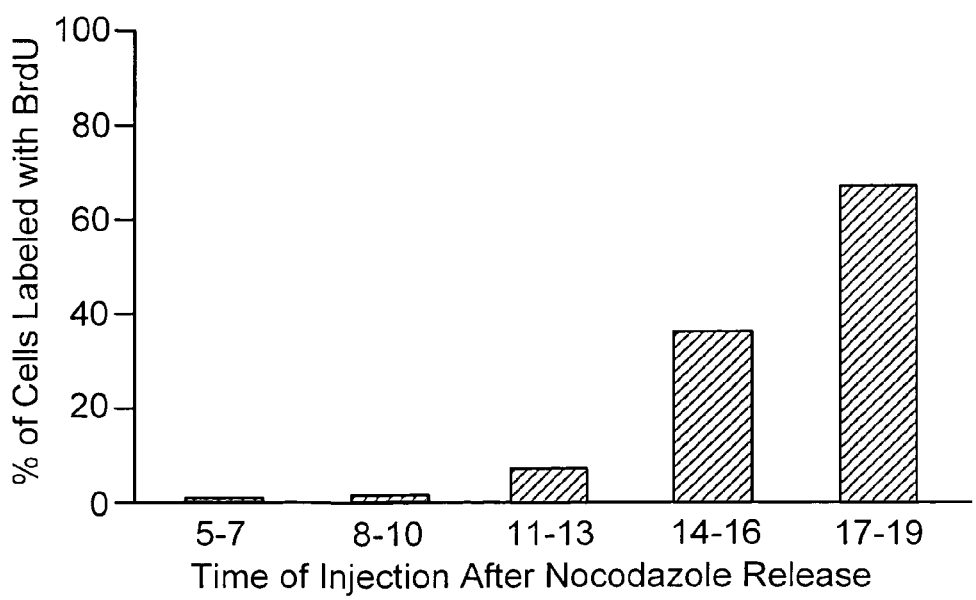
FIG. 6C graphically depicts SAOS-2 cells coinjected with $p56^{RB}$ and R α G after release from nocodazole treatment.

Given the results of the above experiments, the inhibitory effect of $p56^{RB}$ must have been due to a block in progression through the G1 phase. To define the position of this arrest within the G1 phase, a careful calibration of the time of onset of S phase in the cell cycle of Saos-2 cells was first determined. FIGS. 6A, 6B and 6C graphically depict the dependence of cell cycle arrest on the time period of injection for $p56^{RB}$. With regard to FIG. 6A, Saos-2 cells were arrested in mitosis by treatment with nocodazole. After release from arrest, the cells were incubated for the indicated number of hours in the presence of BrdU, then fixed and stained with an anti-BrdU antibody. The histogram indicates the percentage of counted cells that stained for BrdU. Each value represents at least 200 cells.

As shown in FIG. 6A, uninjected cells began to stain for BrdU at approximately 20 hours after the release. By 30 hours virtually 80 to 90 percent of cells had incorporated BrdU. Based on this, a time-course experiment in which nocodazole treated cells were injected with $p56^{RB}$ at various times after release from arrest was then performed. FIG. 6B depicts the time of onset of S phase in Saos-2 cells, in hours, after release from nocodazole arrest in mitosis. The length of G1 phase is about 22 to 24 hours. The length of S phase is about 7 to 8 hours. The length of the G2 phase has not been precisely determined. The arrows indicate the time points of injection that are used for the experiment described in 6C.

With regard to FIG. 6C, Saos-2 cells were co-injected with 1 mg/ml $p56^{RB}$ and RαG at the indicated times, in hours, after release from nocodazole treatment. Incubation was continued after injection in growth medium with BrdU until 30 hours after the original release from nocodazole. After BrdU labeling, cells were fixed and stained for BrdU and RαG. The histogram shows the percentage of $p56^{RB}$ injected cells which incorporated BrdU. Each value represents at least 200 injected cells.

Very few cells entered S phase at 30 hours after release if injected with $p56^{RB}$ 5–10 hours after release from nocodazole (FIG. 6C). A significant number of cells incorporated BrdU if injected with $p56^{RB}$ after 14–16 hours post-arrest. If injected 17–19 hours after release, $p56^{RB}$ had no detectable inhibitory effect on entry into S phase.

Given that S phase began between 22 and 24 hours after release from nocodazole, the results suggested that cells become refractory to the inhibitory effect of injected RB protein about 6–10 hours prior to the G1/S transition. This confirmed the notion that the inhibitory effect of RB protein on the cell cycle was due to a block in progression through the G1 phase rather than a block of DNA synthesis itself. Furthermore, the observations implied that RB may function at a specific, relatively early time point within the G1 phase.

EXAMPLE V

SV40 T Antigen Relieves the Blocked Cell Cycle Progression by p56RB

As a test of the hypothesis that SV40 T-antigen can functionally inactivate RB protein upon binding, we compared the effect of $p56^{RB}$ injection on G1 progression in the presence or absence of T-antigen. A 1 mM T peptide solution which was capable of binding to $p56^{RB}$, was mixed with an equal volume of $p56^{RB}$ and injected into synchronized cells in early G1 phase. At this concentration, the peptide was at a 100 to 200-fold molar excess over the RB protein. About 28% of synchronized cells injected with the $p56^{RB}$/T peptide mixture entered S during the labeling period (Table 3). If the T peptide concentration was increased to 5 mM, or a 500 to 1000-fold molar excess, approximately 70% of injected cells could incorporate BrdU. By contrast, almost none of the cells progressed into S phase after injection with $p56^{RB}$ and a 500 to 1000-fold molar excess of a carboxy-terminal p53 peptide that did not bind $p56^{RB}$.

The effects of injection of $p56^{RB}$ on African Green monkey kidney cell lines CV-1 and COS-7 were also compared. COS-7 cells were chosen since they were derived from CV-1 cells by transformation with an origin-defective SV-40 mutant, and they expressed a high level of T-antigen. Therefore, they can serve as a good system for testing the effect, if any, of the presence of endogenous T-antigen on the activity of the injected RB protein. The percentage of synchronized CV-1 cells injected with $p56^{RB}$ in early G1 phase that incorporated BrdU was at least 5-fold lower than cells injected with RαG alone (Table 3). Synchronized COS-7 cells, however, were not inhibited at all from progressing into S phase. These results indicated that the presence of endogenous T-antigen, or co-injection with a T-antigen peptide, could neutralize the inhibitory activity of RB protein. Thus, those skilled in the art can utilize this system to screen RB protein fragments to identify those fragments capable of blocking cell cycle progression by comparing the percentage of CV-1 to COS-7 cells entering S phase in the presence of the RB protein fragment.

The foregoing results provide functional evidence which indicates that RB protein can act by inhibiting progression through the cell cycle. Injection of $p56^{RB}$ does not detectably inhibit DNA synthesis per se, since aphidicolin or hydroxyurea arrested cells are not affected, but rather blocks progression through the G1 phase. This inhibition of cycle progression is dose-dependent, is not due to general toxicity to the cells, and is specific for RS protein because antibodies that bind specifically to $p56^{RB}$ can attenuate its activity. The cycling cell is sensitive to RB protein inhibition until roughly 6–10 hours before the onset of DNA replication; after this time, exogenously added $p56^{RB}$ no longer inhibits progression into S phase. Assuming there is a small lag period between $p56^{RB}$ injection and its appearance in an active form in the nucleus, it may be concluded that RB protein inhibits progression to S phase at a critical point in G1 phase. The 6–10 hour time window prior to DNA synthesis may be analogous to the time period following the G1 restriction point, a point of irreversible commitment to S phase in mammalian cell lines.

The time window defined may not correspond precisely to the time point when RB protein functions under normal physiological conditions. The time it takes for injected $p110^{RB}$ or $p56^{RB}$ to appear in an active configuration and/or location is not clear. However, RB proteins are transported to the nucleus within 15 minutes after cytoplasmic injection, and continued incubation of $p56^{RB}$ injected cells with aphidicolin for several hours prior to release and labeling does not decrease the percentage of cells which incorporate BrdU. These observations suggest that the time it takes RB protein to become functional after injection may be short.

The transition from an active form of $p110^{RB}$ to an inactive form has been assumed to occur at the G1/S boundary since the protein undergoes extensive phosphorylation at this point. However, because of the foregoing, an earlier time period, which seems to be critical for $p56^{RB}$ activity has been defined. Thus, RB may be involved in a regulatory decision which the cell makes at a point about 6–10 hours prior to the G1/S transition. The RB protein can be phosphorylated at multiple sites both in vivo and in vitro, yet it is not yet clear which phosphorylation sites are important for RB function. Subtle increases in phosphorylation of $p110^{RB}$ during G1 phase may be responsible for the cells transition from an RB-responsive to a non-responsive state. Some phosphorylation of $p110^{RB}$ has been observed in the G1 phase, although this may have been due to incompletely synchronized cells.

The carboxy-terminal 56 kiloDaltons of RB is sufficient to inhibit progression through the G1 phase. This indicates that the carboxy-terminal half of $p110^{RB}$ is, in fact, a functional domain with respect to its effect on the cell cycle. Two biochemical activities have been ascribed to the carboxy-terminal half of $p110^{RB}$, DNA binding and protein binding. Based on findings to date, the sequence specificity of RB binding to DNA is low; although RB binds with slightly higher affinity to DNA with high G/C content, no particular sequence is strongly preferred. On the other hand, specificity has been observed in binding or RB to proteins. The transforming proteins of several DNA transforming viruses as well as a subset of cellular proteins bind to the same domain of $p110^{RB}$ and therefore can compete with one another for RB protein biding. This region is where the majority of naturally occurring inactivating mutations of RB are located. It seems likely, then, that the block to progression of G1 phase by RB protein is dependent on specific protein—protein interactions.

Mixing $p56^{RB}$ with a T-antigen derived peptide, which can bind $p56^{RB}$, eliminates its inhibitory consequences. Co-injection of $p56^{RB}$ with a T peptide containing a single amino acid substitution at a 500 to 1000-fold molar excess can also attenuate, to some extent, the block to cell cycle progression. Although the amino acid substitution lowers its affinity for RB protein in vitro, this mutant T peptide may still bind $p56^{RB}$ in vivo when present in vast molar excess. In contrast, the injection of a totally irrelevant p53 peptide had no effect on the inhibitory activity of RB protein, which thus substantiated the specificity of the interaction observed between RB protein and T-antigen peptide. CV-1 cells injected in early G1 with $p56^{RB}$ are arrested before S phase while COS-7 cells, which express high levels of T-antigen, are not arrested, however. These observations, taken together, indicate that T-antigen binding does have functional consequences for RB protein. Since the injected $p56^{RB}$ is unphosphorylated, the test results are consistent with the hypothesis that the active form of RB protein, with respect to its inhibition of cell proliferation, is the unphosphorylated form. Therefore, the transforming proteins of some DNA tumor viruses, including SV40 T-antigen and adenovirus E1A, may promote cell growth, at least in part, by binding and inactivating underphosphorylated $p110^{RB}$. The immortalization of cells and the induced escape from quiescence upon expression of these transforming proteins are phenotypes consistent with deregulation of the cell cycle.

Given that the carboxy-terminal half of p110$^{RB}$ is biologically active, the question remains as to the function of the amino terminal half of the protein. Sequences within this region may be required for the proper phosphorylation of p110$^{RB}$. In murine cells, polypeptides similar to p56$^{RB}$ are not hyperphosphorylated. Also, several consensus sites for the cdc2/MPF kinase are present within this region. It follows that the amino terminal half of p110$^{RB}$ may contain a regulatory domain which can modulate RB function. Release of p56$^{RB}$ block to G1 progression does not occur until 3–4 days after injection; this lengthy arrest period may be due to the inability of the cell to regulate RB protein in a normal manner, or to the relatively large amount of RB protein injected. A comparison of the activity in this assay of different RB proteins with mutations in phosphorylation sites would aid in resolving this issue. If p56$^{RB}$ is constitutively active, mutations creating such polypeptides would be expected to inhibit cell proliferation and thus place cells at a selective disadvantage. This may explain the lack of naturally occurring mutants within the amino terminal half of RB.

Figure 10:
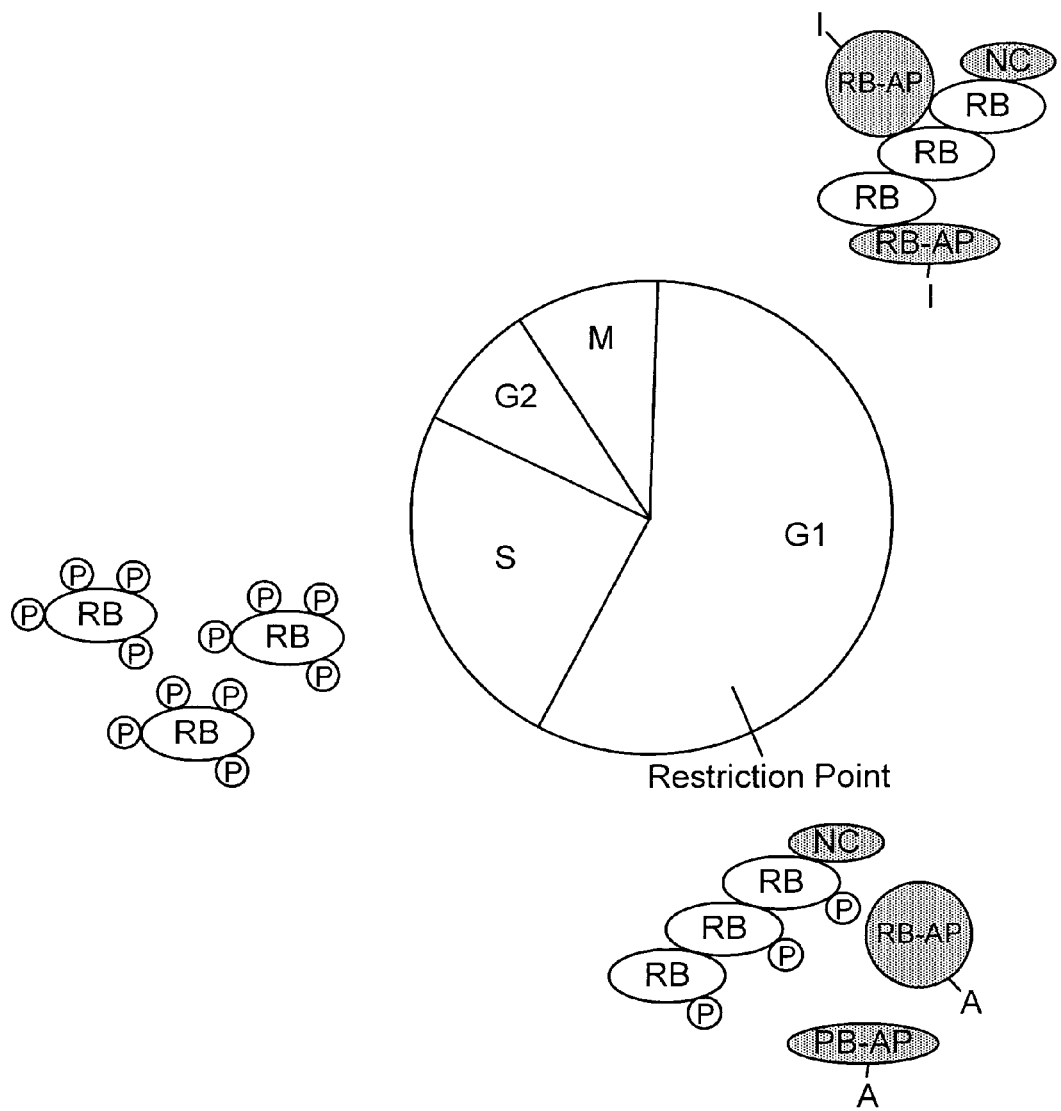
FIG. 10 graphically depicts various stages of the cell cycle and the status of RB protein in the cell cycle.
Figure 11:
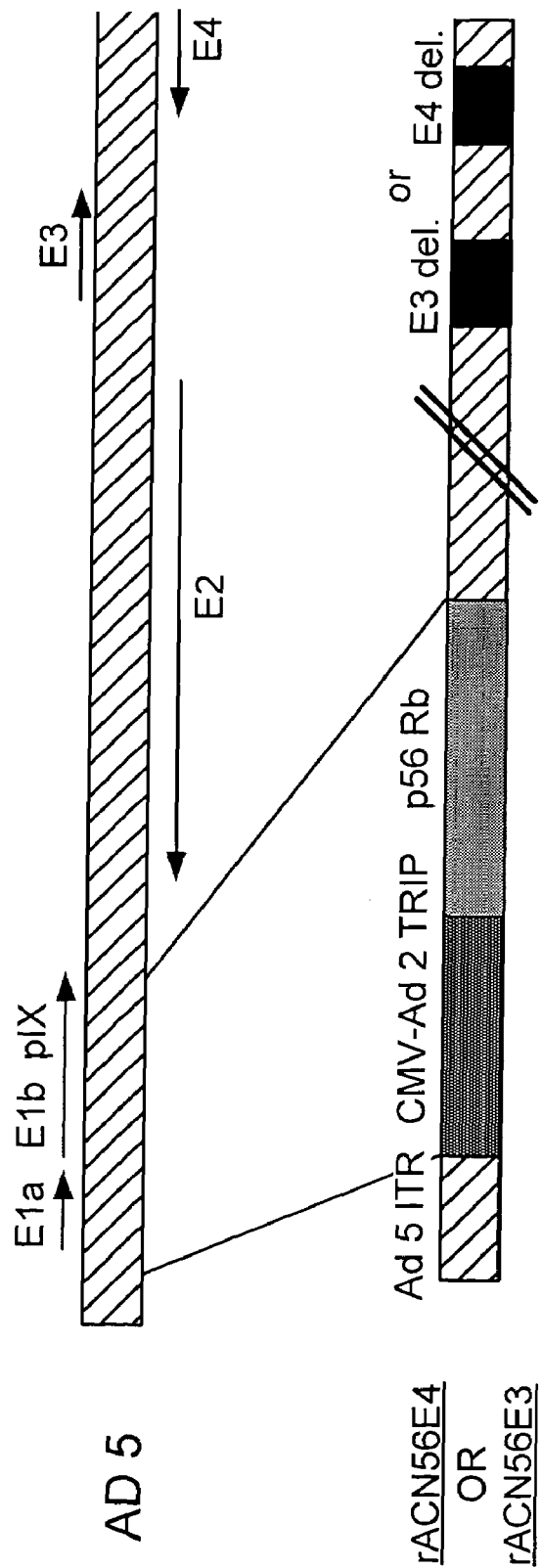
FIG. 11 is a schematic of p56 recombinant adenoviruses. Two recombinant p56 adenoviruses were made based on the Ad 5 type backbone. In each, nucleotides 360–4030 of the adenovirus have been replaced by the cDNA of p56 driven by the CMV promoter followed by the Ad 2 tripartite leader cDNA. The ACN56E4 virus has a 1.4 kb deletion within the E4 region of the virus, while the ACN56E3 virus has a 1.9 kb Xba I deletion within the E3 region.
Figure 12:
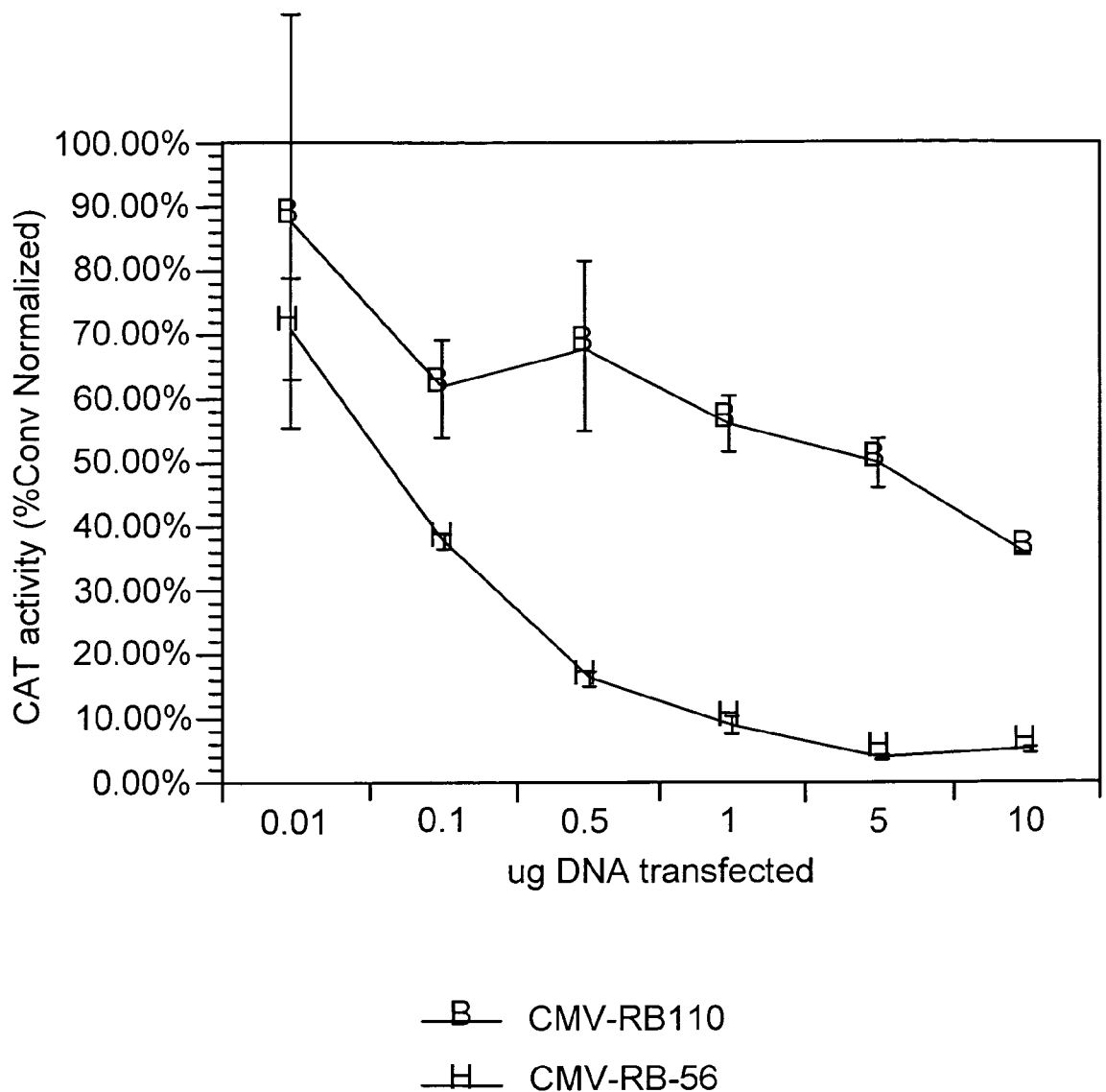
FIG. 12 shows suppression of E2F Mediated Transcription by $p56^{RB}$ and $p110^{RB}$. Plasmid vectors directing expression of either $p56^{RB}$ or $p110^{RB}$ from the cytomegalovirus immediate early promoter were cotransfected into the C33A cervical carcinoma cell line with E2F-GAT reporter plasmid. The ability of either $p56^{RB}$ or $p110^{RB}$ to suppress the E2F regulated transcription of the CAT (chloramphenicol acetyltransferase) gene was determined by measuring the activity of the CAT reporter enzyme. The concentration of the $p56^{RB}$ and $p110^{RB}$ plasmids was varied in order to assess the potency of each vector in regulating the E2F-CAT transcriptional unit. The results indicate the $p56^{RB}$ is a more potent repressor of E2F mediated transcription than $p110^{RB}$.
Figure 13A:
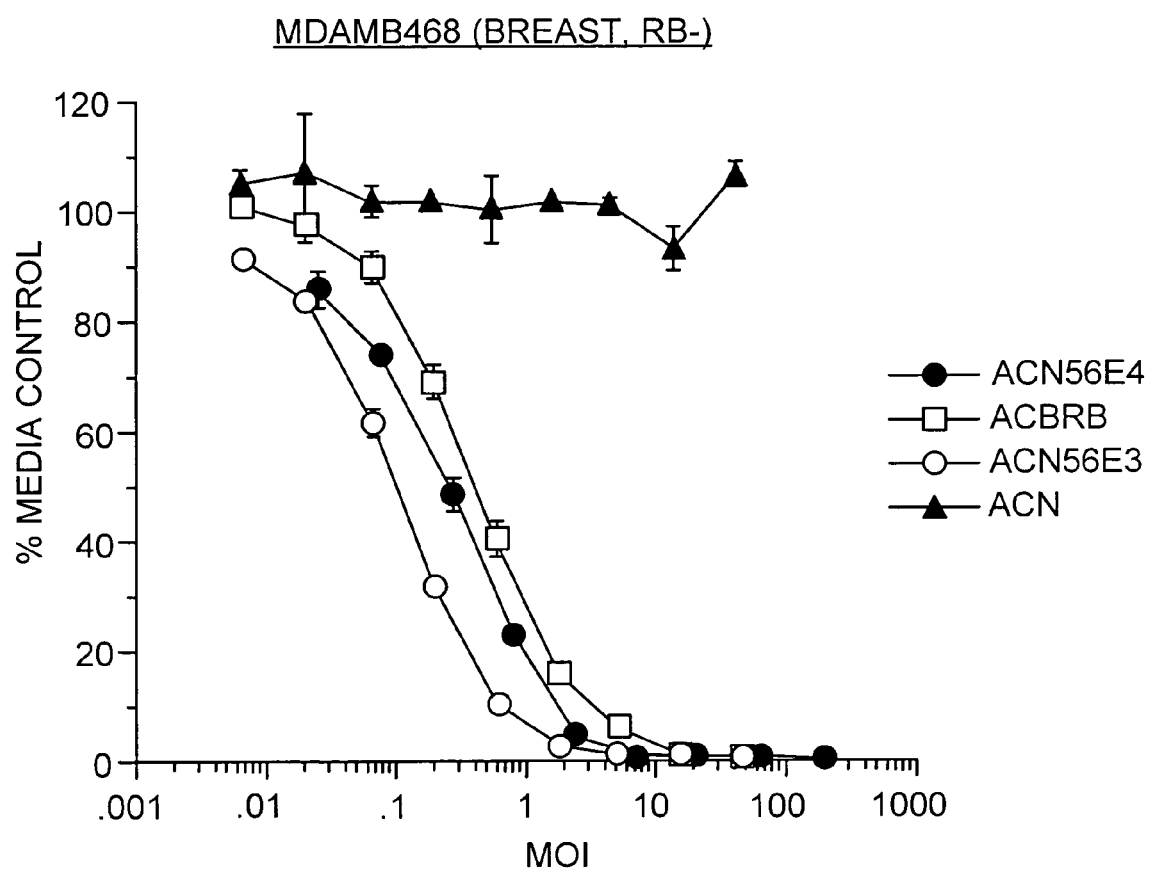
FIGS. 13A–D depict p56 vs. RB inhibition of DNA synthesis in both RB positive and negative tumor cell lines. Tumor cell lines were infected at increasing MOI with either control virus ACN, full length $p110^{RB}$ virus ACBRB, or either of the $p56^{RB}$ viruses ACN56E3 or ACN56E4, as indicated. Tumor type and endogenous RB status for each cell line is noted. DNA synthesis, as measured by uptake of 3H-thymidine at 48 hours following infection of cells with virus, is plotted as percent of media control. Results are from duplicate infections, with the error plotted as +/−sd. Panel (A) breast, RB⁻; (B) small cell lung carcinoma, RB⁺; (C) small cell lung carcinoma RB⁺; and (D) breast cancer RB⁺.
Figure 13B:
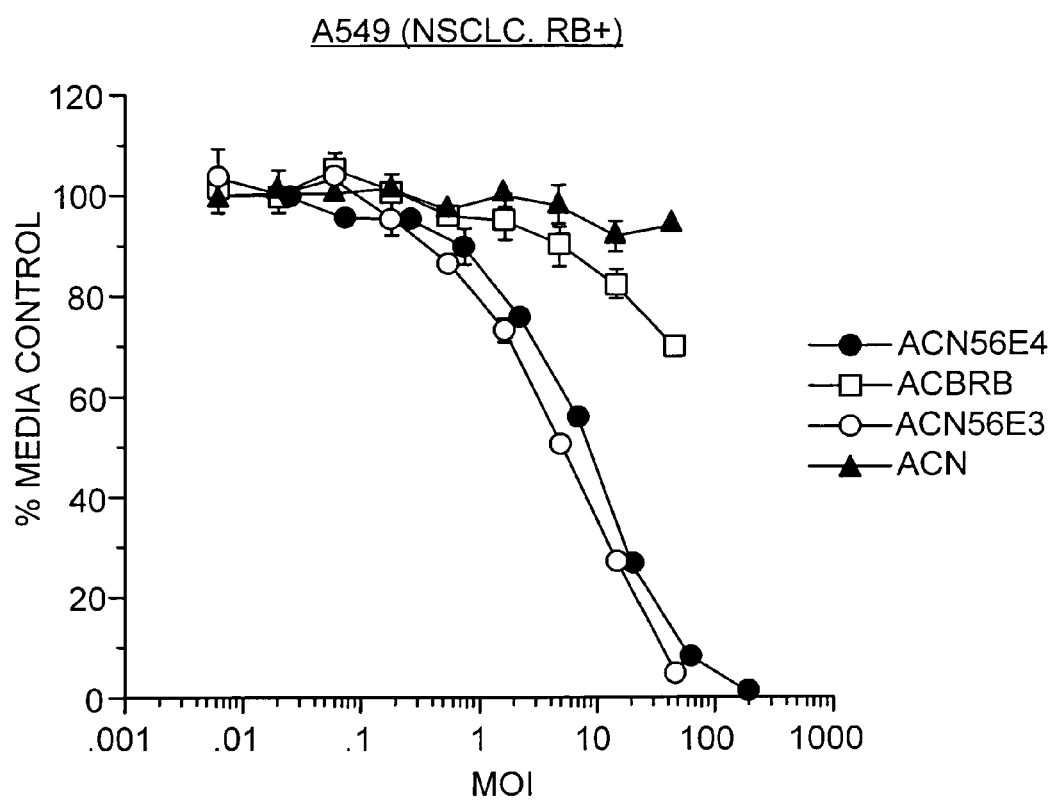
Figure 13C:
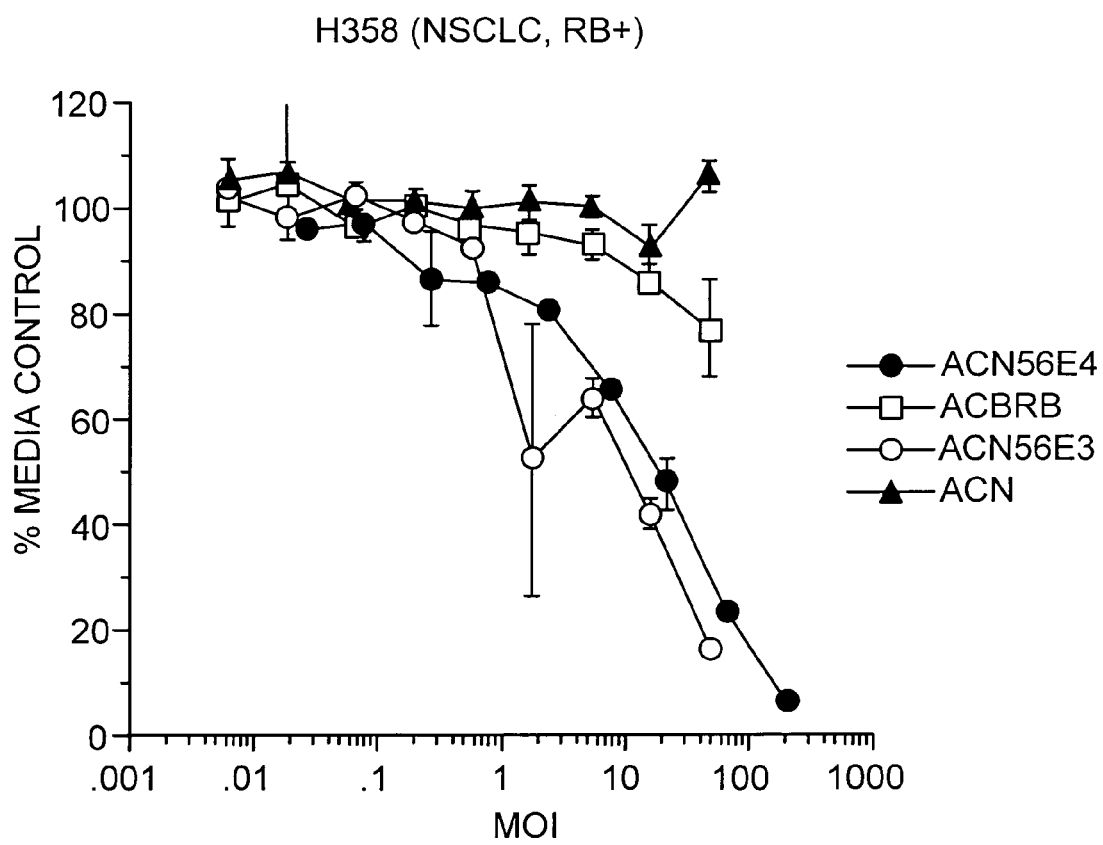
Figure 13D:
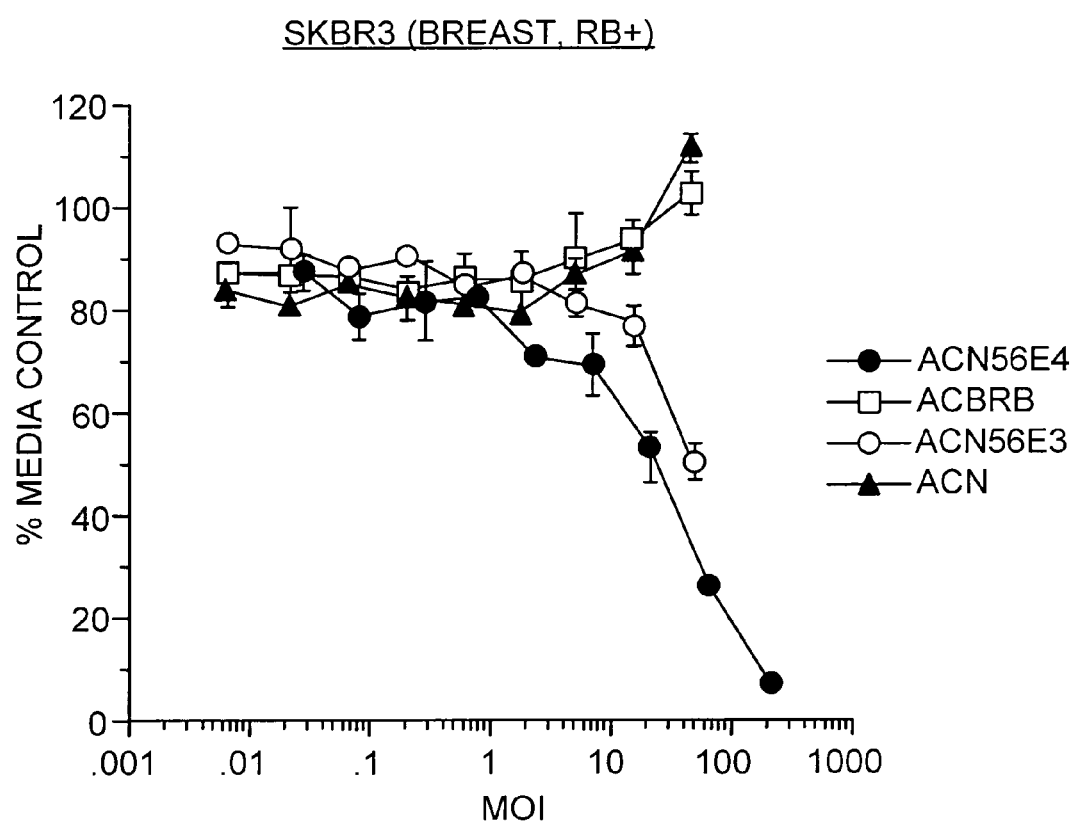

The results described here indicate that RB participates in control of cell cycle progression by acting at a control point within the G1 phase. This point is significantly earlier than the observed hyperphosphorylation of p110$^{RB}$ as cells enter S phase. Thus, it is reasonable to propose a model which incorporates the test results as well as other known properties of p110$^{RB}$ (FIG. 10). Since RB has been shown to associate with several cellular proteins, and the protein binding domains of RB are sufficient to block cell cycle progression, it seems highly possible that the binding of cellular proteins is critical for the observed RB function. The model suggests that RB participates in regulation of the cell cycle by sequestering cellular proteins vital for DNA synthesis and/or cycle progression at a particular time period during the G1 phase. Inactivation of p110$^{RB}$ by mutation, by phosphorylation at key sites, or by binding with transforming proteins is hypothesized to release these cellular proteins, permitting them to provide functions that are necessary for continuation of the cell cycle. Once cells commit themselves to continuation of the cell cycle by release of these proteins, p110$^{RB}$ can no longer effectively inhibit their function and therefore the block to cell cycle progression is relieved.

Sub-nuclear localization of RB may be crucial to its ability to sequester other proteins in an inactive form. RB protein segregates with cellular replication proteins to sites of Herpes virus DNA replication upon infection, a situation where normal regulation of the cell cycle is subverted. In G1, the underphosphorylated form of p110$^{RB}$ is tightly associated with a particular nuclear locale. Purified p110$^{RB}$ also tends to polymerize, perhaps explaining the difficulty in maintaining its solubility at high concentrations, and it has limited homology to a certain class of intermediate filament proteins. These observations suggest the p110$^{RB}$ may contribute to some structural component of the nucleus, and that association of p110$^{RB}$ with this component is necessary for its inhibition of cell cycle progression. The hyperphosphorylation would presumably free p110$^{RB}$ from its sub-nuclear location allowing RB to provide some other function, or to reset its ability to sequester other proteins during the subsequent cell cycle. The model predicts that regulation of RB activity could be accomplished by specifying its nuclear location and/or the cellular proteins to which it binds.

The biological consequence of complete loss of RB function is generation of retinoblastoma and perhaps some other tumors. Involvement of RB in the cell cycle provides a means to explain this phenomenon. RB may act. to halt progression through G1 phase until the cell receives proper signals for commitment to continuation of the cell cycle. Thus, loss of RB function may contribute to tumorigenesis in different tissues by permitting unscheduled cell proliferation.

In view of the foregoing, it can be seen that the RB gene product is a nuclear phosphoprotein which under goes changes in phosphorylation status in synchrony with the cell cycle. To test whether RB regulates cell cycle progression, purified RB proteins, either full-length or a truncated form containing the T-antigen binding region, were injected into cells and the effect on entry into S phase determined. Synchronized cells injected early in G1 with either protein are inhibited from progressing into S phase. This effect is antagonized by co-injection with antibodies directed against RB. Injection of RB protein into cells arrested at the G1/S boundary or 6–10 hours before the end of G1 has no effect on BrdU incorporation suggesting that RB protein does not apparently perturb DNA synthesis in S phase. These results provide direct evidence that RB may regulate cell proliferation by restricting cell cycle progression at a specific point in G1, and they also establish a biological assay for the activity of RB protein. Co-injection of RB protein with a T-antigen peptide, or injection into cells expressing T-antigen does not prevent cells from progressing into S phase. This experiment substantiates the hypothesis that T-antigen binding has functional consequences for RB protein.

EXAMPLE VI p56$^{RB}$ Gene Inhibits Cellular Proliferation

Having shown that p56$^{RB}$ protein inhibits cellular proliferation the capacity of the gene encoding p56$^{RB}$ protein to inhibit cellular proliferation was tested.

Virus Construction. Construction of recombinant adenoviruses expressing p56$^{RB}$ protein followed standard procedures. A plasmid containing p56$^{RB}$ encoding cDNA was contructed by replacing the p53 cDNA from the plasmid ACN53 (Wills et al., "Development and characterization of recombinant adenoviruses encoding human p53 for gene therapy of cancer." *Human Gene Therapy* 5:1079–1088 (1994)) with a 1.7 kb Xba 1, Bam H1 fragment isolated from the plasmid petrbc (Antelman et al., "Inhibition of tumor cell proliferation in vitro and in vivo by exogenous p110$^{rb}$, the retinoblastoma tumor suppressor protein." *Oncogene* 10:697–704 (1995)) which contains the p56 cDNA. The resulting plasmid contains the Ad 5 inverted terminal repeat, viral packaging signals and E1a enhancer, followed by the human cytomegalovirus immediate early gene promoter (CMV) and Ad 2 tripartite leader cDNA to drive p56$^{RB}$ expression. The p56$^{RB}$ cDNA is followed by Ad 2 sequence 4021 through 10462 in a pML2 background. This plasmid is linearized with Eco RI and co-transfected with the large fragment of Bsp 106 digested dl327 (E3 deleted) and the vector is herein referred to as ACN56 (Thimmappaya et al., *Cell* 31:543–551 (1982) or H5ile4 (E4 deleted) (Hemstrom et al., *J. Virology* 62:3258–3264 (1988)). Recombinant viruses were isolated and identified by restriction digest analysis and further purified by limiting dilution. Virus particles were prepared and titered by standard methods (Graham and Prevec, "Manipulation of adenovirus vectors." *Methods in Molecular Biology, Vol. 7: Gene Transfer and*

*Expression Protocols.* Murray, E. J. (ed.) The Humana Press Inc., Clifton, N.J. 7:109–128 (1991)).

Construction of ACBRB.

Construction of the recombinant adenovirus expressing full length p110 RB followed standard procedures. A plasmid containing full length RB was constructed as follows. Full length RB cDNA was isolated from the plasmid pLR-BRNL as a 3.9 kb Bam HI fragment (Huang et al., *Science* 242:1363–1366 (1988)). This isolated fragment was subcloned into the Bam HI site of pBS KSII+ (Stratagene) and redigested out with Kpn I to be inserted into this site of the plasmid pSP72 (Promega). These manipulations provided a full length RB with Xho I sites on both the 5' and 3' ends of fragment. This 3.9 kb RB fragment was isolated from an Xho I digest and cloned into the adenovirus gene transfer vector pNL3C to make the plasmid pAMARbN (used for first generation Rb expressing adenoviruses). This plasmid was further digested with Bam HI and Kpn I to remove the full length RB cDNA and subcloned into the plasmid pGEN7f (Promega). The RB fragment was then isolated as a 3.9 kb, 5' Xho, 3' Bam HI Rb fragment which was subsequently ligated iinto Xho I, Bgl II digested pNL3CMV adenovirus gene transfer plasmid. The resulting plasmid contains the Ad 5 inverted terminal repeat, viral packaging signal and E1a enhancer, followed by the human cytomegalovirus immediate early gene promoter (CMV) and Ad 2 tripartite leader cDNA to drive RB expression. The p110 RB cDNA is followed by Ad 5 sequence 3330 through 5790 in a pML2 background. This construct was subsequently linearized with Nru I and co-transfected with the large fragment of Cla I digested dl309 adenovirus (Jones and Shenk, *Cell* 17:683–689 (1979)) using a $CaPO_4$ transfection kit (Stratagene). Recombinant adenoviruses were isolated and identified by restriction digest and PCR analysis, and further purified by limiting dilution. Virus particles were prepared and titered by standard methods (Graham et al., *Cancer Research* 51:841–849 (1991)).

The recombinant adenovirus ACBRB expressing full length p110 RB is based on the Ad 5 type backbone. Nucleotides 360–3330 of the dl309 adenovirus sequence has been replaced with the cDNA of the full length p110 RB driven by the CMV promoter and Ad 2 tripartite leader cDNA.

Assay of E2F mediated Transcription. $2.5 \times 10^5$ C33A cervical carcinoma (RBmut) cells (ATCC #HTB 31) were seeded in each well of a 6-well tissue culture plate. Transfection was performed using the Strategene (La Jolla, Calif.) MBS transfection kit protocol. All transfections were performed in duplicate. Cells were transfected with 5 ug CMV-β-gal plasmid, 5 ug of E2-CAT reporter plasmid and 0–10 ug of PCMV-$RB^{110}$ or pCMV-$RB^{56}$. The total amount of DNA transfected was held constant by adding varying amounts of pUC19 DNA to each transfection mix. At 48 hr. post transfection, cells were harvested and soluble cell extracts were prepared as described (Current Protocols in Molecular Biology). 50 uL of each cell extract was assayed for CAT activity as described (Current protocols in Molecular Biology). Free and acetylated forms of $^{14}$-C-chloramphenicol (Amersham) were resolved by thin layer chromatography on silica plates and were visualized and quantitated by exposure on a phosphorimager (Molecular Dynamics), and the percent (%) conversion was calculated.

To correct for variations in cell number and transfection efficiency between samples, C33A cells extracts were also assayed for β-galactosidase activity as described (Rosenthal, N. *Met. Enzymology* 152,704 (1987)). The β-galactosidase assays were performed using the β-galactosidase enzyme assay system (Promega #E-2000) and reaction product was monitored using a Spectra Max 250 SoftMax plate reader (Molecular Dynamics, Sunnyvale, Calif.).

ACN56 inhibits proliferation of $RBP^{pos}$ tumor cell lines. The effects of viral constructs on proliferation were assayed by [$^3$H] thymidine incorporation. Bladder carcinoma cell lines, RT4 (ATCC CRL 7937) and UM-UC-3 (ATCC CRL 1749), are $RBP^{pos}$ cell lines and were plated at $5 \times 10^3$ cells per well in 96-well plate. The following day cells were treated with ACN (control), ACBRB and ACN56 at MOIs ranging from 1 to 300 in triplicate. 48 hours after infection, cells were pulsed with [$^3$H] thymidine for 18 hours. Cells were harvested and counted by liquid scintillation (TopCount). The % media control was determined by average counts treated/average counts untreated×100. $ED_{50}$ was determined as the dose that resulted in 50% incorporation compared to untreated control.

Figure 14A:
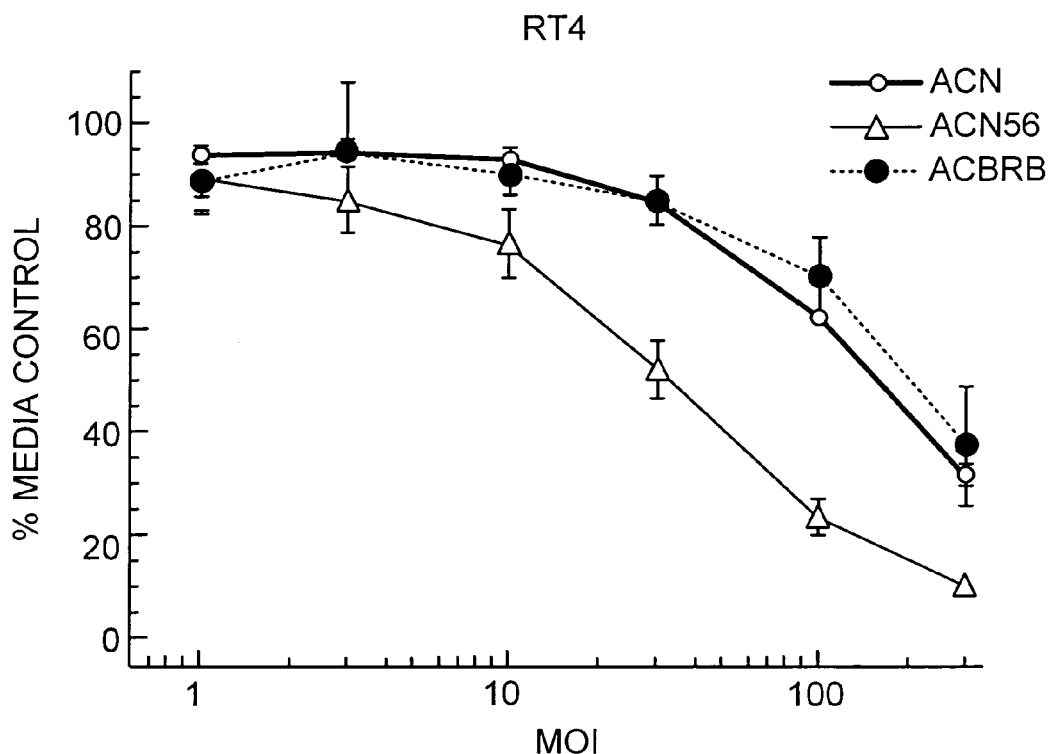
FIGS. 14A–B show the effect of viral constructs including AM (control), the ACERB ($p110^{RB}$ protein) and ACN56 (the $p56^{RB}$ protein) on cellular proliferation of RB positive tumor cell lines assayed by [³H] thymidine incorporation.
Figure 14B:
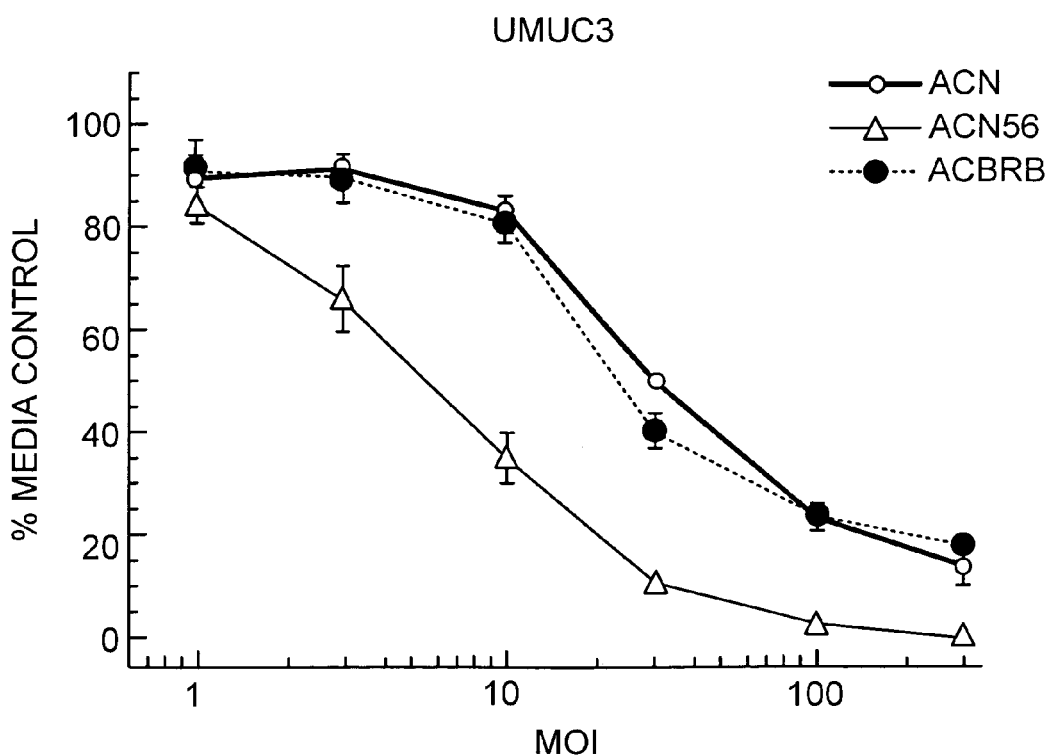

Plots shown in FIG. 14 show that treatment of $RB^{pos}$ cell lines RT4 and UM-UC-3 with ACBRB did not appreciably effect cell proliferation, as measured in [$^3$H] thymidine incorporation, compared to treatment with ACN. However treatment with ACN56 resulted in an approximate 5 fold decrease in $ED_{50}$ compared to ACN or ACBRB. This suggested that ACN56, but not ACBRB, was able to exert antiproliferative effects in cells with endogenous RB.

ACN56 does not induce apoptosis is $RB^{pos}$ cells. One of the hallmarks of apoptosis is DNA fragmentation, which was monitored by FACS analysis as the appearance of cells with less than $G_1$ DNA content. A549 (human lung carcinoma, $p53^{pos}$, $RB^{pos}$) cells were plated $5 \times 10^5$ cells/T75 flasks. The following day media was aspirated and cells fed with 7.5 ml fresh media. Cells were treated with ACN53 (Wills et al., *Human Gene Therapy* 5:1079 (1994)), ACBRB, or ACN56E4 at $6 \times 10^6$ iu/ml. Cells were harvested 24 hours after infection, or fed with fresh media and harvested 5 days after infection. As a positive control, G122 (human glioblastoma $p53^{mut}$) cells were infected with ACN53 $5 \times 10^5$ iu/ml and harvested 24 hours after infection. Unattached and attached cells were harvested for FACS analysis and fixed by 67% methanol. Fixed cells were pelletted and resuspended in 4% BSA, 5 µg/ml RNAse in PBS and incubated 37° for 30 min. An equal volume of 100 µg/ml propidium iodide was then added to stain total DNA. Cells were analyzed on a Becton/Dickinson FACSCAN. Markers were set for sub G1, G1, S, and G2/M populations to determine percent cells n each region.

Data shown in TABLE 4 summarize the results obtained. A549 cells showed a slight accumulation of cells (9%) with sub $G_1$ DNA content 24 hours after ACN 53 infection. As expected $p53^{mut}$ G122 cells had 32% of the cells with sub G1 DNA content 24 hours after ACN53 infection, indicating these cells are undergoing apoptosis. There was no appreciable increase in cells with sub $G_1$ DNA content either 1 day or 5 days after ACBRB or ACN56 treatment of A549 cells. In contrast to ACN53, in which sub $G_1$ DNA content was noted in concert with antiproliferative effects, ACN56 did not lead to apoptosis but rather exerted antiproliferative effects independently of an apoptotic mechanism.

TABLE 4

| Cell line | Treatment | Time | % sub-$G_1$ |
|---|---|---|---|
| G122 | untreated | day 1 | 2 |
| G122 | ACN | day 1 | 1 |
| G122 | ACN53 | day 1 | 32 |

TABLE 4-continued

| Cell line | Treatment | Time | % sub-$G_1$ |
|---|---|---|---|
| A549 | untreated | day 1 | 0 |
| A549 | ACN53 | day 1 | 9 |
| A549 | ACBRB | day 1 | 0 |
| A549 | ACN56 | day 1 | 2 |
| A549 | untreated | day 5 | 0 |
| A549 | ACBRB | day 5 | 1 |
| A549 | ACN56 | day 5 | 1 |

ACN56 inhibits proliferation but does not induce cell death. 5637 cells (human bladder carcinoma, p53$^{mut}$; RB$^{neg}$ ATCC) were assayed for inhibition of proliferation by [$^3$H] thymidine incorporation and for cytotoxicity by endogenous lactate dehydrogenase (LDH) release. For the proliferation assay, cells were plated at 5×10$^3$ cells per well in 96-well plate. The following day cells were treated with ACN, ACBRB, and ACN56 at MOIs ranging from 1 to 300 in triplicate. 48 hours after infection, cells were pulsed with [$^3$H] thymidine for 18 hours. Cells were harvested and counted by liquid scintillation (TopCount Packard Instruments, Meridian, Conn.). The % control growth was determined as the dose that resulted in 50% incorporation compared to untreated control.

The cytotoxicity assay was performed on cells plated and infected similarly as in the $^3$H-thymidine incorporation experiment. ACN53 was included as a positive control. 72 hours after infection, lysis was measured using Cytotox 96 detection kit (Promega) which measures endogenous LDH released into the media. Maximal lysis was determined by normalization to the maximal LDH release detected from similarly treated cells to control for changes in total cell number due to antiproliferative effects of treatment.

Figure 15A:
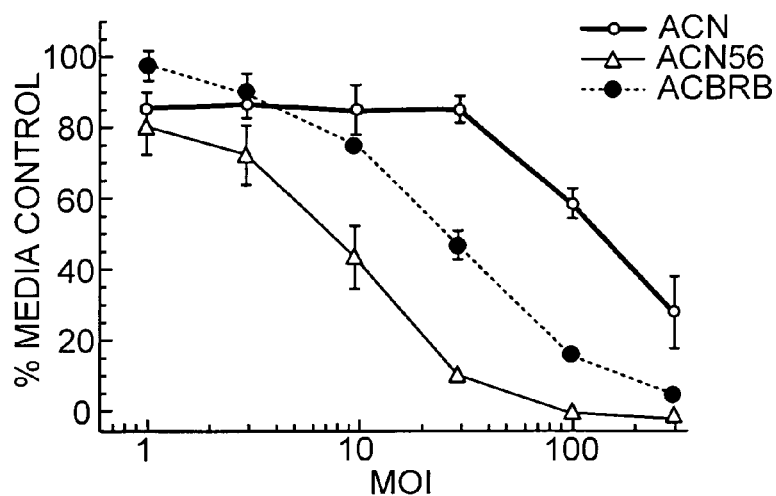
FIGS. 15A–C show the effect of viral construct including control, those coding for the $p110^{RB}$ and the $p56^{RB}$ proteins on cellular proliferation of RB negative tumor cell lines assayed by [³H] thymidine incorporation and for cytotoxicity by endogenous lactate dehydrogenose release.
Figure 15B:
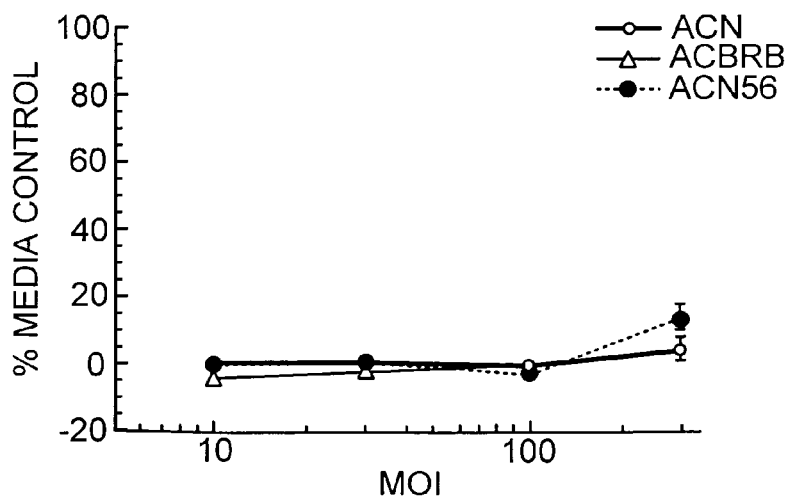
Figure 15C:
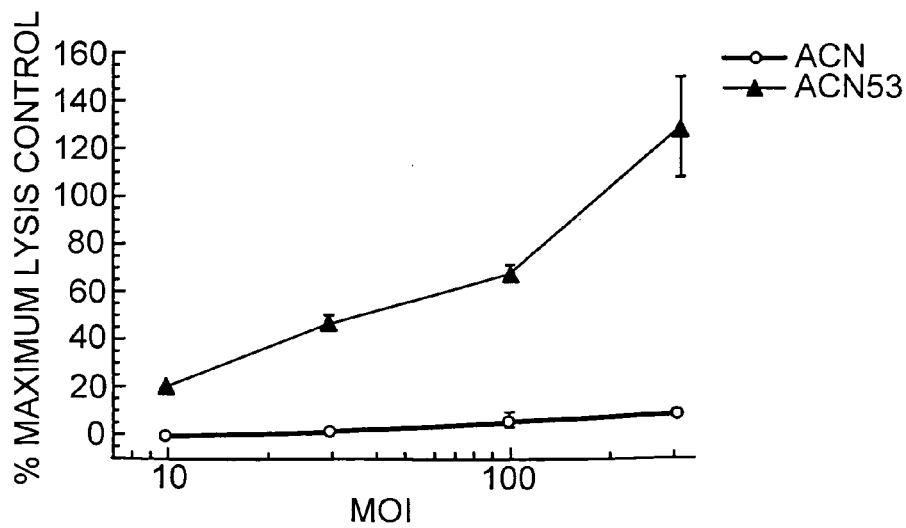
Figure 16:
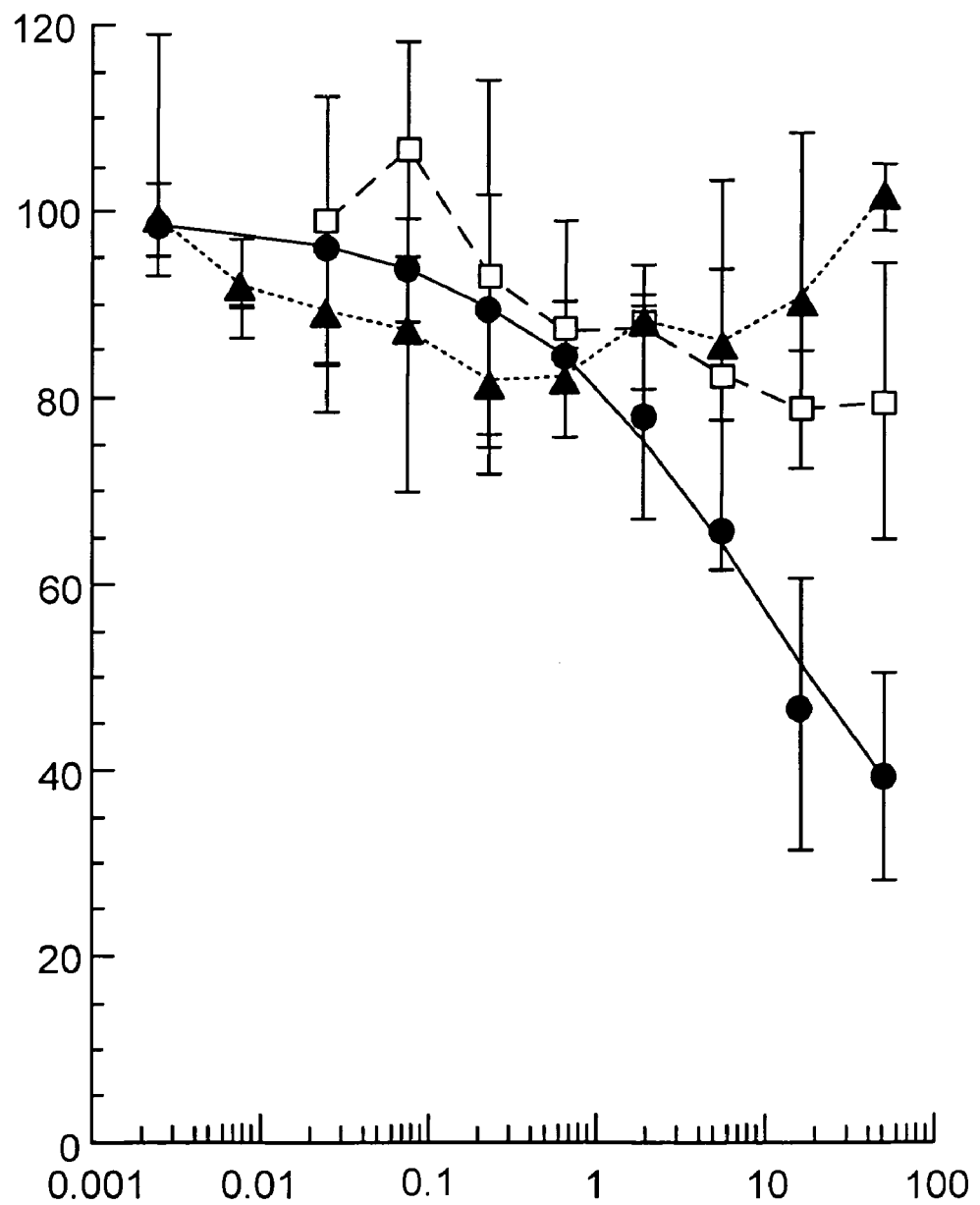
FIG. 16. ACN56 Inhibits Proliferation of Normal Human Cells. ACN56E4 (encoding $p56^{RB}$), ACBRB (encoding p110$^{RB}$) and ACBGL (encoding beta-galactosidase) were tested for their ability to inhibit DNA synthesis of normal human mammary epithelial cells. This was assessed by infecting these cells at various multiplicities of infection (MOI) and then measuring incorporation of tritiated thymidine. The circles refer to ACN56, triangles to ACBRB and squares are ACBGL. Unlike p110$^{RB}$ or beta-galactosidase, adenoviral expressed p56RB inhibits the growth of normal human cells.

Data shown in FIG. 15 top panel demonstrate the antiproliferative effects of ACBRB and ACN56 compared to the control virus ACN. The ED$_{50}$ was approximately 5 and 20 fold less for ACBRB and ACN56 respectively compared to ACN. The cytotoxic effects of the viruses is shown in the bottom panels. The bottom left panel demonstrated that there was no increase in cytotoxicity over the range of MOIs which clearly showed an antiproliferative effect. In comparison the bottom right panel shows that cytotoxicity was induced by ACN53. Therefore, in contrast to ACN53, ACBRB and ACN56 exerted antiproliferative effects without inducing cytotoxicity.

p56$^{RB}$ Inhibits Cellular Proliferation—Normal Human Mammary Epithelial Cells Tumor Suppressor Gene Therapy Using p56$^{RB}$ The antiproliferative activity of replication incompetent adenovirus samples expressing different forms of Rb protein were assessed using a thymidine incorporation bioassay. Normal human mammary epithelial cells (HMEC, Clonetics Corp.) at low passage were seeded into 96-well flat-bottom microtiter dishes in 100 µL serum-free Mammary Epithelial Growth Medium® at a density of 8×10$^3$ per well. After an overnight incubation at 37° C. in a humidified air/5% CO$_2$ chamber, ACN56, ACBRB, or ACBGL (i.e., a recombinant adenovirus that produces E. coli β-galactosidase) (Wills et al., Human Gene Therapy 5:1079 (1994)) were added in 100 µL aliquots; a serial three-fold dilution starting from a multiplicity of infection of 50 was used to infect the cells. The negative control sample, ACBGL, was included on every microtiter plate. All plates were returned to the incubator for an additional 48 hours. All dilutions were tested in triplicate. Cells were labeled with [$^3$H] thymidine (Amersham) at 0.5 µCi/well for 6 hours at 37° C. in a humidified air/5% CO$_2$ chamber. Next, cells were detached from the plastic substratum by removing the media and adding 100 µL/well trypsin-EDTA (Gibco BRL) at 37° C. for 10 minutes, transferring them to a 96-well glass fiber filter cassette (Packard Instrument Co.) using a 96-well harvester (Packard Instruments). Sample filter cassettes were wetted with 50 µL/well MicroScint™ 20 (Packard Instruments) scintillation cocktail, covered with Top-Seal™ (Packard Instruments) sealant analysis. Samples were counted for tritium for 1 minute. Data (in CPM) were compared with media control values and plotted. Dose-response curves and values for ED50 were determined using the general form of the four parameter logistic equation and KaleidaGraph V3.0 (Synergy Software).

TABLE 2

Microinjection of Synchronously Growing Cells in Early G1

| Cell Line | Protein | Number of Injected Cells[a] | Number of BrdU Stained Cells[b] | % of Injected Cells Entering S phase |
|---|---|---|---|---|
| Saos-2 | p110$^{RBc}$ | 256 | 8 | 3 |
| | RαG$^C$ | 270 | 173 | 64 |
| | p56$^{RB}$ | 388 | 12 | 3 |
| | RαG | 295 | 202 | 68 |
| | Histone | 595 | 333 | 56 |
| | Uninjected | | | 84 |
| | p56$^{Rbd}$ | 247 | 10 | 4 |
| | p56$^{RBd}$ + .495 | 80 | 24 | 30 |
| | p56$^{RBd}$ + .47 | 596 | 95 | 16 |
| | p56$^{RB}$d + R2 | 712 | 43 | 6 |
| SR40 | p56$^{RB}$ | 89 | 3 | 3 |
| | Histone | 201 | 105 | 52 |
| | RαG | 134 | 74 | 55 |

[a]The total number of injected calls (Texas Red positive) counted from at least three independent experiments.
[b]The number of injected cells which incorporated BrdU as evidenced by uniform staining with a fluorescein linked anti-BrdU antibody. Cells were incubated in growth media with BrdU for 24 hours after injection and prior to staining.
[c]Injections were performed in a buffer containing 10% glycerol.
[d]p56RB was injected at a concentration of about .3–.5 mg/ml, rather than 1 mg/ml, in these experiments.

TABLE 3

SV40 T-antigen relieves the block to G1 progression by p56$^{RB}$

| Cell Line | Protein[a] | Number of Injected Cells[b] | Number of BrdU Stained Cells[c] | % of Injected Cells Entering S phase |
|---|---|---|---|---|
| Saos-2 | p56$^{RB}$ | 247 | 10 | 4 |
| | p56$^{RB}$ + T | 724 | 203 | 28 |
| | p56$^{RB}$ + p53 | 727 | 7 | 1 |
| CV-1 | p56$^{RB}$ | 459 | 46 | 10 |
| | Histone | 471 | 259 | 55 |
| | RαG | 332 | 176 | 53 |
| COS-7 | p56$^{RB}$ | 257 | 224 | 87 |
| | Histone | 191 | 159 | 83 |

[a]All proteins were injected at concentrations of about 1 mg/ml, except for p56$^{RB}$ in Saos-2 cells which was injected at about .3–.5 mg/ml.
[b]Cell lines are microinjected 6–8 hours after release from nocodazole treatment. The total number of injected cells (Texas Red positive) is indicated.
[c]Cells were incubated in growth media with BrdU for 24 hours after injection and prior to staining.

TABLE 1

| | Microinjected of Asynchronously Growing Cells | | |
|---|---|---|---|
| Protein Sample | Total Number of Injected Cells[a] | Total Number of BrdU Stained Cells[b] | % Injected Cells Entering S Phase |
| pp110[RB] | 1094 | 416 | 38 |
| P56[RB] | 1315 | 408 | 31 |
| RαG | 1725 | 707 | 41 |
| Histone | 106 | 42 | 40 |
| Uninjected | | | 41 |

[a]The total number of injected cells (Texas Red positive) counted from at least five independent experiments, except for the Histone injection which represents one experiment.
[b]The number of injected cells which incorporated BrdU as evidenced by uniform staining with a fluorescein linked anti-BrdU antibody. Cells were incubated in growth media with BrdU for 4 hours prior to staining.

What is claimed is:

1. A method of treating non-malignant, hyperproliferating mammalian cells comprising contacting the cells with an adenoviral expression vector comprising a gene encoding P56$^{RB}$ or a p110$^{RB}$ retinoblastoma polypeptide, wherein the p110$^{RB}$ retinoblastoma polypeptide comprises the amino acid sequence of SEQ ID NO:2; whereby the hyperproliferation of the non-malignant mammalian cells is inhibited.

2. The method of claim 1, wherein the expression vector comprises a gene encoding a p56$^{RB}$ retinoblastoma polypeptide.

3. The method of claim 1, wherein the expression vector comprises a gene encoding a p110$^{RB}$ retinoblastoma polypeptide comprising the amino acid sequence of SEQ ID NO:2.

4. The method of claim 1, wherein said p56$^{RB}$ polypeptide extends between amino acids 379 and amino acids 928 of SEQ ID NO:2.

5. The method of claim 1, wherein the cells express an endogenous mutant p110$^{RB}$ polypeptide.

6. The method of claim 2, wherein the cells express an endogenous wild-type p110$^{RB}$ polypeptide.

7. The method of claim 1, wherein the cells are contacted with a pharmaceutically acceptable carrier comprising the adenoviral expression vector.

8. The method of claim 7, wherein the carrier comprises a polymeric matrix, a microsphere, or a liposome.

9. The method of claim 1, wherein the hyperproliferation of the non-malignant mammalian cells causes vasoproliferative disease.

10. The method of claim 1, wherein the expression vector is ACN56E3 or ACN56E4.

11. The method of claim 1, wherein the non-malignant hyperproliferating cells comprise benign tumor cells.

* * * * *

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
    (A) LENGTH: 2994 base pairs
    (B) TYPE: nucleic acid
    (C) STRANDEDNESS: single
    (D) TOPOLOGY: linear (ii) MOLECULE TYPE: DNA (genomic)

(ix) FEATURE:
    (A) NAME/KEY: CDS
    (B) LOCATION: 139..2922
    (D) OTHER INFORMATION: /product= "RB protein"
        /note= "retinoblastoma (RB) gene"

(ix) FEATURE:
    (A) NAME/KEY: -
    (B) LOCATION: 1273..2922
    (D) OTHER INFORMATION: /note= "truncated RB protein fragment
        p56-RB"

(ix) FEATURE:
    (A) NAME/KEY: -
    (B) LOCATION: 2887..2922
    (D) OTHER INFORMATION: /note= "RB protein C-terminal peptide"

(xi) SEQUENCE DESCRIPTION: SEQ ID NO:1:

```
TTCCGGTTTT TCTCAGGGGA CGTTGAAATT ATTTTTGTAA CGGGAGTCGG GAGAGGACGG        60

GGCGTGCCCC GCGTGCGCGC GCGTCGTCCT CCCCGGCGCT CCTCCACAGC TCGCTGGCTC       120

CCGCCGCGGA AAGGCGTC ATG CCG CCC AAA ACC CCC CGA AAA ACG GCC GCC        171
                    Met Pro Pro Lys Thr Pro Arg Lys Thr Ala Ala
                      1               5                  10
```

```
                                                     -continued

ACC GCC GCC GCT GCC GCC GCG GAA CCC CCG GCA CCG CCG CCG CCC          219
Thr Ala Ala Ala Ala Ala Ala Glu Pro Pro Ala Pro Pro Pro Pro
            15                  20                  25

CCT CCT GAG GAG GAC CCA GAG CAG GAC AGC GGC CCG GAG GAC CTG CCT     267
Pro Pro Glu Glu Asp Pro Glu Gln Asp Ser Gly Pro Glu Asp Leu Pro
            30                  35                  40

CTC GTC AGG CTT GAG TTT GAA GAA ACA GAA GAA CCT GAT TTT ACT GCA     315
Leu Val Arg Leu Glu Phe Glu Glu Thr Glu Glu Pro Asp Phe Thr Ala
        45                  50                  55

TTA TGT CAG AAA TTA AAG ATA CCA GAT CAT GTC AGA GAG AGA GCT TGG     363
Leu Cys Gln Lys Leu Lys Ile Pro Asp His Val Arg Glu Arg Ala Trp
60                  65                  70                  75

TTA ACT TGG GAG AAA GTT TCA TCT GTG GAT GGA GTA TTG GGA GGT TAT     411
Leu Thr Trp Glu Lys Val Ser Ser Val Asp Gly Val Leu Gly Gly Tyr
                80                  85                  90

ATT CAA AAG AAA AAG GAA CTG TGG GGA ATC TGT ATC TTT ATT GCA GCA     459
Ile Gln Lys Lys Lys Glu Leu Trp Gly Ile Cys Ile Phe Ile Ala Ala
                    95                  100                 105

GTT GAC CTA GAT GAG ATG TCG TTC ACT TTT ACT GAG CTA CAG AAA AAC     507
Val Asp Leu Asp Glu Met Ser Phe Thr Phe Thr Glu Leu Gln Lys Asn
                110                 115                 120

ATA GAA ATC AGT GTC CAT AAA TTC TTT AAC TTA CTA AAA GAA ATT GAT     555
Ile Glu Ile Ser Val His Lys Phe Phe Asn Leu Leu Lys Glu Ile Asp
            125                 130                 135

ACC AGT ACC AAA GTT GAT AAT GCT ATG TCA AGA CTG TTG AAG AAG TAT     603
Thr Ser Thr Lys Val Asp Asn Ala Met Ser Arg Leu Leu Lys Lys Tyr
140                 145                 150                 155

GAT GTA TTG TTT GCA CTC TTC AGC AAA TTG GAA AGG ACA TGT GAA CTT     651
Asp Val Leu Phe Ala Leu Phe Ser Lys Leu Glu Arg Thr Cys Glu Leu
                160                 165                 170

ATA TAT TTG ACA CAA CCC AGC AGT TCG ATA TCT ACT GAA ATA AAT TCT     699
Ile Tyr Leu Thr Gln Pro Ser Ser Ser Ile Ser Thr Glu Ile Asn Ser
                175                 180                 185

GCA TTG GTG CTA AAA GTT TCT TGG ATC ACA TTT TTA TTA GCT AAA GGG     747
Ala Leu Val Leu Lys Val Ser Trp Ile Thr Phe Leu Leu Ala Lys Gly
                190                 195                 200

GAA GTA TTA CAA ATG GAA GAT GAT CTG GTG ATT TCA TTT CAG TTA ATG     795
Glu Val Leu Gln Met Glu Asp Asp Leu Val Ile Ser Phe Gln Leu Met
    205                 210                 215

CTA TGT GTC CTT GAC TAT TTT ATT AAA CTC TCA CCT CCC ATG TTG CTC     843
Leu Cys Val Leu Asp Tyr Phe Ile Lys Leu Ser Pro Pro Met Leu Leu
220                 225                 230                 235

AAA GAA CCA TAT AAA ACA GCT GTT ATA CCC ATT AAT GGT TCA CCT CGA     891
Lys Glu Pro Tyr Lys Thr Ala Val Ile Pro Ile Asn Gly Ser Pro Arg
                240                 245                 250

ACA CCC AGG CGA GGT CAG AAC AGG AGT GCA CGG ATA GCA AAA CAA CTA     939
Thr Pro Arg Arg Gly Gln Asn Arg Ser Ala Arg Ile Ala Lys Gln Leu
                255                 260                 265

GAA AAT GAT ACA AGA ATT ATT GAA GTT CTC TGT AAA GAA CAT GAA TGT     987
Glu Asn Asp Thr Arg Ile Ile Glu Val Leu Cys Lys Glu His Glu Cys
            270                 275                 280

AAT ATA GAT GAG GTG AAA AAT GTT TAT TTC AAA AAT TTT ATA CCT TTT    1035
Asn Ile Asp Glu Val Lys Asn Val Tyr Phe Lys Asn Phe Ile Pro Phe
    285                 290                 295

ATG AAT TCT CTT GGA CTT GTA ACA TCT AAT GGA CTT CCA GAG GTT GAA    1083
Met Asn Ser Leu Gly Leu Val Thr Ser Asn Gly Leu Pro Glu Val Glu
300                 305                 310                 315

AAT CTT TCT AAA CGA TAC GAA GAA ATT TAT CTT AAA AAT AAA GAT CTA    1131
Asn Leu Ser Lys Arg Tyr Glu Glu Ile Tyr Leu Lys Asn Lys Asp Leu
                320                 325                 330
```

```
                                              -continued
GAT GCA AGA TTA TTT TTG GAT CAT GAT AAA ACT CTT CAG ACT GAT TCT      1179
Asp Ala Arg Leu Phe Leu Asp His Asp Lys Thr Leu Gln Thr Asp Ser
            335                 340                 345

ATA GAC AGT TTT GAA ACA CAG AGA ACA CCA CGA AAA AGT AAC CTT GAT      1227
Ile Asp Ser Phe Glu Thr Gln Arg Thr Pro Arg Lys Ser Asn Leu Asp
        350                 355                 360

GAA GAG GTG AAT GTA ATT CCT CCA CAC ACT CCA GTT AGG ACT GTT ATG      1275
Glu Glu Val Asn Val Ile Pro Pro His Thr Pro Val Arg Thr Val Met
365                 370                 375

AAC ACT ATC CAA CAA TTA ATG ATG ATT TTA AAT TCA GCA AGT GAT CAA      1323
Asn Thr Ile Gln Gln Leu Met Met Ile Leu Asn Ser Ala Ser Asp Gln
380                 385                 390                 395

CCT TCA GAA AAT CTG ATT TCC TAT TTT AAC AAC TGC ACA GTG AAT CCA      1371
Pro Ser Glu Asn Leu Ile Ser Tyr Phe Asn Asn Cys Thr Val Asn Pro
                400                 405                 410

AAA GAA AGT ATA CTG AAA AGA GTG AAG GAT ATA GGA TAC ATC TTT AAA      1419
Lys Glu Ser Ile Leu Lys Arg Val Lys Asp Ile Gly Tyr Ile Phe Lys
            415                 420                 425

GAG AAA TTT GCT AAA GCT GTG GGA CAG GGT TGT GTC GAA ATT GGA TCA      1467
Glu Lys Phe Ala Lys Ala Val Gly Gln Gly Cys Val Glu Ile Gly Ser
        430                 435                 440

CAG CGA TAC AAA CTT GGA GTT CGC TTG TAT TAC CGA GTA ATG GAA TCC      1515
Gln Arg Tyr Lys Leu Gly Val Arg Leu Tyr Tyr Arg Val Met Glu Ser
    445                 450                 455

ATG CTT AAA TCA GAA GAA GAA CGA TTA TCC ATT CAA AAT TTT AGC AAA      1563
Met Leu Lys Ser Glu Glu Glu Arg Leu Ser Ile Gln Asn Phe Ser Lys
460                 465                 470                 475

CTT CTG AAT GAC AAC ATT TTT CAT ATG TCT TTA TTG GCG TGC GCT CTT      1611
Leu Leu Asn Asp Asn Ile Phe His Met Ser Leu Leu Ala Cys Ala Leu
                480                 485                 490

GAG GTT GTA ATG GCC ACA TAT AGC AGA AGT ACA TCT CAG AAT CTT GAT      1659
Glu Val Val Met Ala Thr Tyr Ser Arg Ser Thr Ser Gln Asn Leu Asp
            495                 500                 505

TCT GGA ACA GAT TTG TCT TTC CCA TGG ATT CTG AAT GTG CTT AAT TTA      1707
Ser Gly Thr Asp Leu Ser Phe Pro Trp Ile Leu Asn Val Leu Asn Leu
        510                 515                 520

AAA GCC TTT GAT TTT TAC AAA GTG ATC GAA AGT TTT ATC AAA GCA GAA      1755
Lys Ala Phe Asp Phe Tyr Lys Val Ile Glu Ser Phe Ile Lys Ala Glu
    525                 530                 535

GGC AAC TTG ACA AGA GAA ATG ATA AAA CAT TTA GAA CGA TGT GAA CAT      1803
Gly Asn Leu Thr Arg Glu Met Ile Lys His Leu Glu Arg Cys Glu His
540                 545                 550                 555

CGA ATC ATG GAA TCC CTT GCA TGG CTC TCA GAT TCA CCT TTA TTT GAT      1851
Arg Ile Met Glu Ser Leu Ala Trp Leu Ser Asp Ser Pro Leu Phe Asp
                560                 565                 570

CTT ATT AAA CAA TCA AAG GAC CGA GAA GGA CCA ACT GAT CAC CTT GAA      1899
Leu Ile Lys Gln Ser Lys Asp Arg Glu Gly Pro Thr Asp His Leu Glu
            575                 580                 585

TCT GCT TGT CCT CTT AAT CTT CCT CTC CAG AAT AAT CAC ACT GCA GCA      1947
Ser Ala Cys Pro Leu Asn Leu Pro Leu Gln Asn Asn His Thr Ala Ala
        590                 595                 600

GAT ATG TAT CTT TCT CCT GTA AGA TCT CCA AAG AAA AAA GGT TCA ACT      1995
Asp Met Tyr Leu Ser Pro Val Arg Ser Pro Lys Lys Lys Gly Ser Thr
    605                 610                 615

ACG CGT GTA AAT TCT ACT GCA AAT GCA GAG ACA CAA GCA ACC TCA GCC      2043
Thr Arg Val Asn Ser Thr Ala Asn Ala Glu Thr Gln Ala Thr Ser Ala
620                 625                 630                 635

TTC CAG ACC CAG AAG CCA TTG AAA TCT ACC TCT CTT TCA CTG TTT TAT      2091
Phe Gln Thr Gln Lys Pro Leu Lys Ser Thr Ser Leu Ser Leu Phe Tyr
                640                 645                 650
```

```
AAA AAA GTG TAT CGG CTA GCC TAT CTC CGG CTA AAT ACA CTT TGT GAA      2139
Lys Lys Val Tyr Arg Leu Ala Tyr Leu Arg Leu Asn Thr Leu Cys Glu
            655                 660                 665

CGC CTT CTG TCT GAG CAC CCA GAA TTA GAA CAT ATC ATC TGG ACC CTT      2187
Arg Leu Leu Ser Glu His Pro Glu Leu Glu His Ile Ile Trp Thr Leu
            670                 675                 680

TTC CAG CAC ACC CTG CAG AAT GAG TAT GAA CTC ATG AGA GAC AGG CAT      2235
Phe Gln His Thr Leu Gln Asn Glu Tyr Glu Leu Met Arg Asp Arg His
685                 690                 695

TTG GAC CAA ATT ATG ATG TGT TCC ATG TAT GGC ATA TGC AAA GTG AAG      2283
Leu Asp Gln Ile Met Met Cys Ser Met Tyr Gly Ile Cys Lys Val Lys
700                 705                 710                 715

AAT ATA GAC CTT AAA TTC AAA ATC ATT GTA ACA GCA TAC AAG GAT CTT      2331
Asn Ile Asp Leu Lys Phe Lys Ile Ile Val Thr Ala Tyr Lys Asp Leu
                720                 725                 730

CCT CAT GCT GTT CAG GAG ACA TTC AAA CGT GTT TTG ATC AAA GAA GAG      2379
Pro His Ala Val Gln Glu Thr Phe Lys Arg Val Leu Ile Lys Glu Glu
            735                 740                 745

GAG TAT GAT TCT ATT ATA GTA TTC TAT AAC TCG GTC TTC ATG CAG AGA      2427
Glu Tyr Asp Ser Ile Ile Val Phe Tyr Asn Ser Val Phe Met Gln Arg
            750                 755                 760

CTG AAA ACA AAT ATT TTG CAG TAT GCT TCC ACC AGG CCC CCT ACC TTG      2475
Leu Lys Thr Asn Ile Leu Gln Tyr Ala Ser Thr Arg Pro Pro Thr Leu
            765                 770                 775

TCA CCA ATA CCT CAC ATT CCT CGA AGC CCT TAC AAG TTT CCT AGT TCA      2523
Ser Pro Ile Pro His Ile Pro Arg Ser Pro Tyr Lys Phe Pro Ser Ser
780                 785                 790                 795

CCC TTA CGG ATT CCT GGA GGG AAC ATC TAT ATT TCA CCC CTG AAG AGT      2571
Pro Leu Arg Ile Pro Gly Gly Asn Ile Tyr Ile Ser Pro Leu Lys Ser
                800                 805                 810

CCA TAT AAA ATT TCA GAA GGT CTG CCA ACA CCA ACA AAA ATG ACT CCA      2619
Pro Tyr Lys Ile Ser Glu Gly Leu Pro Thr Pro Thr Lys Met Thr Pro
            815                 820                 825

AGA TCA AGA ATC TTA GTA TCA ATT GGT GAA TCA TTC GGG ACT TCT GAG      2667
Arg Ser Arg Ile Leu Val Ser Ile Gly Glu Ser Phe Gly Thr Ser Glu
            830                 835                 840

AAG TTC CAG AAA ATA AAT CAG ATG GTA TGT AAC AGC GAC CGT GTG CTC      2715
Lys Phe Gln Lys Ile Asn Gln Met Val Cys Asn Ser Asp Arg Val Leu
845                 850                 855

AAA AGA AGT GCT GAA GGA AGC AAC CCT CCT AAA CCA CTG AAA AAA CTA      2763
Lys Arg Ser Ala Glu Gly Ser Asn Pro Pro Lys Pro Leu Lys Lys Leu
860                 865                 870                 875

CGC TTT GAT ATT GAA GGA TCA GAT GAA GCA GAT GGA AGT AAA CAT CTC      2811
Arg Phe Asp Ile Glu Gly Ser Asp Glu Ala Asp Gly Ser Lys His Leu
                880                 885                 890

CCA GGA GAG TCC AAA TTT CAG CAG AAA CTG GCA GAA ATG ACT TCT ACT      2859
Pro Gly Glu Ser Lys Phe Gln Gln Lys Leu Ala Glu Met Thr Ser Thr
            895                 900                 905

CGA ACA CGA ATG CAA AAG CAG AAA ATG AAT GAT AGC ATG GAT ACC TCA      2907
Arg Thr Arg Met Gln Lys Gln Lys Met Asn Asp Ser Met Asp Thr Ser
            910                 915                 920

AAC AAG GAA GAG AAA TGAGGATCTC AGGACCTTGG TGGACACTGT GTACACCTCT      2962
Asn Lys Glu Glu Lys
925

GGATTCATTG TCTCTCACAG ATGTGACTGT AT                                  2994
```

(2) INFORMATION FOR SEQ ID NO:2:

(i) SEQUENCE CHARACTERISTICS:
        (A) LENGTH: 928 amino acids
        (B) TYPE: amino acid
        (D) TOPOLOGY: linear (ii) MOLECULE TYPE: protein (xi) SEQUENCE DESCRIPTION: SEQ ID NO:2:

```
Met Pro Pro Lys Thr Pro Arg Lys Thr Ala Thr Ala Ala Ala Ala
 1               5                  10                  15

Ala Ala Glu Pro Pro Ala Pro Pro Pro Pro Pro Pro Glu Glu Asp
                20                  25                  30

Pro Glu Gln Asp Ser Gly Pro Glu Asp Leu Pro Leu Val Arg Leu Glu
                35                  40                  45

Phe Glu Glu Thr Glu Glu Pro Asp Phe Thr Ala Leu Cys Gln Lys Leu
         50                  55                  60

Lys Ile Pro Asp His Val Arg Glu Arg Ala Trp Leu Thr Trp Glu Lys
 65                  70                  75                  80

Val Ser Ser Val Asp Gly Val Leu Gly Gly Tyr Ile Gln Lys Lys Lys
                 85                  90                  95

Glu Leu Trp Gly Ile Cys Ile Phe Ile Ala Ala Val Asp Leu Asp Glu
                100                 105                 110

Met Ser Phe Thr Phe Thr Glu Leu Gln Lys Asn Ile Glu Ile Ser Val
                115                 120                 125

His Lys Phe Phe Asn Leu Leu Lys Glu Ile Asp Thr Ser Thr Lys Val
                130                 135                 140

Asp Asn Ala Met Ser Arg Leu Leu Lys Lys Tyr Asp Val Leu Phe Ala
145                 150                 155                 160

Leu Phe Ser Lys Leu Glu Arg Thr Cys Glu Leu Ile Tyr Leu Thr Gln
                165                 170                 175

Pro Ser Ser Ser Ile Ser Thr Glu Ile Asn Ser Ala Leu Val Leu Lys
                180                 185                 190

Val Ser Trp Ile Thr Phe Leu Leu Ala Lys Gly Glu Val Leu Gln Met
                195                 200                 205

Glu Asp Asp Leu Val Ile Ser Phe Gln Leu Met Leu Cys Val Leu Asp
                210                 215                 220

Tyr Phe Ile Lys Leu Ser Pro Pro Met Leu Leu Lys Glu Pro Tyr Lys
225                 230                 235                 240

Thr Ala Val Ile Pro Ile Asn Gly Ser Pro Arg Thr Pro Arg Arg Gly
                245                 250                 255

Gln Asn Arg Ser Ala Arg Ile Ala Lys Gln Leu Glu Asn Asp Thr Arg
                260                 265                 270

Ile Ile Glu Val Leu Cys Lys Glu His Glu Cys Asn Ile Asp Glu Val
                275                 280                 285

Lys Asn Val Tyr Phe Lys Asn Phe Ile Pro Phe Met Asn Ser Leu Gly
                290                 295                 300

Leu Val Thr Ser Asn Gly Leu Pro Glu Val Glu Asn Leu Ser Lys Arg
305                 310                 315                 320

Tyr Glu Glu Ile Tyr Leu Lys Asn Lys Asp Leu Asp Ala Arg Leu Phe
                325                 330                 335

Leu Asp His Asp Lys Thr Leu Gln Thr Asp Ser Ile Asp Ser Phe Glu
                340                 345                 350

Thr Gln Arg Thr Pro Arg Lys Ser Asn Leu Asp Glu Glu Val Asn Val
                355                 360                 365
```

```
Ile Pro Pro His Thr Pro Val Arg Thr Val Met Asn Thr Ile Gln Gln
370             375                 380

Leu Met Met Ile Leu Asn Ser Ala Ser Asp Gln Pro Ser Glu Asn Leu
385                 390                 395                 400

Ile Ser Tyr Phe Asn Asn Cys Thr Val Asn Pro Lys Glu Ser Ile Leu
                405                 410                 415

Lys Arg Val Lys Asp Ile Gly Tyr Ile Phe Lys Glu Lys Phe Ala Lys
            420                 425                 430

Ala Val Gly Gln Gly Cys Val Glu Ile Gly Ser Gln Arg Tyr Lys Leu
            435                 440                 445

Gly Val Arg Leu Tyr Tyr Arg Val Met Glu Ser Met Leu Lys Ser Glu
450                 455                 460

Glu Glu Arg Leu Ser Ile Gln Asn Phe Ser Lys Leu Leu Asn Asp Asn
465                 470                 475                 480

Ile Phe His Met Ser Leu Leu Ala Cys Ala Leu Glu Val Val Met Ala
                485                 490                 495

Thr Tyr Ser Arg Ser Thr Ser Gln Asn Leu Asp Ser Gly Thr Asp Leu
                500                 505                 510

Ser Phe Pro Trp Ile Leu Asn Val Leu Asn Leu Lys Ala Phe Asp Phe
                515                 520                 525

Tyr Lys Val Ile Glu Ser Phe Ile Lys Ala Glu Gly Asn Leu Thr Arg
530                 535                 540

Glu Met Ile Lys His Leu Glu Arg Cys Glu His Arg Ile Met Glu Ser
545                 550                 555                 560

Leu Ala Trp Leu Ser Asp Ser Pro Leu Phe Asp Leu Ile Lys Gln Ser
                565                 570                 575

Lys Asp Arg Glu Gly Pro Thr Asp His Leu Glu Ser Ala Cys Pro Leu
                580                 585                 590

Asn Leu Pro Leu Gln Asn Asn His Thr Ala Ala Asp Met Tyr Leu Ser
                595                 600                 605

Pro Val Arg Ser Pro Lys Lys Lys Gly Ser Thr Thr Arg Val Asn Ser
            610                 615                 620

Thr Ala Asn Ala Glu Thr Gln Ala Thr Ser Ala Phe Gln Thr Gln Lys
625                 630                 635                 640

Pro Leu Lys Ser Thr Ser Leu Ser Leu Phe Tyr Lys Lys Val Tyr Arg
                645                 650                 655

Leu Ala Tyr Leu Arg Leu Asn Thr Leu Cys Glu Arg Leu Leu Ser Glu
                660                 665                 670

His Pro Glu Leu Glu His Ile Ile Trp Thr Leu Phe Gln His Thr Leu
                675                 680                 685

Gln Asn Glu Tyr Glu Leu Met Arg Asp Arg His Leu Asp Gln Ile Met
                690                 695                 700

Met Cys Ser Met Tyr Gly Ile Cys Lys Val Lys Asn Ile Asp Leu Lys
705                 710                 715                 720

Phe Lys Ile Ile Val Thr Ala Tyr Lys Asp Leu Pro His Ala Val Gln
                725                 730                 735

Glu Thr Phe Lys Arg Val Leu Ile Lys Glu Glu Glu Tyr Asp Ser Ile
                740                 745                 750

Ile Val Phe Tyr Asn Ser Val Phe Met Gln Arg Leu Lys Thr Asn Ile
                755                 760                 765

Leu Gln Tyr Ala Ser Thr Arg Pro Pro Thr Leu Ser Pro Ile Pro His
770                 775                 780
```

```
Ile Pro Arg Ser Pro Tyr Lys Phe Pro Ser Ser Pro Leu Arg Ile Pro
785                 790                 795                 800

Gly Gly Asn Ile Tyr Ile Ser Pro Leu Lys Ser Pro Tyr Lys Ile Ser
            805                 810                 815

Glu Gly Leu Pro Thr Pro Thr Lys Met Thr Pro Arg Ser Arg Ile Leu
            820                 825                 830

Val Ser Ile Gly Glu Ser Phe Gly Thr Ser Glu Lys Phe Gln Lys Ile
            835                 840                 845

Asn Gln Met Val Cys Asn Ser Asp Arg Val Leu Lys Arg Ser Ala Glu
            850                 855                 860

Gly Ser Asn Pro Pro Lys Pro Leu Lys Lys Leu Arg Phe Asp Ile Glu
865                 870                 875                 880

Gly Ser Asp Glu Ala Asp Gly Ser Lys His Leu Pro Gly Glu Ser Lys
            885                 890                 895

Phe Gln Gln Lys Leu Ala Glu Met Thr Ser Thr Arg Thr Arg Met Gln
            900                 905                 910

Lys Gln Lys Met Asn Asp Ser Met Asp Thr Ser Asn Lys Glu Glu Lys
            915                 920                 925
```